United States Patent
Tong

(10) Patent No.: US 8,809,550 B2
(45) Date of Patent: Aug. 19, 2014

(54) ANDROGEN RECEPTOR ANTAGONISTS AND USES THEREOF

(76) Inventor: Youzhi Tong, Jiangsu (CN)

( * ) Notice: Subject to any disclaimer, the term of this patent is extended or adjusted under 35 U.S.C. 154(b) by 0 days.

(21) Appl. No.: 13/395,066

(22) PCT Filed: Sep. 8, 2010

(86) PCT No.: PCT/CN2010/076726
§ 371 (c)(1),
(2), (4) Date: Mar. 8, 2012

(87) PCT Pub. No.: WO2011/029392
PCT Pub. Date: Mar. 17, 2011

(65) Prior Publication Data
US 2012/0172406 A1 Jul. 5, 2012

Related U.S. Application Data

(60) Provisional application No. 61/241,051, filed on Sep. 10, 2009.

(51) Int. Cl.
*A61K 31/255* (2006.01)
*C07D 233/00* (2006.01)
*C07D 233/76* (2006.01)
*C07D 233/64* (2006.01)

(52) U.S. Cl.
CPC ............ *C07D 233/76* (2013.01); *C07D 233/64* (2013.01)
USPC ....................................... 548/319.5; 514/548

(58) Field of Classification Search
None
See application file for complete search history.

(56) References Cited

U.S. PATENT DOCUMENTS

| | | | |
|---|---|---|---|
| 5,434,176 A | 7/1995 | Claussner et al. | |
| 5,589,497 A | 12/1996 | Claussner et al. | |
| 5,646,172 A | 7/1997 | Claussner et al. | |
| 5,705,654 A | 1/1998 | Claussner et al. | |
| 5,750,553 A | 5/1998 | Claussner et al. | |
| 6,087,509 A | 7/2000 | Claussner et al. | |
| 6,242,611 B1 | 6/2001 | Claussner et al. | |
| 6,982,265 B1 | 1/2006 | Hunt et al. | |
| 7,112,675 B2 | 9/2006 | Hunt et al. | |
| 7,244,733 B2 | 7/2007 | Hunt et al. | |
| 7,709,516 B2 | 5/2010 | Labrie et al. | |
| 7,709,517 B2 | 5/2010 | Sawyers et al. | |
| 7,803,826 B2 | 9/2010 | Tachibana et al. | |
| 8,168,627 B2 | 5/2012 | Labrie et al. | |
| 8,470,829 B2 | 6/2013 | Tachibana et al. | |
| 2010/0063120 A1 | 3/2010 | Nique et al. | |
| 2011/0306615 A1 | 12/2011 | Tachibana et al. | |

FOREIGN PATENT DOCUMENTS

| | | | |
|---|---|---|---|
| CN | 101817787 A | 9/2010 | |
| EP | 1 790 640 A1 | 5/2007 | |
| JP | 8-99977 A | 4/1996 | |
| JP | 9-507241 A | 7/1997 | |
| JP | 2000502053 A | 2/2000 | |
| JP | 2000502669 A | 3/2000 | |
| JP | 2008543792 A | 12/2008 | |
| KR | 20070106969 A | 11/2007 | |
| KR | 20080014039 A | 2/2008 | |
| WO | 9518794 A1 | 7/1995 | |
| WO | 9719064 A1 | 5/1997 | |
| WO | 9723464 A1 | 7/1997 | |
| WO | WO2004031160 A2 | 4/2004 | |
| WO | WO2006028226 A1 | 3/2006 | |
| WO | 2006013887 A1 | 9/2006 | |
| WO | WO2006124118 A1 | 11/2006 | |
| WO | 2006133567 A1 | 12/2006 | |
| WO | WO2007127010 A2 | 11/2007 | |
| WO | 2007137874 A2 | 12/2007 | |
| WO | WO2008093838 A1 | 8/2008 | |
| WO | WO2009055053 A2 | 4/2009 | |
| WO | 2011/029329 A1 | 3/2011 | |

OTHER PUBLICATIONS

Silva, A., Mini-Reviews in Medicinal Chemistry, 2005, vol. 5, pp. 893-014.*
Tran, C., et al., "Development of a Second-Generation Antiandrogen for Treatment of Advanced Prostate Cancer," Science, 2009, vol. 324, pp. 787-790.
Tran, C., et al., "Supporting Online Material for "Development of a Second-Generation Antiandrogen for Treatment of Advanced Prostate Cancer"," 2009, 19 pages.
First Office Action along with its English translation regarding a Japanese counterpart application (2012-528220).
First Office Action along with its English translation regarding a Korean counterpart application (6-2012-011267-8).

* cited by examiner

*Primary Examiner* — Heidi Reese
(74) *Attorney, Agent, or Firm* — Kilpatrick Townsend & Stockton LLP

(57) ABSTRACT

The present invention relates to novel substituted thioimidazolidinone compounds and pharmaceutical compositions comprising such compounds for treatment of androgen receptor-associated diseases or disorders, such as prostate cancer, benign prostatic hypertrophy, male hair loss, muscle loss, acne and hirsutism.

18 Claims, 1 Drawing Sheet

Compound example 12 promoted hair-growth in mouse models.
Day 1*
Control Group
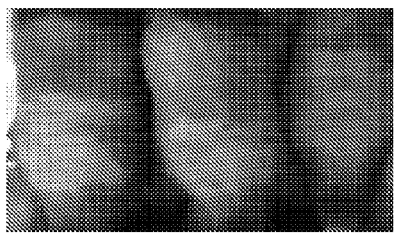
0.2% of Compound Example
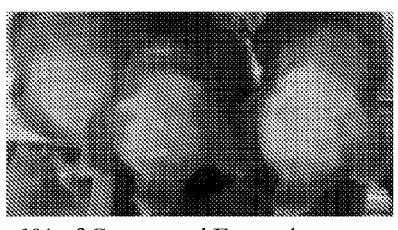
1% of Compound Example
Day 19*
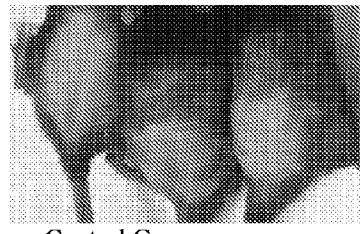
Control Group
(Score$_{ave}$=0.5)
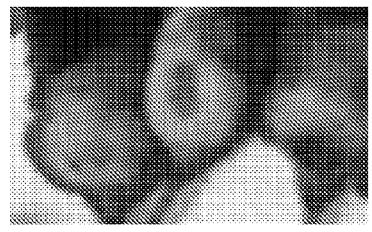
0.2% of Compound Example 12
(Score$_{ave}$=2.8)
1% of Compound Example 12
(Score$_{ave}$=3.7)
*Positive control (1% RU-58841)
(Score$_{ave}$=1.9 at Day 19)

ANDROGEN RECEPTOR ANTAGONISTS AND USES THEREOF

FIELD OF THE INVENTION

The present invention relates to novel substituted thioimidazolidinone compounds and pharmaceutical compositions comprising such compounds for treatment of androgen receptor-associated diseases or disorders, such as prostate cancer, benign prostatic hypertrophy, male hair loss, muscle loss, acne and hirsutism.

BACKGROUND OF THE INVENTION

The androgen receptor (AR) is a 110 Kda steroidal nuclear receptor. One of its key functions is androgen-activated gene transcription. The androgen receptor plays an important role in many male hormone related diseases such as prostate cancer, benign prostatic hypertrophy, male hair loss, muscle loss and hirsutism (hypertrichosis). For this reason, selective androgen receptor antagonists may be useful for such conditions and diseases including but not limited to: male contraception; treatment of a variety of male hormone-related conditions such as hypersexuality and sexual deviation; treatment of conditions including benign prostatic hyperplasia, acne vugaris, androgenetic alopecia, and hirsutism; preventing the symptoms associated with reduced testosterone such as hot flashes after castration; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer is one of the most common cancers in men around the world, and is one of the leading causes of cancer death in men in the United States. Current standard treatment for local prostate cancer is surgery and radiation. Unfortunately, the cancer relapses in one-third of the treated patients. Together with patients diagnosed with advanced prostate cancer, they are treated with surgical castration or chemical castration, which is called hormone therapy (HT). Often HT is also combined with drugs acting as androgen receptor antagonists. Hormone therapy is highly effective for controlling cancer cells in most of patients with advanced prostate cancer. However, the prostate cancer cells eventually adapt to the low androgen environment and become resistant to HT. As a result, the cancer will recur in almost all such patients in 2-5 years.

Androgen receptor antagonist drugs, such as flutamide and bicalutamide, were originally designed to avoid the side effects of HT and to overcome resistance in prostate cancer patients. Although these androgen receptor antagonists work well as a co-treatment with HT in naïve advanced prostate cancer patients, their efficacy against refractory prostate cancer, as a single agent, or co-treatment, has been limited. There have been reports that androgen agonism was observed for hydroxyfluamide (the active form of flutamide) and bicalutamide. The residual agonistic effect may be responsible for the drugs' ineffectiveness in overcoming resistance. The therapeutic benefit of these androgen receptor antagonist drugs have also been hampered by significant side effects such as liver toxicities associated with flutamide and bicalutamide. Recent studies have suggested that reactivation of the AR signaling pathway may be the root cause for developing resistance to HT. Mutation and over-expression of AR are two of the common underlying molecular mechanisms for the observed resistance.

Therefore, there is significant medical need for better androgen receptor antagonists that should have potent antagonism but devoid of any agonism when treating castration resistant prostate cancer cells. There is also a need to reduce the observed side effects such as liver toxicity found in existing androgen receptor antagonist drugs.

SUMMARY OF THE INVENTION

The present invention comprises compounds of formulas (I)-(IV) below, methods of using such compounds as antagonists of androgen receptors, and pharmaceutical compositions containing such compounds and salts thereof.

In one embodiment, the invention is directed to compounds and pharmaceutical compositions comprising a compound of formula (I):

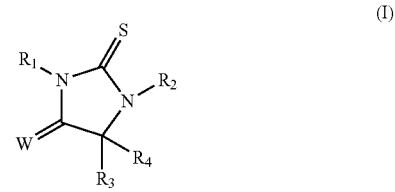

(I)

or a pharmaceutically-acceptable salt, solvate, hydrate, prodrug or derivative thereof,
wherein $R_1$ is selected from

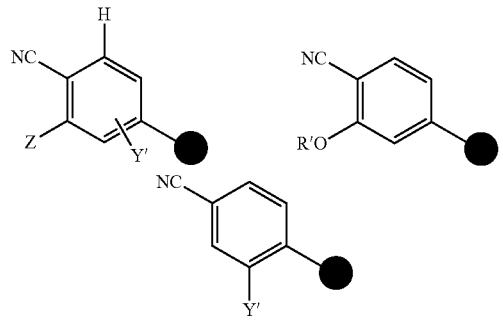

wherein Z is selected from hydrogen, $CF_3$, alkoxy, $CF_3O$, halogen, cyano and $C_1$-$C_4$ alkyl optionally substituted with one or more halogens;
Y is independently selected from one or two halogen, alkoxy, hydroxyl, $CF_3O$ and cyano;
W is selected from oxygen, sulfur and two hydrogens;
$R_3$ and $R_4$ are independently selected from $C_1$-$C_4$ alkyl optionally substituted with one or more fluoro or hydroxyl groups, or $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen; and
$R_2$ is a substituted or unsubstituted alkyl, aryl, heteroaryl or heterocyclic group.

In certain embodiments, Y is halogen or cyano. In certain embodiments, Z is halogen, methoxy, cyano, methyl or $CF_3$. In certain embodiments, W is oxygen.
In certain embodiments, $R_2$ is a phenyl or naphthyl group. In certain embodiments, $R_2$ is an aryl group substituted with one or more $C_1$-$C_6$ alkyl, C(O)NHR'', $SO_2R''$, $SO_2NHR''$, cyano, hydroxyl, alkoxy, C(S)NHR", C(O)OR", $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR". In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments $R_2$ is an unsubstituted heteroaryl group. In certain embodiments, $R_2$ is a heteroaryl group substituted with one or more $C_1$-$C_6$ alkyl, C(O)NHR", $SO_2$NHR", cyano, C(S)NHR", C(O)OR", hydroxyl, alkoxy, $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiment, $R_2$ is a substituted saturated heterocyclic group, such as but not limited to 3-piperidine, 4-piperidine, tetrahydropyrane, 3-pyrrolidine or tetrahydrofuran.

In certain embodiments, $R_3$ and $R_4$ are independently selected from methyl, ethyl, or methyl optionally substituted with one or more fluoro groups. In certain embodiments, $R_3$ and $R_4$ and the carbon to which they are attached together form a cyclopropyl, cyclobutyl, cyclopentyl or cyclohexyl ring which may be optionally substituted with one or more fluoro or hydroxyl groups.

In another embodiment, the invention is directed to compounds and pharmaceutical compositions comprising a compound of formula (II):

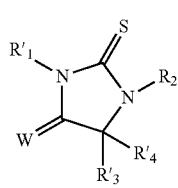

(II)

or a pharmaceutically-acceptable salt, solvate, hydrate, prodrug or derivative thereof,
wherein $R'_1$ is selected from

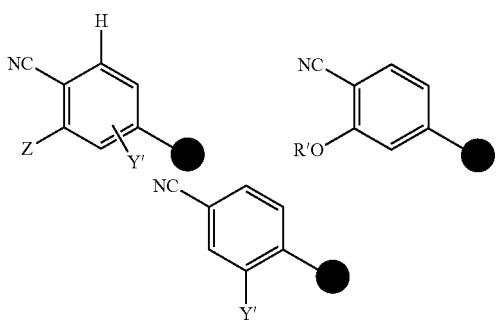

wherein Z is selected from hydrogen, $CF_3$, alkoxy, $CF_3O$, halogen, cyano and $C_1$-$C_4$ alkyl optionally substituted with one or more halogen;
Y' is independently selected from one or more alkyl and $CF_3$;
R' is selected from $C_1$-$C_3$ alkyl or $CF_3$;
W is selected from oxygen, sulfur and two hydrogens;
$R'_3$ and $R'_4$ and the carbon to which they are attached together form a 3-6 membered cycloalkyl ring wherein one or more carbons may be optional substituted with one or more fluoro or hydroxyl groups, and wherein one of the carbons is optionally an oxygen or nitrogen; and
$R_2$ is a substituted or unsubstituted alkyl, aryl, heteroaryl or heterocyclic group.

In certain embodiments, Y' is methyl, ethyl, or $CF_3$. In certain embodiments, R' is methyl, ethyl or $CF_3$. In certain embodiments, Z is halogen, methoxy, cyano, methyl or $CF_3$.

In certain embodiments, $R_2$ is phenyl or naphthyl. In certain embodiments, $R_2$ is an aryl group substituted with one or more $C_1$-$C_6$ alkyl, C(O)NHR", $SO_2$R", $SO_2$NHR", cyano, hydroxyl, alkoxy, C(S)NHR", C(O)OR", $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR". In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments, $R_2$ is a heteroaryl group substituted with one or more $C_1$-$C_6$ alkyl, C(O)NHR", $SO_2$NHR", cyano, C(S)NHR", C(O)OR", hydroxyl, alkoxy, $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiments, $R_2$ is a substituted saturated heterocyclic group, such as but not limited to 3-piperidine, 4-piperidine, tetrahydropyrane, 3-pyrrolidine or tetrahydrofuran.

In certain embodiments, $R'_3$ and $R'_4$ and the carbon to which they are attached together form a cyclopropyl, cyclobutyl, cyclopentyl or cyclohexyl ring which may be optionally substituted with one or more fluoro or hydroxyl groups.

In another embodiment, the invention is directed to compounds and pharmaceutical compositions comprising a compound of formula (III):

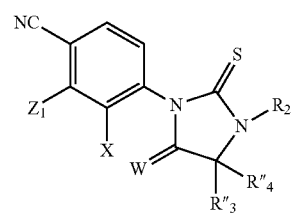

(III)

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, alkoxy, $CF_3O$, hydroxyl and cyano;

W is selected from oxygen, sulfur and two hydrogens;

$R''_3$ and $R''_4$ are methyl, or $R''_3$ and $R''_4$ together form a 3-6 membered alkyl ring which may be optionally substituted with one or more fluoro or hydroxyl groups; and $R_2$ is a substituted or unsubstituted alkyl, aryl, heteroaryl or heterocyclic group.

In certain embodiments, $Z_1$ is methyl, $CH_2F$, $CHF_2$, $CF_3$, methoxy, halogen and cyano. In certain embodiments, X is halogen.

In certain embodiments, $R_2$ is phenyl or naphthyl. In certain embodiments, $R_2$ is an aryl group substituted with one or more $C_1$-$C_6$ alkyl, C(O)NHR'', $SO_2R''$, $SO_2NHR''$, cyano, hydroxyl, alkoxy, C(S)NHR'', C(O)OR'', $CH_2(CH_2)_mQ$, halogen or a 5-6 membered heteroaryl group, where R'' is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR'', $SO_2R''$, $SO_2NHR''$, cyano, hydroxyl, alkoxy, C(S)NHR'' and C(O)OR''. In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments, $R_2$ is an unsubstituted heteroaryl group. In certain embodiments, $R_2$ is a heteroaryl group substituted with one or more $C_1$-$C_6$ alkyl, C(O)NHR'', $SO_2NHR''$, cyano, C(S)NHR'', C(O)OR'', hydroxyl, alkoxy, $CH_2(CH_2)_mQ$, halogen or a 5-6 membered heteroaryl group, where R'' is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR'', $SO_2R''$, $SO_2NHR''$, cyano, hydroxyl, alkoxy, C(S)NHR'' and C(O)OR''. In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiments, $R_2$ is a substituted saturated heterocyclic, such as but not limited to 3-piperidine, 4-piperidine, tetrahydropyrane, 3-pyrrolidine or tetrahydrofuran.

In certain embodiments, $R''_3$ and $R''_4$ are methyl, or $R''_3$ and $R''_4$ and the carbon to which they are attached together form a cyclopropyl or cyclobutyl or cyclopentyl or cyclohexyl ring which may be optionally substituted with one or more fluoro or hydroxyl groups.

In another embodiment, the invention is directed to compounds and pharmaceutical compositions comprising a compound of formula (IV):

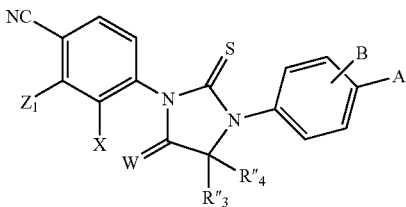

(IV)

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, alkoxy, $CF_3O$, hydroxyl and cyano;

W is selected from oxygen, sulfur and two hydrogens;

$R''_3$ and $R''_4$ are methyl, or $R''_3$ and $R''_4$ together form a 3-6 membered cycloalkyl ring optionally substituted with one or more fluoro or hydroxyl groups;

B is independently selected from one or more hydrogen, cyano, methyl, $CF_3$ or halogen; and A is selected from $C_1$-$C_6$ alkyl, C(O)NHR'', $SO_2R''$, $SO_2NHR''$, cyano, hydroxyl, alkoxy, C(S)NHR'', C(O)OR'', $CH_2(CH_2)_mQ$, halogen and a 5-6 membered heteroaryl group, where R'' is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR'', $SO_2R''$, $SO_2NHR''$, cyano, hydroxyl, alkoxy, C(S)NHR'' and C(O)OR''.

In certain embodiments, $Z_1$ is methyl, $CH_2F$, $CHF_2$, $CF_3$, methoxy, halogen or cyano. In certain embodiments, X is halogen.

In certain embodiments, $R''_3$ and $R''_4$ are methyl. In certain embodiments, $R''_3$ and $R''_4$ and the carbon to which they are attached together form a cyclopropyl or cyclobutyl or cyclopentyl or cyclohexyl ring which may be optionally substituted with one or more fluoro or hydroxyl groups.

In certain embodiments, B is independently one or more hydrogen, cyano, methyl, $CF_3$ or halogen.

In certain embodiments, A is methyl, ethyl, halogen, C(O)NHCH$_3$, C(O)NH$_2$, cyano, methoxy, ethoxy, $SO_2Me$, $SO_2NH_2CH_3$ or $SO_2NH_2$.

In certain embodiments, W is oxygen.

In certain embodiments of compounds of formulas (I)-(IV), W is oxygen.

In another embodiment, the invention is directed to a pharmaceutical composition comprising a compound of any one of formulas (I)-(IV) or its pharmaceutically acceptable salt, prodrug or a solution thereof as an active ingredient. In other embodiments, the invention is directed to a compound of any one of formulas (I)-(IV) and a pharmaceutically-acceptable carrier, diluent or excipient. In another embodiment, the invention is directed to a compound of any one of formulas (I)-(IV) for topical or dermal applications.

In other embodiments, method are provided for preventing, reducing the progression of, treating or regressing a disease or disorder related to androgen receptor activity by administering to a subject at risk for development thereof or afflicted therewith, a compound of any one of formulas (I)-(IV) or a pharmaceutical composition thereof. In certain embodiments, the disease or disorder is selected from hormone sensitive prostate cancer or hormone refractory prostate cancer, benign prostatic hyperplasia, acne, androgenic alopecia, hirsutism, excess sebum and alopecia due to an androgen receptor disorder, hypersexuality, sexual deviation, preventing or counteracting masculinisation in the case of transsexual women undergoing sex reassignment therapy, as an antineoplastic agent and palliative, adjuvant or neoadjuvant hormonal therapy in prostate cancer; or for decreasing the incidence of, halting or causing a regression of prostate cancer. In another embodiment, a compound of formula (I)-(IV) or a pharmaceutical composition thereof is useful for male contraception.

In a further embodiment, use of a compound of any one of formula (I)-(IV) or a pharmaceutical composition thereof is provided for male contraception, for treatment of any of the above diseases and disorders, for purposefully preventing or counteracting masculinisation in the case of transsexual women undergoing sex reassignment therapy, for decreasing the incidence of, halting or causing a regression of prostate cancer, or as an antineoplastic agent or palliative, adjuvant or neoadjuvant hormonal therapy in prostate cancer.

In a yet further embodiment, use of a compound of any one of formula (I)-(IV) or a pharmaceutical composition thereof is provided for the manufacture of a medicament for any of the above uses.

In another embodiment, the present invention provides a compound of any one of formula (I)-(IV) or a pharmaceutical composition thereof for any of the above uses.

BRIEF DESCRIPTION OF THE FIGURE

FIG. 1 shows the effect of a compound of the invention on promoting hair growth in a murine model.

DEFINITIONS

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds that combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CH$_2$(CH$_2$)$_{0-6}$CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —C(=O)NHR$_x$; —CH$_2$(CH$_2$)$_{0-6}$C(=O)N(R$_x$)$_2$; —CH$_2$(CH$_2$)$_{0-6}$C(=O)NHR$_x$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzo-fused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "C$_1$-C$_6$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

In certain embodiments of the compounds described herein, W is two hydrogens. For example, in formula I, when W is two hydrogens, formula I is I'. In formula II, when W is two hydrogens, formula II is II'. In formula III, when W is two hydrogens, formula III is III'. In formula I, when W is two hydrogens, formula IV is IV'. These are shown below.

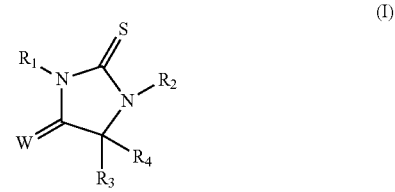

(I)

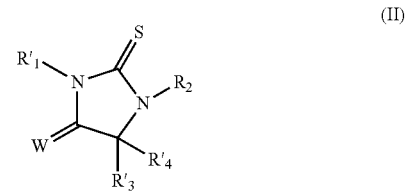

(II)

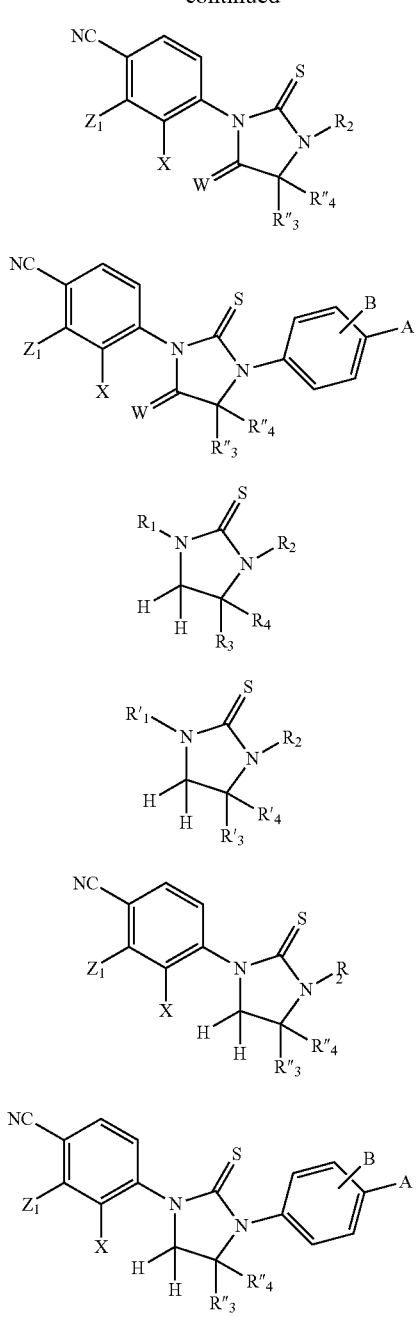

In other embodiments, one or more hydrogen atoms of a compound described herein can be replaced with a deuterium atom. Such deuterated derivatives are fully embraced by the disclosure herein. In certain embodiments, the hydrogen on a carbon of the aryl group or the heteroaryl group of $R_1$ or $R_2$ (formula I) of $R'_1$ of $R'_2$ (formula II) is replaced with a deuterium. In other embodiment, the hydrogen on a carbon of the alkyl group in Y, Z, R', Y' of formula I, II, III or IV or the alkoxy group in Y, Y', Z of formula I, II, III or IV is replaced with a deuterium. In other embodiment, the hydrogen on a carbon of the alkyl group or the alkoxy group in A or B of formula IV is replaced with a deuterium. In other embodiment, the hydrogen on a carbon of the alkyl group in $R_3/R_4$, $R'_3/R'_4$ of formula I-IV is replaced with a deuterium.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others prodrugs. A prodrug (also referred to as pro-drug) is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF THE INVENTION

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

As noted above, prostate cancer is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The present invention addresses the significant medical need for better androgen receptor antagonists that have potent antagonism but devoid of any agonism, and a reduction in the observed side effects such as liver toxicity found in existing androgen receptor antagonist drugs.

The compounds of the present invention are androgen receptor antagonists, which can be used to alleviate any condition associated with inappropriate activation of the androgen receptor. In addition to prostate cancer, other examples of such conditions include acne, hirsutism, seborrhoea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborhhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compounds may also be used topically to decrease seborrhea production and more specifically to alleviate hyperseborrhoea (oily skin), which can be used topically alleviate acne.

1) General Description of Compounds of the Invention

The present invention comprises compounds of formulas (I)-(IV) below, methods of using such compounds as antagonists of androgen receptors, and pharmaceutical compositions containing such compounds and salts thereof.

In certain embodiment, compounds of the invention include compounds of the general formula (I) or formula (II) as further defined below:

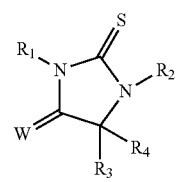

(I)

or a pharmaceutically-acceptable salt, solvate, hydrate, prodrug or derivative thereof, wherein $R_1$ is selected from

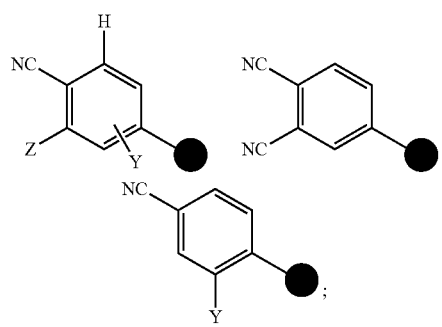

wherein Z is selected from hydrogen, $CF_3$, alkoxy, $CF_3O$, halogen, cyano and $C_1$-$C_4$ alkyl optionally substituted with one or more halogens;

Y is independently selected from one or two halogen, alkoxy, hydroxyl, $CF_3O$ and cyano;

W is selected from oxygen, sulfur and two hydrogens;

$R_3$ and $R_4$ are independently selected from $C_1$-$C_4$ alkyl optionally substituted with one or more fluoro or hydroxyl groups, or $R_3$ and $R_4$ together form a 3-6 membered cycloalkyl ring, wherein one or more carbons may be optional substituted with one or more fluoro or hydroxyl groups, and wherein one of the carbons is optionally an oxygen or nitrogen; and $R_2$ is a substituted or unsubstituted alkyl, aryl, heteroaryl or heterocyclic group.

Non-limiting examples of compound of formula (I) include

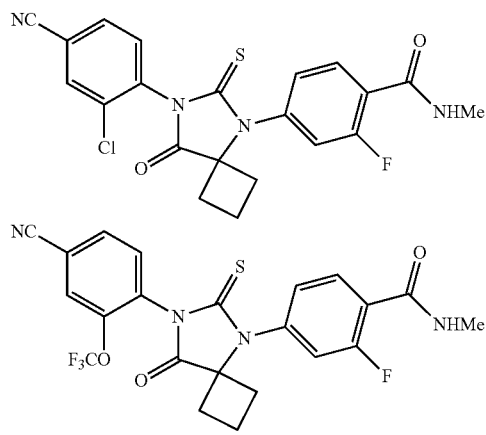

-continued
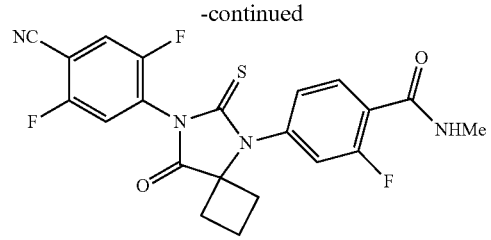
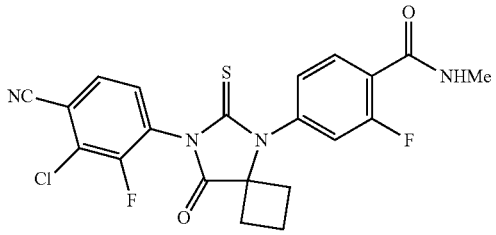
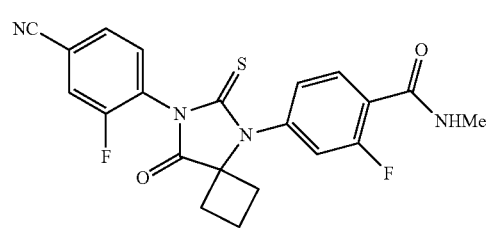
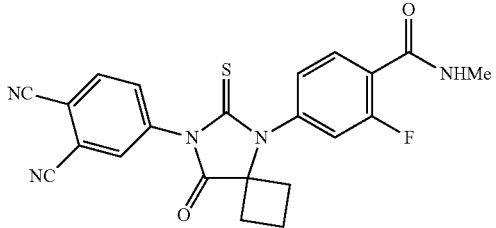
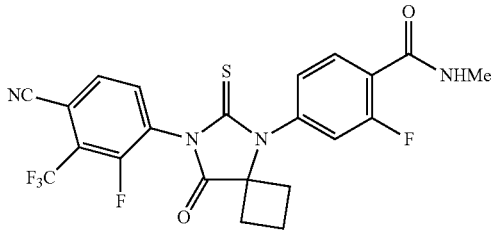
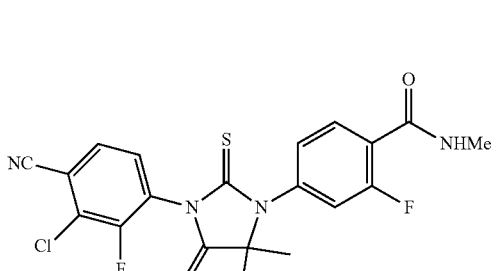
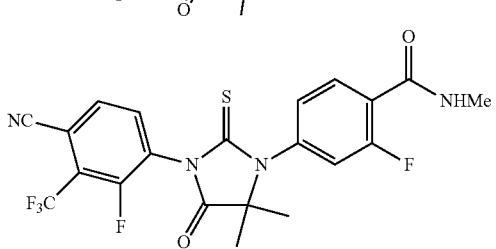
-continued
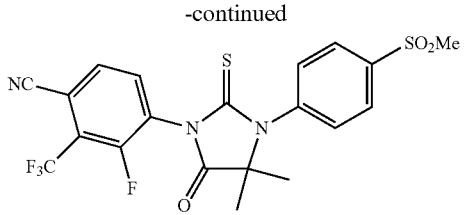
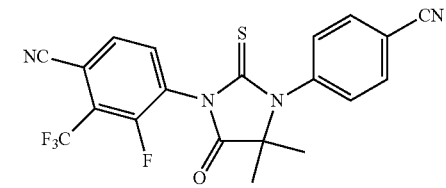
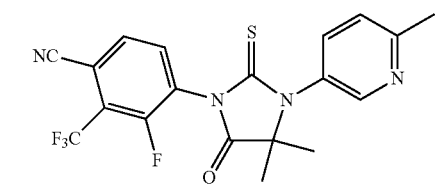
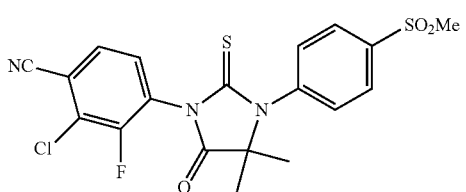
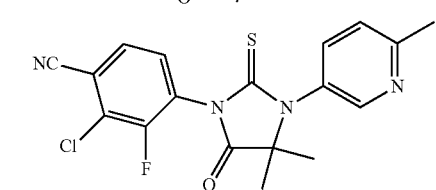
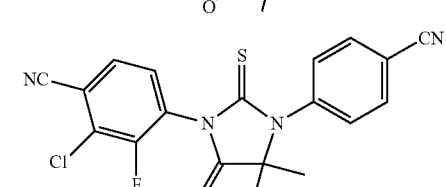
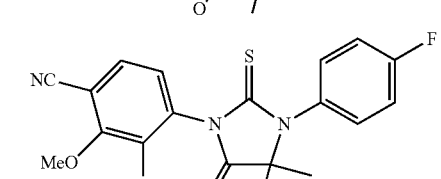
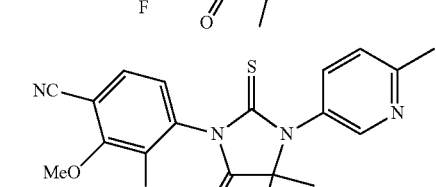
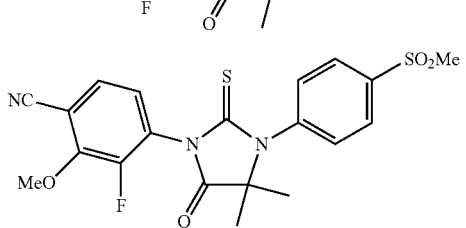

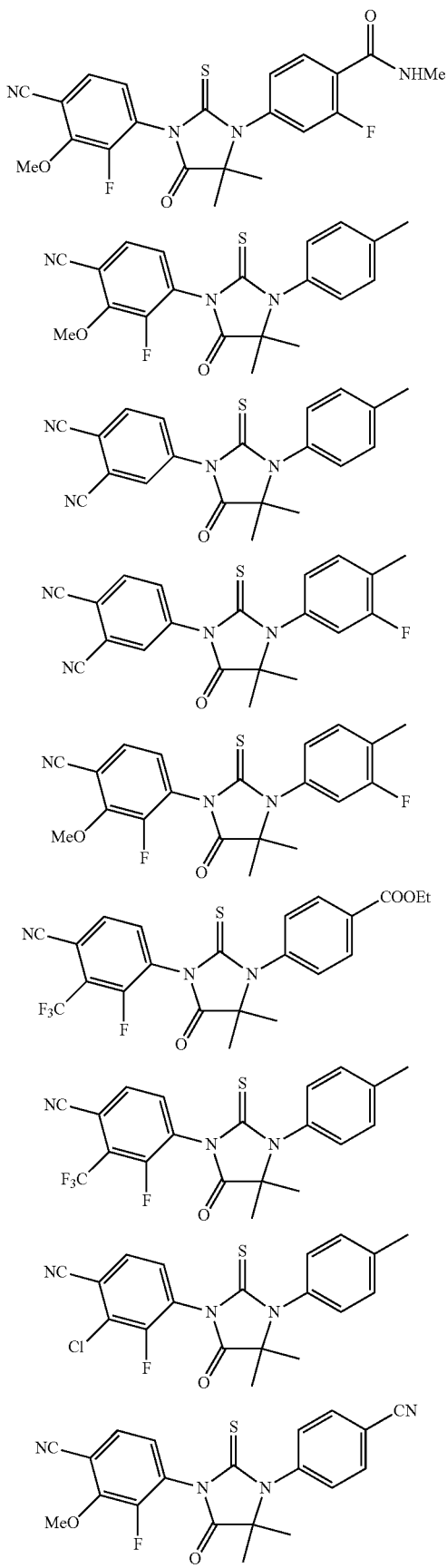

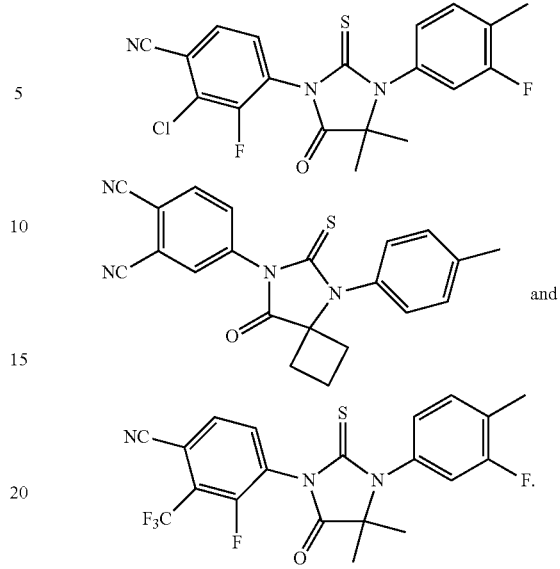

A number of important subclasses of the compounds of formula (I) deserve special mention. These subclasses, (III), and (IV), will be described in further detail below, and include compounds comprising one or more selections of the following substituents. Where aromatic rings may have one or more substituents, more than one such substituent may be present, each independent of the other.

1) Z is hydrogen;
2) Z is $C_1$-$C_4$ alkyl such as but not limited to methyl or ethyl, optionally substituted with one or more halogen groups;
3) Z is $CF_3$;
4) Z is alkoxy;
5) Z is $CF_3O$;
6) Z is halogen;
7) Z is cyano;
8) Z is fluoro;
9) Y is halogen;
10) Y is alkoxy such as but not limited to methoxy and ethoxy;
11) Y is hydroxyl;
12) Y is $CF_3O$;
13) Y is cyano;
14) W is oxygen;
15) W is sulfur;
16) W is two hydrogens;
17) $R_3$ and $R_4$ are independently methyl, ethyl, propyl or butyl groups;
18) $R_3$ and $R_4$ and the carbon to which they are attached together form a 3-6 membered cycloalkyl ring optionally substituted with one or more fluoro groups, and in which one of the carbons is optionally an oxygen or nitrogen;
19) $R_3$ and $R_4$ and the carbon to which they are attached together form cyclopropyl;
20) $R_3$ and $R_4$ and the carbon to which they are attached together form cyclobutyl;
21) $R_3$ and $R_4$ and the carbon to which they are attached together form cyclopentyl;
22) $R_3$ and $R_4$ and the carbon to which they are attached together form azetidine, pyrrolidine or piperidine;
23) $R_3$ and $R_4$ and the carbon to which they are attached together form oxetane, tetrahydrofuran or tetrahydropyran.
24) $R_2$ is phenyl or naphthyl;
25) $R_2$ is a substituted aryl group;

26) $R_2$ is an aryl group substituted with one or more $C_1$-$C_6$ alkyl, C(O)NHR", $SO_2$R", $SO_2$NHR", cyano, hydroxyl, alkoxy, C(S)NHR", C(O)OR", $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR";

27) $R_2$ is a substituted phenyl such as 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl;

28) $R_2$ is an unsubstituted heteroaryl group;

29) $R_2$ is a pyridinyl group;

30) $R_2$ is a pyridin-3-yl group;

31) $R_2$ is a substituted heteroaryl group;

32) $R_2$ is a heteroaryl group substituted with one or more $C_1$-$C_6$ alkyl, C(O)NHR", $SO_2$NHR", cyano, C(S)NHR", C(O)OR", hydroxyl, alkoxy, $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR";

33) $R_2$ is a substituted heteroaryl group such as 6-methyl-pyridin-3-yl;

34) $R_2$ is 6-methyl-pyridin-3-yl group;

35) $R_2$ is a substituted saturated heterocycle, such as but not limited to 3-piperidine, 4-piperidine, tetrahydropyrane, 3-pyrrolidine or tetrahydrofuran;

36) $R_1$ is

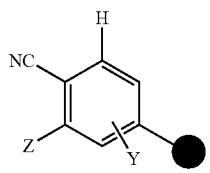

wherein Z and independently one or two Y are as described above;

37) $R_1$ is

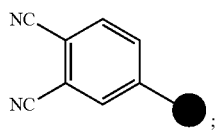

38) $R_1$ is

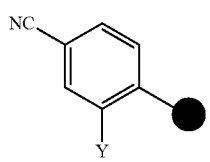

wherein Y is as described above;

39) $R_1$ is

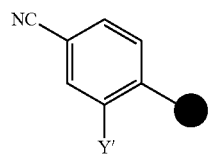

wherein Y' is a $C_1$-$C_6$ alkyl, such as methyl and ethyl;

40) $R_1$ is

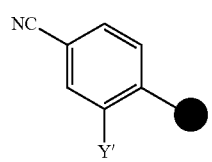

wherein Y' is a $C_1$-$C_6$ alkyl, such as methyl and ethyl, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen;

41) $R_1$ is

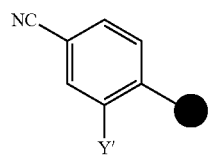

wherein Y' is $CF_3$;

42) $R_1$ is

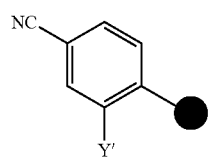

wherein Y' is $CF_3$, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen;

43) $R_1$ is

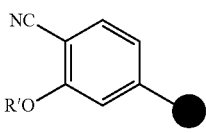

wherein R' is $C_1$-$C_3$ alkyl;

44) $R_1$ is

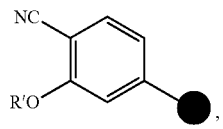

wherein R' is $C_1$-$C_3$ alkyl, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen;

45) $R_1$ is

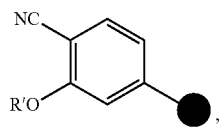

wherein R' is $CF_3$;

46) $R_1$ is

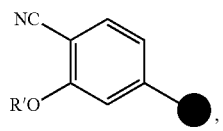

wherein R' is $CF_3$, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen;

47) $R_1$ is

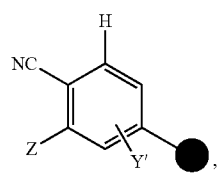

wherein Z is as described above and Y' is alkyl such as methyl and ethyl;

48) $R_1$ is

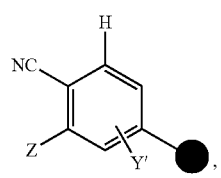

wherein Z is as described above and Y' is alkyl such as methyl and ethyl, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen;

49) $R_1$ is

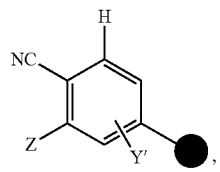

wherein Z is as described above and Y' is $CF_3$; and/or

50) $R_1$ is

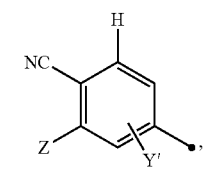

wherein Z is as described above and Y' is $CF_3$, and $R_3$ and $R_4$ and the carbon to which they are attached together form a 3-6 membered cycloalkyl ring optionally substituted with one or more fluoro or hydroxyl groups, and in which one of the carbons is optionally an oxygen or nitrogen.

In certain embodiments, the present invention defines particular classes of compounds of special interest, in one aspect, compounds of formula (II):

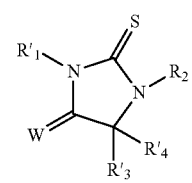

(II)

or a pharmaceutically-acceptable salt, solvate, hydrate, prodrug or derivative thereof, wherein $R'_1$ is selected from

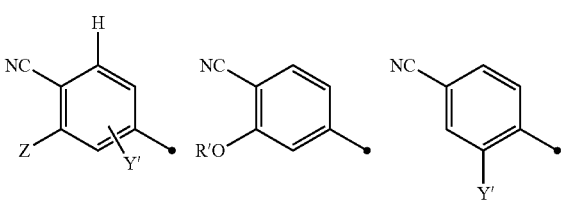

wherein Z is selected from hydrogen, $CF_3$, alkoxy, $CF_3O$, halogen, cyano and $C_1$-$C_4$ alkyl optionally substituted with one or more halogen;

Y' is selected from alkyl and $CF_3$;

R' is selected from $C_1$-$C_3$ alkyl or $CF_3$;

W is selected from oxygen, sulfur and two hydrogens;

$R'_3$ and $R'_4$ and the carbon to which they are attached together form a 3-6 membered cycloalkyl ring wherein one or more carbons may be optional substituted with one or more fluoro or hydroxyl groups, and wherein one of the carbons is optionally an oxygen or nitrogen; and $R_2$ is a substituted or unsubstituted alkyl, aryl, heteroaryl or heterocyclic group.

In certain embodiments, R'$_1$ is

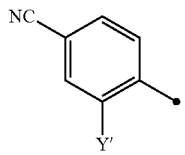

wherein Y' is methyl, ethyl, or CF$_3$.

In certain embodiments, R'$_1$ is

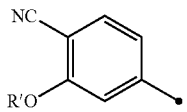

wherein R' is methyl, ethyl or CF$_3$.

In certain embodiments, R'$_1$ is

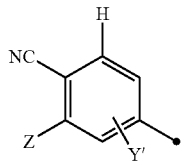

wherein Y' independently is one or two methyl, ethyl or CF$_3$, and Z is halogen, methoxy, cyano, methyl or CF$_3$.

In certain embodiments of compounds of formula (II), W is oxygen.

In certain embodiments, R$_2$ is a phenyl or naphthyl group. In certain embodiments, R$_2$ is an aryl group substituted with one or more C$_1$-C$_6$ alkyl, C(O)NHR", SO$_2$R", SO$_2$NHR", cyano, hydroxyl, alkoxy, C(S)NHR", C(O)OR", CH$_2$(CH$_2$)$_m$Q, halogen or a 5-6 membered heteroaryl group, where R" is selected from hydrogen, C$_1$-C$_6$ alkyl, C$_1$-C$_6$ cycloalkyl and C$_1$-C$_6$ alkenyl; m is an integer selected from 0 to 6; and Q is selected from C(O)NHR", SO$_2$R", SO$_2$NHR", cyano, hydroxyl, alkoxy, C(S)NHR" and C(O)OR".

In certain embodiments, R$_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments R$_2$ is an unsubstituted heteroaryl group. In certain embodiments R$_2$ is a pyridyl group. In certain embodiments, R$_2$ is a heteroaryl group substituted with one or more C$_1$-C$_6$ alkyl, C(O)NHR", SO$_2$NHR", cyano, C(S)NHR", C(O)OR", hydroxyl, alkoxy, CH$_2$(CH$_2$)$_m$Q, halogen or a 5-6 membered heteroaryl group, where R" is selected from hydrogen, C$_1$-C$_6$ alkyl, C$_1$-C$_6$ cycloalkyl and C$_1$-C$_6$ alkenyl; m is an integer selected from 0 to 6; and Q is selected from C(O)NHR", SO$_2$R", SO$_2$NHR", cyano, hydroxyl, alkoxy, C(S)NHR" and C(O)OR". In certain embodiments, R$_2$ is a substituted pyridyl group. In certain embodiments, R$_2$ is 6-methyl-pyridin-3-yl.

In certain embodiments, R$_2$ is a substituted alkyl group. In certain embodiments, R$_2$ is a substituted saturated heterocyclic group. In certain embodiments, R$_2$ is a substituted saturated heterocycle, such as but not limited to 3-piperidine, 4-piperidine, tetrahydropyrane, 3-pyrrolidine or tetrahydrofuran.

In certain embodiments, R'$_3$ and R'$_4$ and the carbon to which they are attached together form a cyclopropyl, cyclobutyl, cyclopentyl or cyclohexyl ring which may be optionally substituted with one or more fluoro or hydroxyl groups.

In certain embodiments, R$_2$ is a substituted saturated heterocycle, such as but not limited to 3-piperidine, 4-piperidine, tetrahydropyrane, 3-pyrrolidine or tetrahydrofuran.

Non-limiting examples of compounds in this embodiment of formula (II) include:

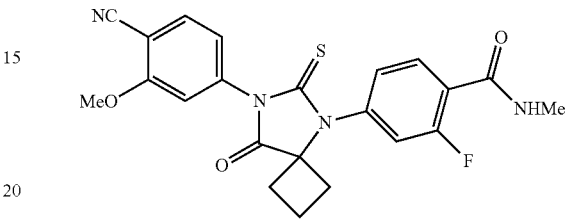

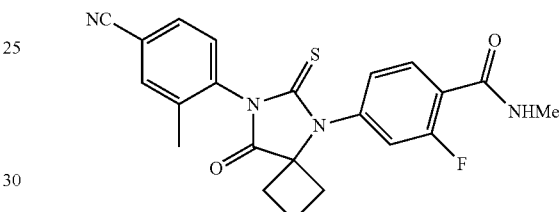

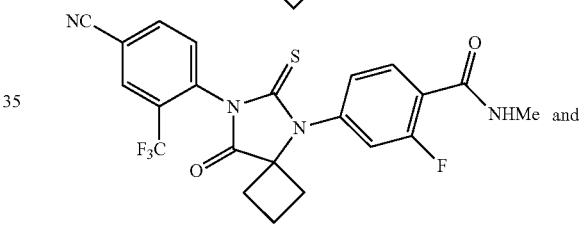

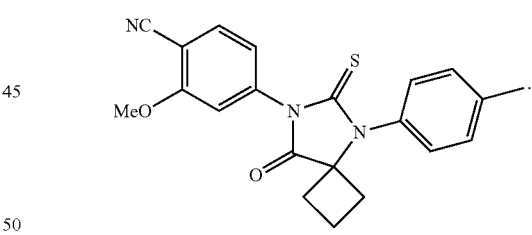

In preferred embodiments, R' is methyl, CF$_3$ or ethyl. In certain preferred embodiments, W is oxygen. In certain embodiments, W is sulfur. In certain preferred embodiments, R$_3$ and R$_4$ and the carbon to which they are attached together form a 3-6 membered cycloalkyl ring. In other preferred embodiments, one of the carbons in the 3-6 membered cycloalkyl ring is an oxygen or nitrogen. In certain embodiments, the ring is a cyclobutyl group. In certain embodiments the ring is a cyclopentyl group. In certain embodiments the ring is a cyclohexyl group. In certain embodiments, R$_2$ is a substituted aryl group. In certain embodiments, R$_2$ is phenyl. In certain embodiments, R$_2$ is a substituted heteroaryl group.

Non-limiting examples of compounds in this embodiment of formula (II) include compounds of formula (IIA):

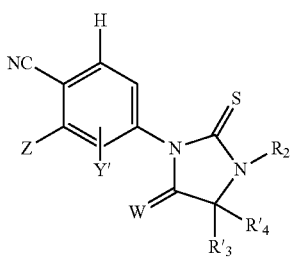

(IIA)

In compounds of formula (IIA), Y' can be alkyl such as methyl or ethyl. In other embodiments, Y' can be $CF_3$. In certain embodiments, Y' can independently be two of any of the foregoing substituents. In certain embodiments, W is oxygen. In certain embodiments, Z is hydrogen. In certain embodiments, Z is $C_1$-$C_4$ alkyl optionally substituted with one or more halogen groups, such as but not limited to methyl and ethyl. In certain embodiments, Z is $CF_3$. In certain embodiments, Z is alkoxy. In certain embodiments Z is $CF_3O$. In certain embodiments, Z is halogen. In certain embodiments, Z is cyano. In certain preferred embodiments, Z is fluoro. In certain embodiments, W is sulfur. In certain embodiments, W is two hydrogens.

In certain preferred embodiments, W is oxygen.

In certain embodiments, $R_3'$ and $R_4'$ and the carbon to which they are attached together form a 3-6 membered cycloalkyl ring in which one of the carbons is optionally an oxygen or nitrogen. In certain embodiments, the ring is a cyclopropyl group. In certain embodiments the ring is a cyclobutyl group. In certain embodiments the ring is a cyclopentyl group. In certain embodiments the ring is a cyclohexyl group. In certain embodiments, $R_3$ and $R_4$ together form a 3-6 membered cycloalkyl ring in which one of the carbons is optionally substituted with one or more fluoro groups. In certain embodiments the ring is a cyclobutyl group. In certain embodiments the ring is a cyclopentyl group. In certain embodiments the ring is a cyclohexyl group. In preferred embodiments, the ring is a cyclobutyl group.

In certain embodiments, $R_2$ is an aryl group substituted with one or more $C_1$-$C_6$ alkyl, C(O)NHR", $SO_2R"$, $SO_2NHR"$, cyano, hydroxyl, alkoxy, C(S)NHR", C(O)OR", $CH_2(CH_2)_mQ$, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R"$, $SO_2NHR"$, cyano, hydroxyl, alkoxy, C(S)NHR" and C(O)OR".

In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methylphenyl, 4-cyanophenyl, 4-methylsulfonyl-phenyl, or 4-ethoxylcarbonylphenyl.

In certain embodiments, $R_2$ is a heteroaryl group substituted with one or more $C_1$-$C_6$ alkyl, C(O)NHR", $SO_2NHR"$, cyano, C(S)NHR", C(O)OR", hydroxyl, alkoxy, $CH_2(CH_2)_m$ Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R"$, $SO_2NHR"$, cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiment, $R_2$ is a substituted saturated heterocyclic group, such as but not limited to 3-piperidine, 4-piperidine, tetrahydropyrane, 3-pyrrolidine or tetrahydrofuran.

Non-limiting examples of compounds in this embodiment of formula (II) include compounds of formula (IIB):

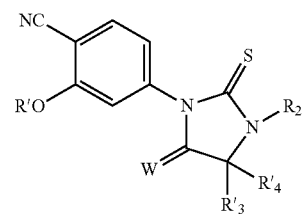

(IIB)

In compounds of formula (IIB), R' can be $C_1$-$C_3$ alkyl, such as methyl and ethyl. In other embodiments, R' can be $CF_3$.

In certain preferred embodiments, W is oxygen.

In certain embodiments, $R_3'$ and $R_4'$ and the carbon to which they are attached together form a 3-6 membered cycloalkyl ring in which one of the carbons is optionally an oxygen or nitrogen. In certain embodiments, the ring is a cyclopropyl group. In certain embodiments the ring is a cyclobutyl group. In certain embodiments the ring is a cyclopentyl group. In certain embodiments the ring is a cyclohexyl group. In certain embodiments, $R_3$ and $R_4$ together form a 3-6 membered cycloalkyl ring in which one of the carbons is optionally substituted with one or more fluoro groups. In certain embodiments the ring is a cyclobutyl group. In certain embodiments the ring is a cyclopentyl group. In certain embodiments the ring is a cyclohexyl group. In preferred embodiments, the ring is a cyclobutyl group.

In certain embodiments, $R_2$ is an aryl group substituted with one or more $C_1$-$C_6$ alkyl, C(O)NHR", $SO_2R"$, $SO_2NHR"$, cyano, hydroxyl, alkoxy, C(S)NHR", C(O)OR", $CH_2(CH_2)_mQ$, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R"$, $SO_2NHR"$, cyano, hydroxyl, alkoxy, C(S)NHR" and C(O)OR".

In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methylphenyl, 4-cyanophenyl, 4-methylsulfonyl-phenyl, or 4-ethoxylcarbonylphenyl.

In certain embodiments, $R_2$ is a heteroaryl group substituted with one or more $C_1$-$C_6$ alkyl, C(O)NHR", $SO_2NHR"$, cyano, C(S)NHR", C(O)OR", hydroxyl, alkoxy, $CH_2(CH_2)_m$ Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R"$, $SO_2NHR"$, cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiment, $R_2$ is a substituted saturated heterocyclic group, such as but not limited to 3-piperidine, 4-piperidine, tetrahydropyrane, 3-pyrrolidine or tetrahydrofuran.

Non-limiting examples of such compounds include

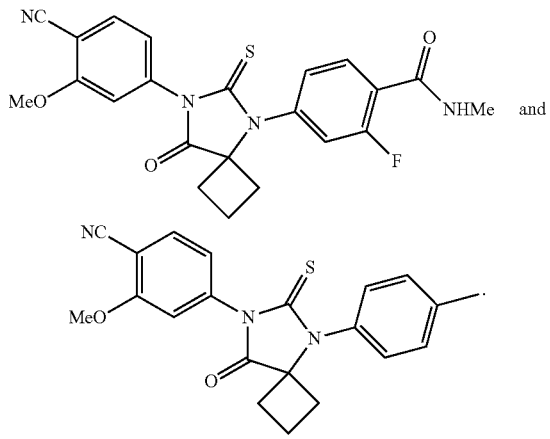

and

Non-limiting examples of compounds in this embodiment of formula (II) include compounds of formula (IIC):

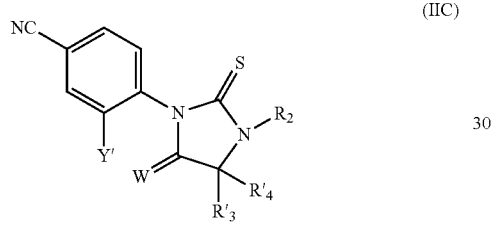

(IIC)

In compounds of formula (IIC), Y' can be alkyl such as methyl or ethyl. In other embodiments, Y' can be $CF_3$. In certain embodiments, Y' can independently be two or three of any of the foregoing substituents.

In certain preferred embodiments, W is oxygen.

In certain embodiments, $R_3$' and $R_4$' and the carbon to which they are attached together form a 3-6 membered cycloalkyl ring in which one of the carbons is optionally an oxygen or nitrogen. In certain embodiments, $R_3$' and $R_4$' together form a 3-6 membered cycloalkyl ring in which one of the carbons is optionally an oxygen or nitrogen and one of the carbons is optionally a substituted with one or more fluoro or hydroxy groups. In certain embodiments, the ring is a cyclopropyl group. In certain embodiments the ring is a cyclobutyl group. In certain embodiments the ring is a cyclopentyl group. In certain embodiments the ring is a cyclohexyl group. In certain embodiments, $R_3$ and $R_4$ together form a 3-6 membered cycloalkyl ring in which one of the carbons is optionally substituted with one or more fluoro groups. In certain embodiments the ring is a cyclobutyl group. In certain embodiments the ring is a cyclopentyl group. In certain embodiments the ring is a cyclohexyl group. In preferred embodiments, the ring is a cyclobutyl group.

In certain embodiments, $R_2$ is an aryl group substituted with one or more $C_1$-$C_6$ alkyl, C(O)NHR", $SO_2R$", $SO_2NHR$", cyano, hydroxyl, alkoxy, C(S)NHR", C(O)OR", $CH_2(CH_2)_mQ$, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R$", $SO_2NHR$", cyano, hydroxyl, alkoxy, C(S)NHR" and C(O)OR".

In certain embodiments, $R_2$ is a substituted phenyl or naphthyl group. In certain embodiments, $R_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments, $R_2$ is a heteroaryl group substituted with one or more $C_1$-$C_6$ alkyl, C(O)NHR", $SO_2NHR$", cyano, C(S)NHR", C(O)OR", hydroxyl, alkoxy, $CH_2(CH_2)_m$ Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R$", $SO_2NHR$", cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiment, $R_2$ is a substituted saturated heterocyclic group, such as but not limited to 3-piperidine, 4-piperidine, tetrahydropyrane, 3-pyrrolidine or tetrahydrofuran.

Non-limiting examples of compounds in this embodiment of formula (IIC) include:

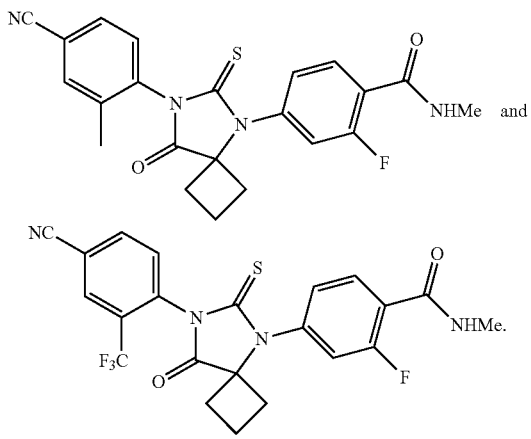

and

In certain embodiments, the present invention defines particular classes of compounds of formula (I) that are of special interest, referred to above as formula (III):

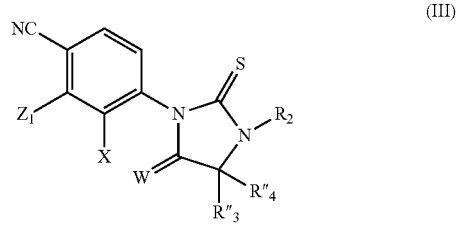

(III)

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, alkoxy, $CF_3O$, hydroxyl and cyano;

W is selected from oxygen, sulfur and two hydrogens;

R"$_3$ and R"$_4$ are methyl, or R"$_3$ and R"$_4$ and the carbon to which they are attached together form a 3-6 membered alkyl ring which may be optionally substituted with one or more fluoro or hydroxyl groups; and $R_2$ is a substituted or unsubstituted alkyl, aryl, heteroaryl or heterocyclic group.

In certain embodiments, $Z_1$ is methyl, $CH_2F$, $CHF_2$, $CF_3$, methoxy, halogen and cyano.

In certain embodiments, X is halogen.

In certain embodiments, $R_2$ is a phenyl or naphthyl group. In certain embodiments, $R_2$ is an aryl group substituted with one or more $C_1$-$C_6$ alkyl, C(O)NHR", $SO_2$R", $SO_2$NHR", cyano, hydroxyl, alkoxy, C(S)NHR", C(O)OR", $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR".

In certain embodiments, $R_2$ is 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

In certain embodiments $R_2$ is an unsubstituted heteroaryl group. In certain embodiments $R_2$ is a pyridyl group. In certain embodiments, $R_2$ is a heteroaryl group substituted with one or more $C_1$-$C_6$ alkyl, C(O)NHR", $SO_2$NHR", cyano, C(S)NHR", C(O)OR", hydroxyl, alkoxy, $CH_2(CH_2)_m$Q, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2$R", $SO_2$NHR", cyano, hydroxyl, alkoxy, C(S)NHR" and C(O)OR". In certain embodiments, $R_2$ is a substituted pyridyl group. In certain embodiments, $R_2$ is 6-methyl-pyridin-3-yl.

In certain embodiments, $R_2$ is a substituted alkyl group. In certain embodiments, $R_2$ is a substituted saturated heterocyclic group. In certain embodiments, $R_2$ is a substituted saturated heterocycle, such as but not limited to 3-piperidine, 4-piperidine, tetrahydropyrane, 3-pyrrolidine or tetrahydrofuran.

In certain embodiments, $R'_3$ and $R'_4$ and the carbon to which they are attached together form a cyclopropyl, cyclobutyl, cyclopentyl, or cyclohexyl ring which may be optionally substituted with one or more fluoro or hydroxyl groups.

In certain embodiments, $R_2$ is a substituted saturated heterocycle, such as but not limited to 3-piperidine, 4-piperidine, tetrahydropyrane, 3-pyrrolidine or tetrahydrofuran.

Non-limiting examples of compounds of formula (III) include

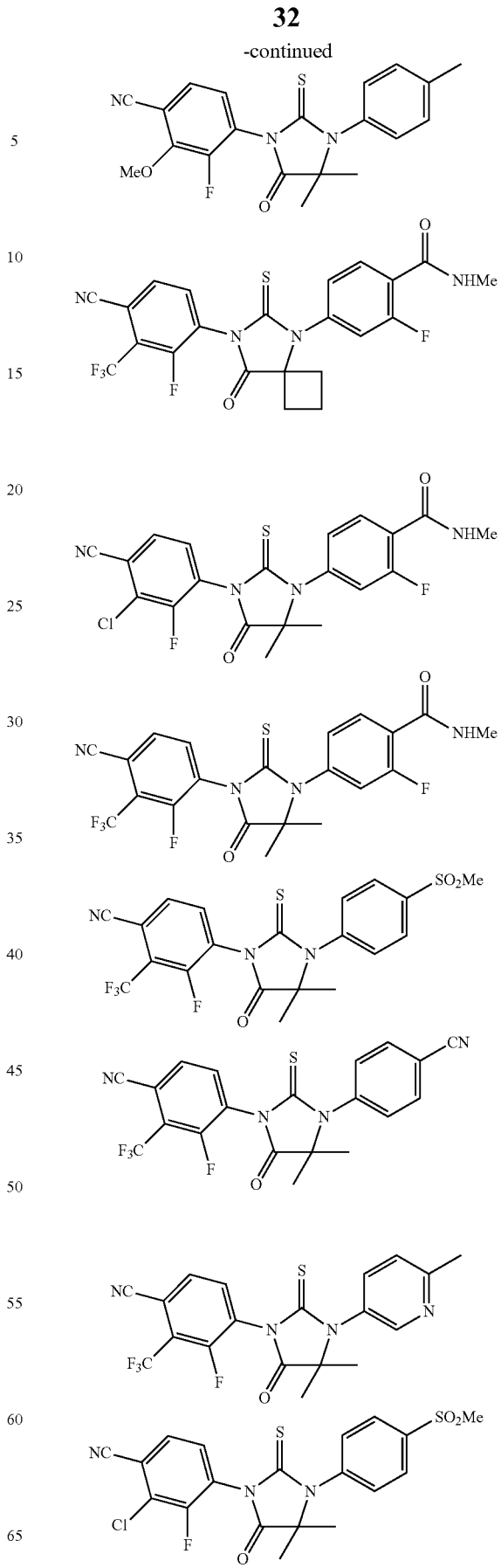

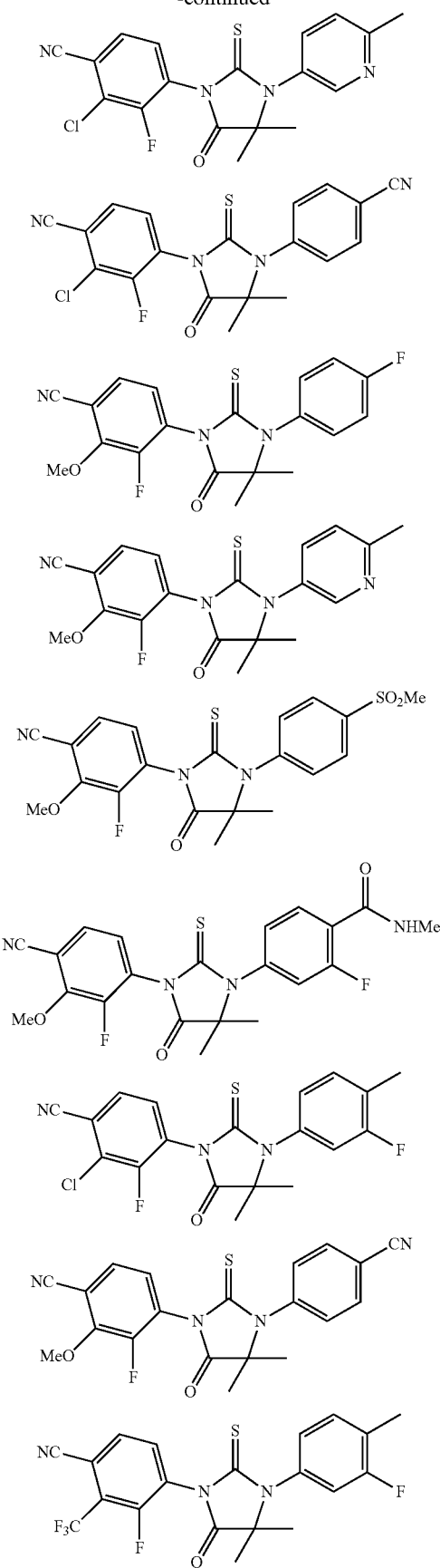

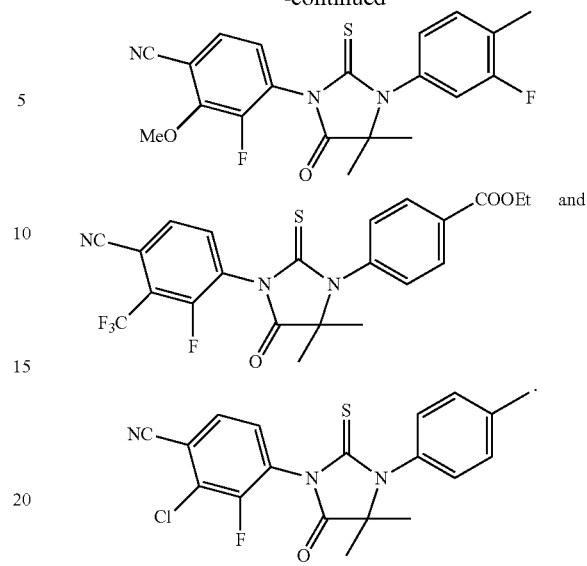

In certain embodiments, the present invention defines particular classes of compounds of formula (I) that are of special interest, referred to above as formula (IV):

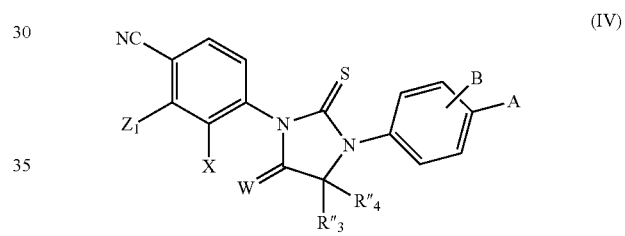

or a pharmaceutically-acceptable salt, solvate, hydrate, prodrug or derivative thereof, wherein $Z_1$ is selected from $CF_3O$, methyl, $CH_2F$, $CHF_2$, $CF_3$, methoxy, halogen and cyano;

X is selected from halogen, alkoxy, $CF_3O$, hydroxyl and cyano;

W is selected from oxygen, sulfur and two hydrogens;

$R''_3$ and $R''_4$ are methyl, or $R''_3$ and $R''_4$ and the carbon to which they are attached together form a 3-6 membered cycloalkyl ring optionally substituted with one or more fluoro or hydroxyl groups;

B is independently selected from one or more hydrogen, cyano, methyl, $CF_3$ or halogen; and A is selected from $C_1$-$C_6$ alkyl, C(O)NHR", $SO_2R''$, $SO_2NHR''$, cyano, hydroxyl, alkoxy, C(S)NHR", C(O)OR", $CH_2(CH_2)_mQ$, halogen and a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R''$, $SO_2NHR''$, cyano, hydroxyl, alkoxy, C(S)NHR" and C(O)OR".

In certain embodiments, $Z_1$ is methyl, $CH_2F$, $CHF_2$, $CF_3$, methoxy, halogen or cyano.

In certain embodiments, X is halogen.

In certain embodiments, W is oxygen.

In certain embodiments, $R''_3$ and $R''_4$ are methyl, or $R''_3$ and $R''_4$ and the carbon to which they are attached together form a cyclopropyl or cyclobutyl or cyclopentyl or cyclohexyl ring which may be optionally substituted with one or more fluoro or hydroxyl groups.

In certain embodiments, B is independently one or more hydrogen, cyano, methyl, $CF_3$ or halogen. In certain embodiments, B is hydrogen. In certain embodiment B is cyano. In certain embodiments, B is methyl. In certain embodiments B is $CF_3$. In certain embodiments, B is halogen.

In certain embodiments, A is methyl, ethyl, halogen, C(O)NHCH$_3$, C(O)NH$_2$, cyano, methoxy, ethoxy, SO$_2$Me, SO$_2$NH$_2$CH$_3$ or SO$_2$NH$_2$.

In certain embodiments, A and B taken together with the phenyl group to which they are attached is 4-fluorophenyl, 2-fluoro-4-methylamido-phenyl, 4-tolyl, 3-fluoro-4-methylphenyl, 4-cyanophenyl, 4-methylsulfonyl-phenyl, or 4-ethoxylcarbonylphenyl.

In certain preferred embodiments, $Z_1$ is $CF_3$. In certain preferred embodiments, X is fluoro. In certain preferred embodiments, W is oxygen. In certain preferred embodiments, $R_3$" and $R_4$" are both methyls. In preferred embodiments, $R_3$" and $R_4$" and the carbon to which they are attached together is a cyclobutyl group. In certain preferred embodiments, A is CONHMe, methyl, CN, or COOEt. In certain embodiments, B is a fluoro group adjacent to the A group.

Non-limiting examples of the compounds of formula (IV) include:

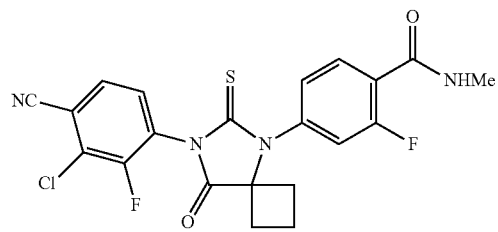

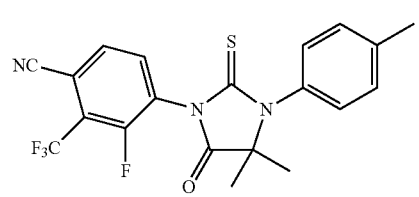

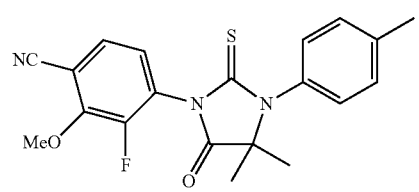

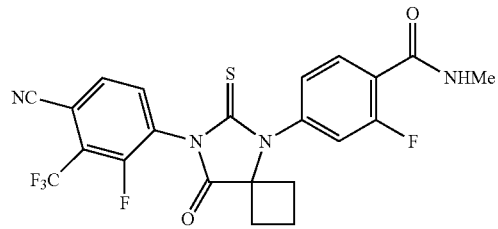

-continued

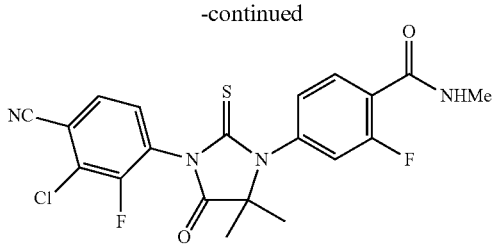

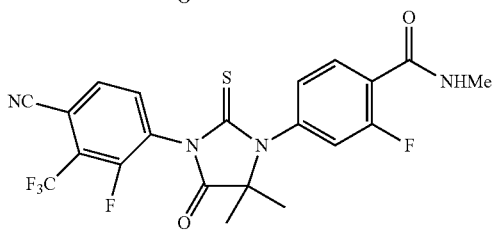

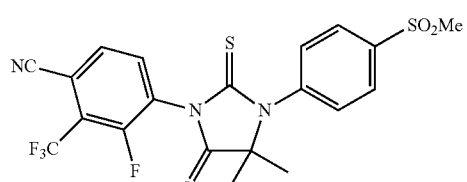

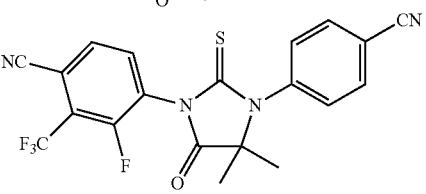

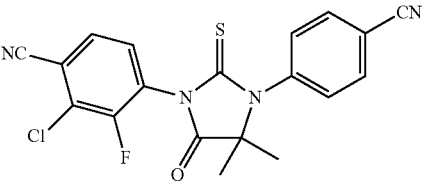

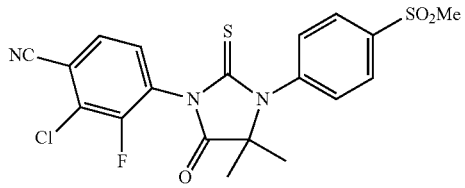

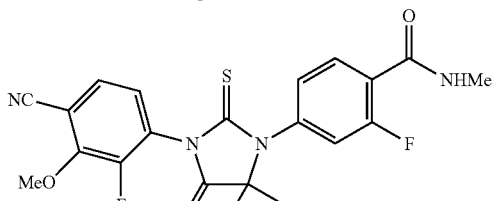

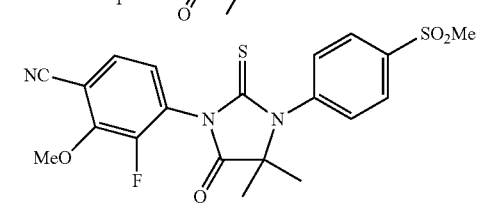

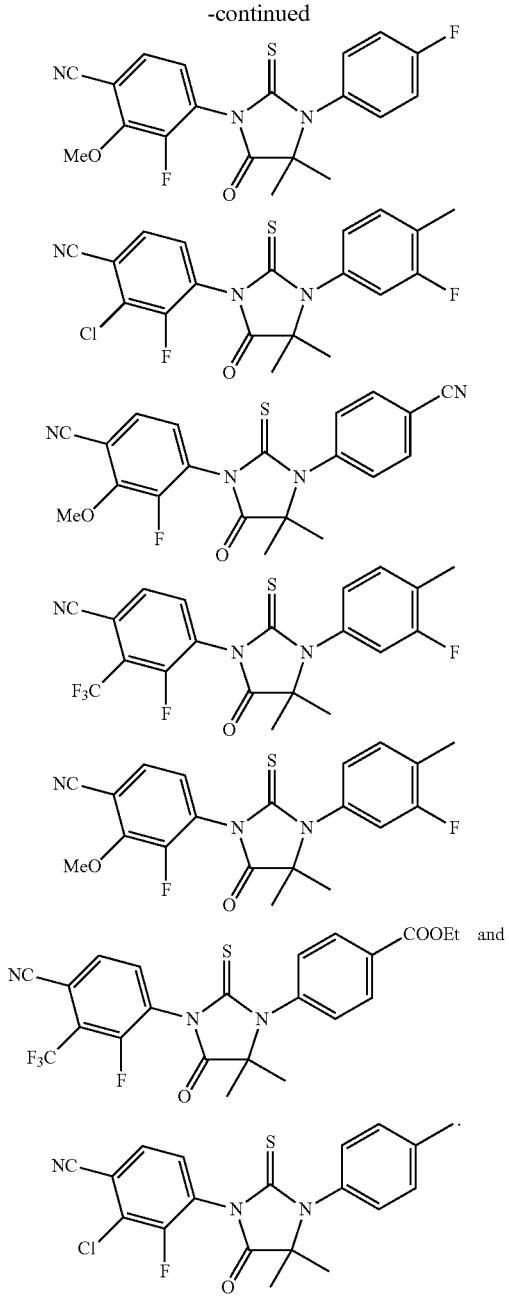

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers.

In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I), (II), (III) and (IV) under different conditions and may exist as one or a combination of polymorphs of compound of general formula (I), (II), (III) and (IV) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their pharmaceutically acceptable salts their pharmaceutically acceptable solvates and pharmaceutically acceptable compositions containing them.

2) Pharmaceutical Compositions

In another embodiment, the invention is directed to a pharmaceutical composition comprising a compound of formulas (I)-(IV) or its pharmaceutically acceptable salt, prodrug or a solution thereof as an active ingredient.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to androgen receptor activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "prodrugs" or "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed herein may achieve a desired effect for the particular disorder, for example, directly increasing hair growth or killing prostate cancer cells; or they may achieve indirect effects that still benefit the particular disorder or the treatment thereof (e.g., reduction of any adverse effects, different dosing schedule, different route of administration). In non-limiting examples, one or more compounds of the invention may be formulated with at least another biological, such as Sipuleucel-T (PROVENGE®), or with at least another small molecule compound. Non-limiting examples of pharmaceutical agents that may be combined therapeutically with compounds of the invention include: HT agents such as LUPRON®, DEGARELIX® and ABIRATERONE®; inhibitors of oncogenic kinases, e.g., VEGF, mTOR, EGFR, SRC and PI3K; cancer chemotherapy agents such as taxanes, etoposide, estramustine phosphate, and doxorubicin; HSP90 inhibitors; agents or natural extracts known to promote hairgrowth; agents or natural extracts known to treat acne; or agents or natural extracts known to treat hirsutism.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and antisickness drugs.

3) Methods of Use

As noted above, the selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; preventing the symptoms associated with reduced testosterone such as hot flashes after castration; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Prostate cancer as noted above is one of the most common cancers in men around the world, and is one of the leading causes of cancer death in men in the United States. The androgen receptor antagonist drugs, such as flutamide and bicalutamide, were originally designed to avoid the side effects of HT but androgen agonism was observed for hydroxyfluamide (the active form of flutamide) and bicalutamide. The present invention addresses the significant medical need for better androgen receptor antagonists that have potent antagonism but devoid of any agonism, and a reduction in the observed side effects such as liver toxicity found in existing androgen receptor antagonist drugs. Compounds of the invention offer a solution to this need.

In addition to prostate cancer, several other conditions and diseases are amenable to treatment with an AR antagonist. The compounds of the present invention are androgen receptor antagonists, which can be used to alleviate any condition associated with inappropriate activation of the androgen receptor. In addition to prostate cancer, other examples of such conditions include acne, hirsutism, seborrhoea, excess sebum, and alopecia. In order to exhibit the therapeutic properties described above, the compounds need to be administered in a quantity sufficient to inhibit activation of the androgen receptor. In a typical embodiment, the compounds are administered topically, which is especially appropriate for hirsutism, alopecia, acne and hyperseborrhea. Androgens, having a profound effect on hair loss, stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. The compounds may also be used topically to decrease seborrhea production and more specifically to alleviate hyperseborrhoea (oily skin), which can be used topically alleviate acne. In further embodiments, the invention comprises a method of administering such compounds of formulas (I)-(IV) or pharmaceutical compositions thereof for treating a disease or disorder related to androgen receptor activity, by way of non-limiting example, treating hormone sensitive prostate cancer or hormone refractory prostate cancer, treating benign hyperplasia of the prostate, treating acne, treating hirsutism, treating excess sebum and treating alopecia due to an androgen receptor disorder.

The compounds of present invention are antagonist of the androgen receptor. The preferred compounds have potent antagonistic potent ($IC_{50}$<1 µM) without any significant agonism activity. The compounds of the present invention can be used alone or in combination with one or more other therapeutic agent(s).

As will be seen in the examples below, the biological activity of the compounds embodied herein were tested on hormone sensitive (LNCaP, LAPC4) and hormone refractory prostate cancer cells (LNCaP-AR, LAPC4-AR, LNCaP C4-2, 22RV1, LNCaP-AI and LNCaP-ab1) to determine their antagonistic and agonistic activities. Prostate specific antigen (PSA) level can also be used as a marker for androgen receptor antagonistic activity. The MTS (4,5-dimethylthiazol-2-yl)-5-(3-carboxymethoxyphenyl)-2-(4-sulfophenyl)-2H-tetrazolium) assay is also used to evaluate the present compounds for potency of inhibiting cell growth. The selective, potent androgen receptor antagonists with acceptable rodent oral exposure are further evaluated for in vivo efficacy using prostate cancer xenografts. The cell lines can be selected from LNCaP, LAPC4, LAPC9, CWR22, LNCaP-AR, LNCaP C4-2, 22RV1, LNCaP-ab1 and LNCaP-AI.

As will also be seen in the examples, below, the PSA Assay (Inhibition Test of the Compound of the Present Invention on Prostate-specific Antigen (PSA) Production in Various Prostate Cancer Cells) demonstrated that while bicalutamide at 1 micromolar inhibited PSA production in LNCaP cells by 34%, the compounds of the invention inhibited PSA production by 91-98%; and in 22RV1 cells, 18% vs. 48-85%, respectively. Thus, the compounds of the present invention showed a strong PSA production suppressing activity in both hormone sensitive and hormone refractory cells, as compared with bicalutamide.

In another assay of the biological activity of the compounds embodied herein measuring cell viability, LNCaP and 22RV1 cells are used. As seen in the examples, while bicalutamide at 2.5 micromolar inhibited viability of LNCaP cells by 21%, compounds of the invention inhibited viability by 65-91%; inhibition of 22RV1 cells was <10%, and 31-69%, respectively. Thus, the compounds of the present invention showed stronger inhibitory activity against both hormone sensitive and hormone refractory cells, as compared with bicalutamide.

In an in vivo assay for the activity of the compounds embodied herein, a C57BL/6 mouse hair growth model was used. Solutions containing test compounds at various concentrations were topically applied to the shaved lower back. The treatment regiment regimen was twice daily (BID) application for 4 weeks. Local irritation was recorded before each application and hair growth scores were recorded every other day. After 4 weeks of treatment, mice were further observed for one more week during which hair growth and skin irritation were scored every other day. A scale was used for scoring hair growth. The results of the study showed that compounds of the invention demonstrated remarkable in vivo activity for stimulating hair growth and possessed desirable physiochemical properties for dermal delivery, indicating the compounds of the present invention are expected to be excellent therapeutics for promoting hair growth and/or other clinical indication such as reducing oily skin due to their desirable local biological effect against androgen receptor and result in low systemic exposure to avoid unwanted side effects.

As detailed in the exemplification herein, in assays to determine the ability of compounds to inhibit production of PSA by prostate cancer cells, certain inventive compounds exhibited IC50 values ≤5 µM. In certain other embodiments, inventive compounds exhibit IC50 values ≤2.5 µM. In certain embodiments, inventive compounds exhibit IC50 values ≤1 µM. In certain other embodiments, inventive compounds exhibit IC50 values ≤750 nM. In certain other embodiments, inventive compounds exhibit IC50 values ≤500 nM. In certain other embodiments, inventive compounds exhibit IC50 values ≤250 nM. In certain other embodiments, inventive compounds exhibit IC50 values ≤100 nM. In other embodiments, exemplary compounds exhibit IC50 values ≤75 nM. In other embodiments, exemplary compounds exhibit IC50 values ≤50 nM. In other embodiments, exemplary compounds exhibit IC50 values ≤40 nM. In other embodiments, exemplary compounds exhibit IC50 values ≤30 nM. In other embodiments, exemplary compounds exhibit IC50 values ≤20 nM. In other embodiments, exemplary compounds exhibit IC50 values ≤10 nM. In other embodiments, exemplary compounds exhibit IC50 values ≤5 nM.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules, or topical forms. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/ or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols. 1-17, John Wiley and Sons, New York, N.Y., 1991; Rodd 1989 "Chemistry of Carbon Compounds", vols. 1-5 and supps., Elsevier Science Publishers, 1989; "Organic Reactions", vols. 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2nd ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

EXAMPLES

Synthetic Examples

Synthesis of Compounds of the Invention

The compounds of formula I-IV of the invention can be prepared as shown in the following reaction schemes (using formula I as an example) and description thereof.

Scheme 1

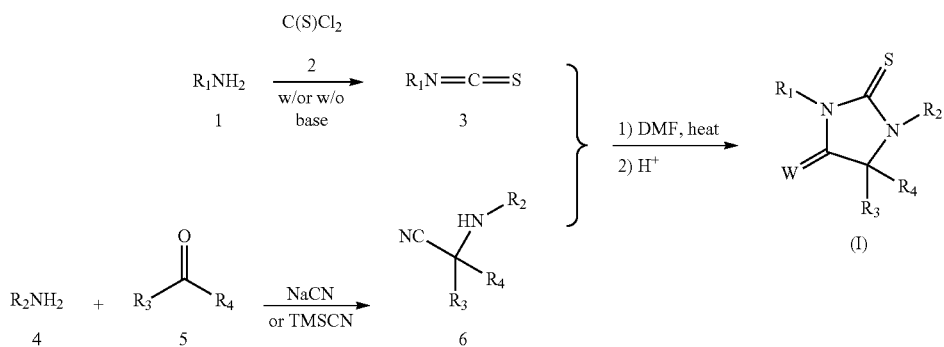

As shown in Scheme 1, isothiocyanate 3 can be prepared from aniline 1 with treatment of thiophosgene. Intermediate 6 can be synthesized by condensing amine or aniline 4 and ketone 5 in the presence of TMSCN or sodium cyanide. The condensation can also be accomplished by reacting the aniline 4 and an appropriate ketone cyanoanhydrin in the presence of $MgSO_4$. The final thioimidazolidinone, compound of formula I, can be prepared from reaction between 3 and 6. Aniline 1 can be obtained commercially, or can be prepared by methods shown below or known in the literature, for example, reduction of nitrobenzenes.

Synthesis of isothiocyanate 3a

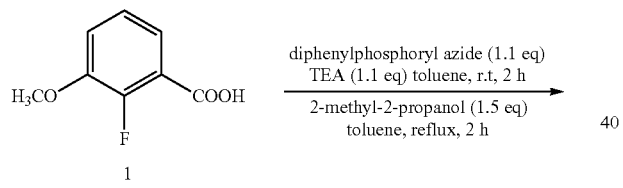

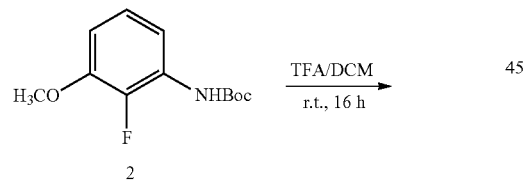

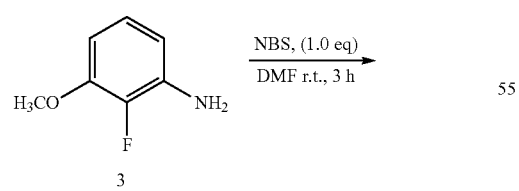

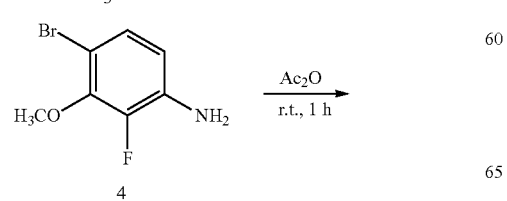

-continued

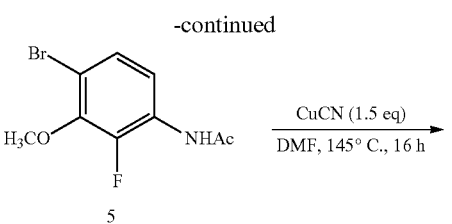

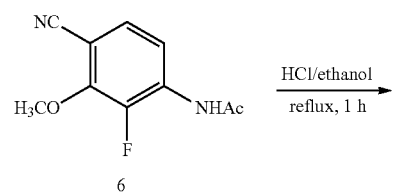

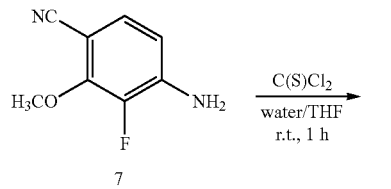

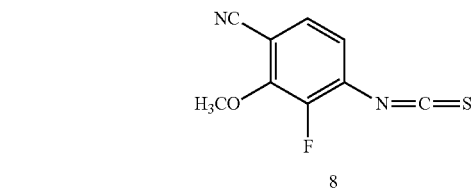

Preparation of Compound 8

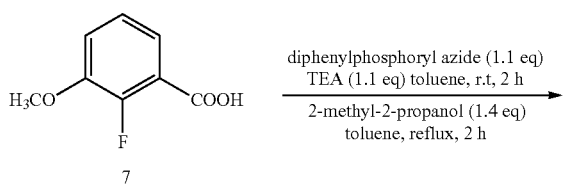

-continued

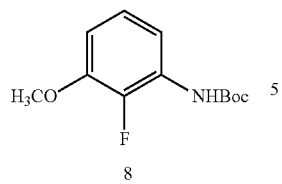
8

To a solution of compound 7 (7.5 g, 44 mmol) in toluene (150 ml), TEA (7 mL, 48 mmol, 1.1 eq) was added, followed by DPPA (10.5 mL, 48.4 mmol, 1.1 eq). The reaction mixture was stirred at room temperature for 2 h. 2-Methyl-2-propanol (6.3 mL, 66 mmol, 1.5 eq) was then added and the resulting mixture was heated at reflux for 2 h. Solvent was removed in vacuo and the residue was diluted with ethyl acetate (200 mL), washed with water (1×50 mL). The organic layer was dried ($Na_2SO_4$), filtered, and concentrated to give the title compound (8) as a light yellow solid (8.9 g, 90% yield), which was used directly in the next step without further purification. ESI-MS $(M-C_4H_9)^+$: 186.

Preparation of Compound 9

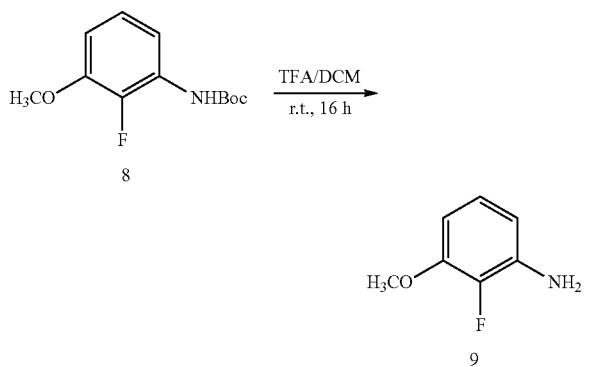

To a compound 8 (24 g, 100 mmol) solution in dichloromethane (100 mL) was slowly added TFA (40 mL) at 0° C. The reaction mixture was stirred at room temperature overnight, then extracted with $H_2O$ (2×300 mL). The aqueous phase was neutralized by addition of saturated $NaHCO_3$ aqueous solution until pH=8, then extracted with ethyl acetate (3×100 mL). The combined organic layers were dried ($Na_2SO_4$), filtered, and concentrated to give the title compound (9) as a brown liquid (13 g, 92% yield). ESI-MS $(M-C_4H_9)^+$: 142

Preparation of Compound 10

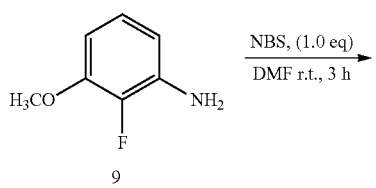
9

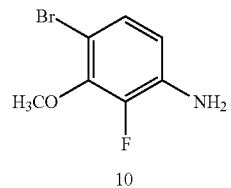
10

To a solution of compound 9 (13 g, 92 mmol) in DMF (100 mL) was added a solution of NBS (16.4 g, 92 mmol, 1.0 eq) in DMF (100 mL) drop-wise. The reaction mixture was stirred at room temperature for 3 h, then diluted with ethyl acetate (500 mL) and washed with brine (2×150 mL). The organic phase was dried ($Na_2SO_4$), filtered and concentrated to give the title compound (10) as brown oil (23 g, 98% yield). ESI-MS $(M+H)^+$: 219.9.

Preparation of Compound 11

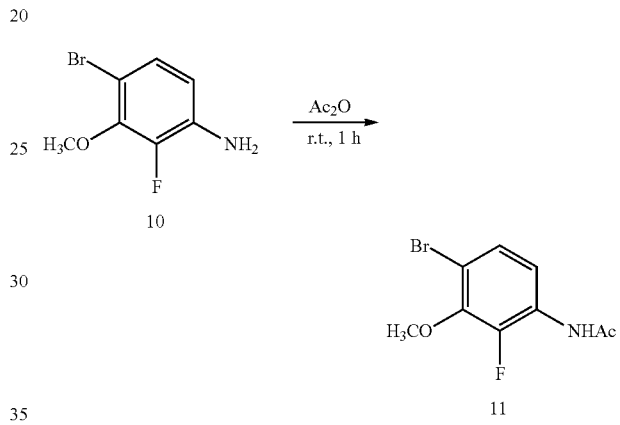

Compound 10 (11.2 g, 51 mmol) was dissolved in 10 ml of $Ac_2O$ and stirred at room temperature for 1 h. The solution was concentrated in vacuo and the residue was added ice (~10 g) and sodium bicarbonate (until pH=7). The resulted mixture was extracted with ethyl acetate (3×100 mL). The organic layers were combined, dried ($Na_2SO_4$), filtered and concentrated to give the title compound (II) as a brown solid (9.8 g, 74% yield). $^1$H NMR (400 MHz, $CDCl_3$) δ 7.94-7.91 (m, 1H), 7.55 (br, 1H), 7.28-7.26 (m, 1H), 3.93 (s, 3H), 2.08 (s, 3H); ESI-MS $(M+H)^+$: 263.9.

Preparation of Compound 12

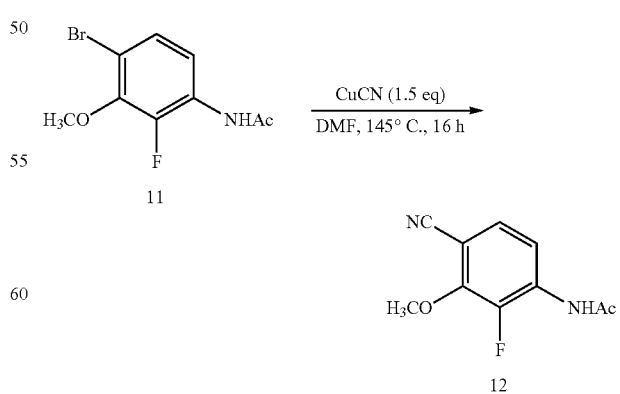

A mixture of compound 11 (5.0 g, 19 mmol) and CuCN (2.5 g, 29 mmol, 1.5 eq) in DMF (20 mL) was heated at 145°

C. under nitrogen overnight. The reaction mixture was cooled to room temperature and then poured into ice water (50 mL). Ethyl acetate (100 mL) was added and the insoluble solid was filtered off (washed with ethyl acetate [2×30 mL]). The organic layer was separated, and the aqueous layer was extracted with ethyl acetate (2×50 mL). The combined extracts were washed with saturated aqueous NaHCO$_3$ solution (1×150 mL), brine (3×100 mL), and dried over MgSO$_4$. The resulting material was concentrated and the residue was purified by silica gel chromatography (petroleum ether:ethyl acetate, 10:1) to afford the title compound (12) as a light yellow solid (2.6 g 66% yield). $^1$H NMR (400 MHz, DMSO-d$_6$) δ 10.13 (s, 1H), 7.93 (d, 1H), 7.53 (d, 1H), 4.05 (s, 3H), 2.15 (s, 3H); ESI-MS (M+H)$^+$: 209.

Preparation of Compound 1a

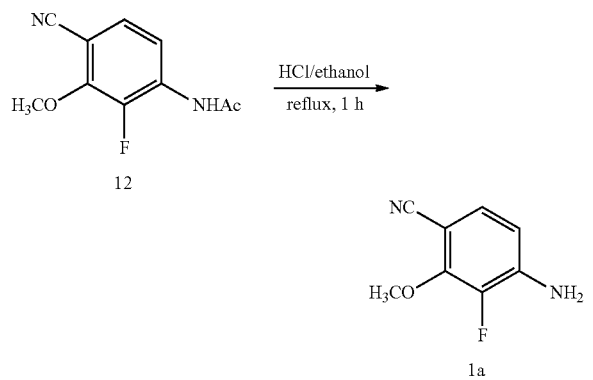

To a solution of compound 12 (4.0 g, 192 mmol) in ethanol (30 mL), was added concentrated HCl solution (12N, 10 mL). The mixture was heated at reflux for 1 h. Solvent was removed in vacuo. The residue was re-dissolved in water (50 mL). The resulting aqueous solution was added saturated NaHCO$_3$ aqueous solution until pH=7~8, then extracted with ethyl acetate (3×150 mL). The combined organic layers were dried with Na$_2$SO$_4$, filtered, and concentrated to provide the title compound (1a) as a light yellow solid (3.2 g, 90% yield). $^1$H NMR (400 MHz, DMSO-d$_6$) δ 7.18 (d, 1H), 6.50 (t, 1H), 6.28 (s, 2H), 3.97 (s, 3H); ESI-MS (M+H)$^+$: 167.

Preparation of Compound 3a

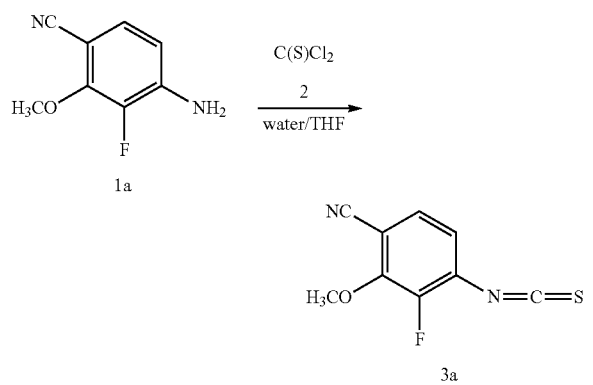

To a solution of 1a (332 mg, 2 mmol) in THF (5 mL), a solution of thiophosgene (2 mL) in water (5 mL) was slowly added at room temperature. The reaction mixture was stirred for 1 h then concentrated. The residue was partitioned between H$_2$O (50 mL) and ethyl acetate (30 mL). The resulted aqueous phase was extracted with ethyl acetate (2×30 mL). The organic extracts were combined, washed with brine (2×50 mL), dried with anhydrous MgSO$_4$, filtered, and concentrated to provide the title compound (3a) as a light yellow solid, which was used directly in next step without further purification.

Synthesis of isothiocyanate 3b

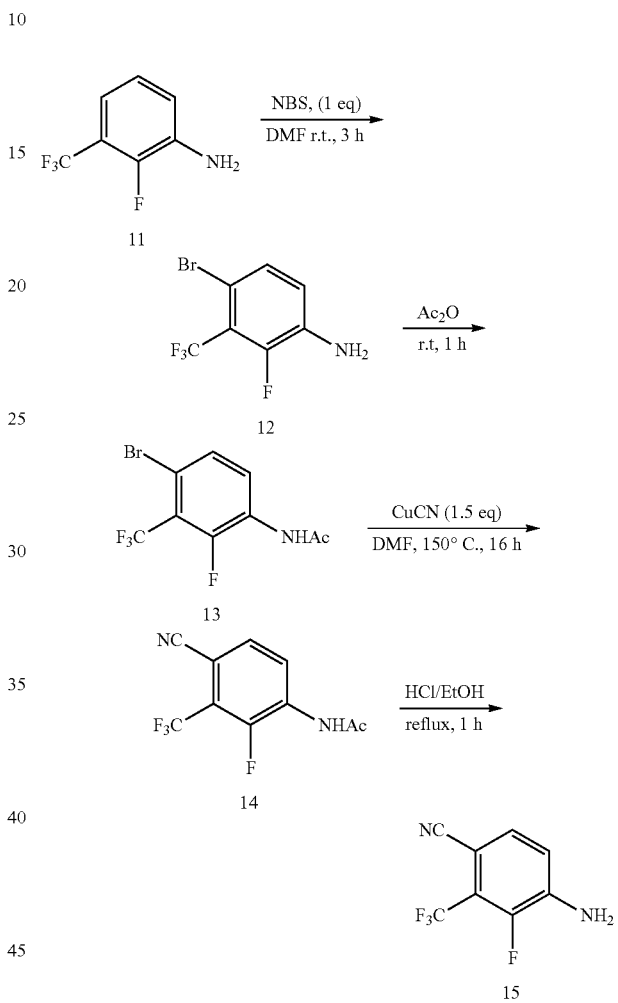

Preparation of Compound 14

To a compound 13 (2.88 g, 16.1 mmol) solution in DMF (30 mL) was added a DMF solution (30 mL) of NBS (2.86 g, 16.1 mmol) drop-wise at room temperature. After 3 h, the reaction mixture is diluted with Et$_2$O (100 mL) and washed with brine (2×100 mL). The separated organic phase was dried (Na$_2$SO$_4$) and concentrated to give the title compound (14) as an oil (3.1 g, 75% yield). $^1$H NMR (400 MHz, DMSO-d$_6$) δ 7.32 (d, 1H), 6.96 (t, 1H), 5.847 (s, 2H); ESI-MS (M+H)$^+$: 259.8.

Preparation of Compound 15

A mixture of compound 14 (2.58 g) and acetic anhydride (5 mL) was stirred at room temperature for 3 h, then concentrated in vacuo. The residue was added ice (~10 g) and sodium bicarbonate (until pH=7). The resulted mixture was extracted with ethyl acetate (3×100 mL). The organic layers were combined, dried (Na$_2$SO$_4$), filtered and concentrated to give the title compound (15). (2.68 g, 85% yield). ESI-MS (M+H)$^+$: 301.8.

Preparation of Compound 16

A mixture of compound 15 (1.5 g, 5 mmol), CuCN (0.72 g, 6 mmol) in DMF (8 ml) was heated at 145° C. under nitrogen overnight. The reaction mixture was cooled to room temperature and then poured into ice water (25 mL). Ethyl acetate (30 mL) was added and the insoluble solid was filtered off [rinsed with ethyl acetate (3×10 mL)]. The organic layer was separated, and the aqueous layer was extracted with ethyl acetate (1×50 mL). The combined extracts were washed with saturated aqueous $NaHCO_3$ (2×50 mL), brine (3×50 mL), dried over $MgSO_4$, filtered and concentrated in vacuo. The residue was purified with silica gel chromatography (10:1/Petroleum ether:ethyl acetate) to afford the title compound (16) as a light yellow solid (1.1 g, 80% yield). ESI-MS (M+H)$^+$: 246.9.

Preparation of Compound 1b

To a solution of compound 16 (1.45 g, 5.89 mmol) in EtOH (10 mL) was added concentrated HCl solution (12N, 10 mL). The mixture was heated at reflux for 1 h, cooled to room temperature, then concentrated in vacuo. The resulting white solid was dissolved in ethyl acetate (25 mL), washed with saturated aqueous $NaHCO_3$ (1×25 mL), dried over $MgSO_4$ and concentrated to give compound 1b (1.0 g, 90% yield) as a white solid. ESI-MS (M+H)$^+$: 205.

Preparation of Compound 3b

Synthesis of compound 3b from 1b followed a procedure similar to the preparation of 3a. The title compound 3b was obtained in 95% yield.

Synthesis of isothiocyanate 3c

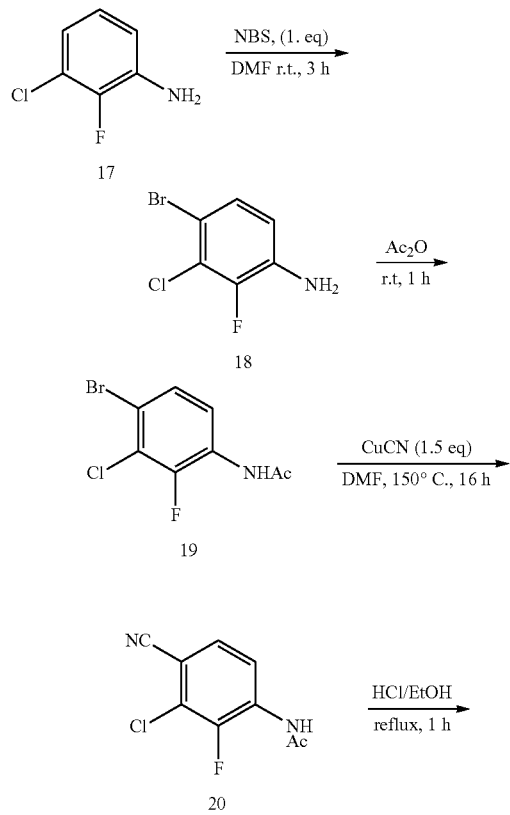

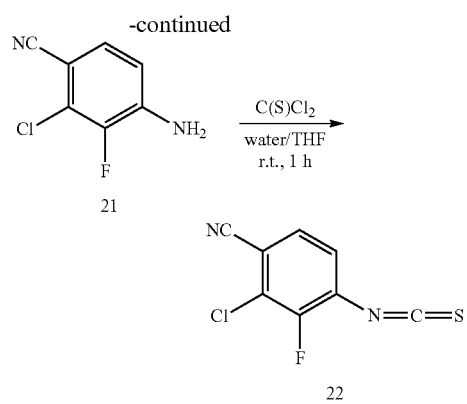

Preparation of Compound 18

A solution of compound 17 (5 g, 0.034 mol) in DMF (50 mL) was added a DMF solution (50 mL) of NBS (6.05 g, 0.034 mol) drop-wise at room temperature. After 16 h, the reaction mixture was diluted with ethyl acetate (100 mL) and washed with brine (2×100 mL). The separated organic phase was dried over $Na_2SO_4$ and concentrated to give the title compound 18 as an oil (5.0 g, 65% yield). ESI-MS (M+H)$^+$: 223.92.

Preparation of Compound 19

A mixture of compound 18 (5.0 g, 22 mmol), acetic anhydride (5 mL) and pyridine (0.1 mL) was stirred at room temperature for 50 min, then concentrated in vacuo. The residue was added ice (~10 g) and sodium bicarbonate (until pH=7). The resulted mixture was extracted with ethyl acetate (3×50 mL). The organic layers were combined, dried ($Na_2SO_4$), filtered and concentrated to give the title compound 19. (4.0 g, 68% yield). ESI-MS (M+H)$^+$: 265.93.

Preparation of Compound 20

A mixture of compound 19 (4.0 g, 15 mmol) and CuCN (1.59 g, 18 mmol) in DMF (40 ml) was heated at 145° C. under nitrogen atmosphere overnight. The reaction mixture was cooled to room temperature, poured into ice water (20 mL). Ethyl acetate (25 mL) was added and the insoluble solid was filtered off [rinsed with ethyl acetate (3×10 mL)]. The organic layer was separated, and the aqueous layer was extracted with ethyl acetate (1×25 mL). The combined extracts were washed with saturated aqueous $NaHCO_3$ solution (2×30 mL), brine (3×40 mL), dried ($MgSO_4$), and concentrated in vacuo. The residue was purified by silica gel chromatography (5:1/Petroleum ether:ethyl acetate) to afford the title compound 20 as a light yellow solid (2.56 g, 80% yield). ESI-MS (M+H)$^+$: 213.02

Preparation of Compound 1c

To a solution of compound 20 (2.56 g, 12 mmol) in EtOH (10 mL) was added concentrated HCl solution (12N, 10 mL). The mixture was heated at reflux for 1 h and then concentrated in vacuo. The resulting white solid was dissolved in ethyl acetate (50 mL). The solution was washed with saturated aqueous $NaHCO_3$ solution (1×50 mL), dried over $MgSO_4$ and concentrated to give the title compound 1c (1.8 g, 88% yield) as a white solid. $^1$H NMR (400 MHz, CDCl$_3$) δ 7.55 (d, J=6.0 Hz, 1H), 7.07-7.04 (m, 1H), 6.82 (br s, 2H). ESI-MS (M+H)$^+$: 171.00.

Preparation of Compound 3c

To a solution of 1c (1.8 g, 11 mmol) in THF (20 mL) was added a solution of thiophosgene (11 mL) in water (11 mL) slowly at room temperature. The reaction mixture was stirred for 1 h, then concentrated in vacuo. The residue was dissolved in H$_2$O (50 mL). The aqueous solution was extracted with ethyl acetate (3×50 mL). The organic extracts were combined and washed with brine (2×50 mL), dried with anhydrous MgSO$_4$, filtered, concentrated to provide compound the title compound 3c as a light yellow solid, which was used directly in next step without further purification.

Synthesis of Example 1

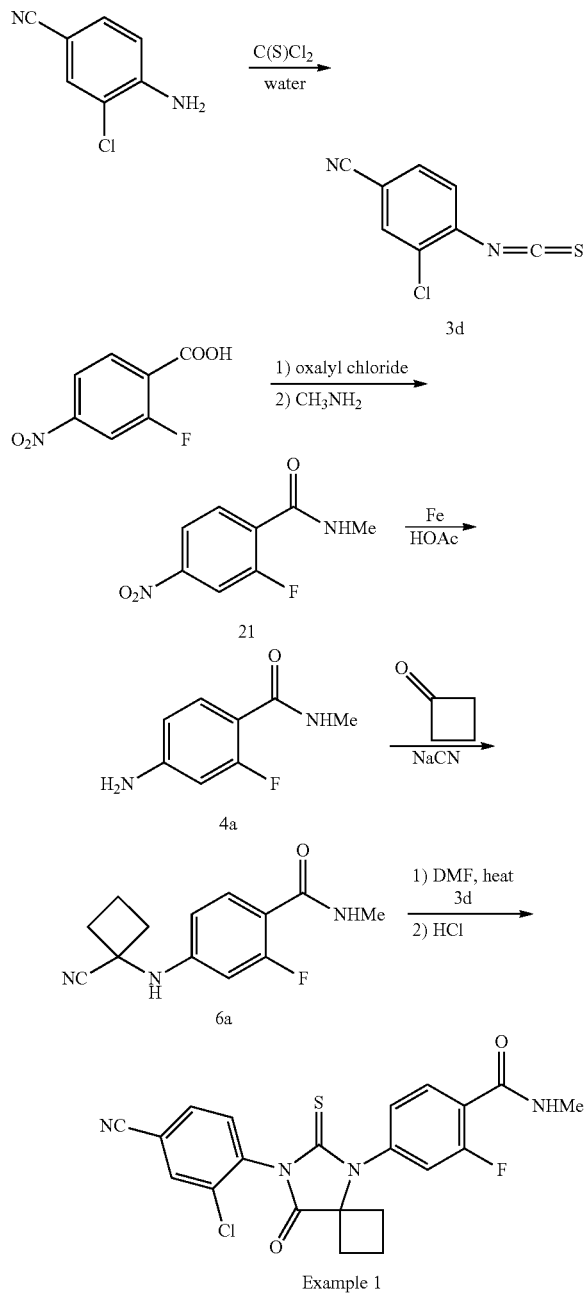

Example 1

Synthesis of 3-chloro-4-isothiocyanato-benzonitrile 3d

To a suspension of thiophosgene (2 mL) in water (5 mL) was added 4-amino-3-chloro-benzonitrile (1 g, 7 mmol) in small portions over a period of 1 h at 25° C. The mixture was extracted with ethyl acetate (3×25 mL). Combined organic phase was washed with brine (1×50 mL), dried (MgSO$_4$) and concentrated to dryness in vacuo. The title compound 3d was obtained as a tan solid (1.3 g, 96% yield).

Synthesis of 2-Fluoro-N-methyl-4-nitro-benzamide 21

Thionyl chloride (15 g, 130 mmol) was added slowly to a solution of acid 2-fluoro-4-nitro-benzoic acid (20 g, 110 mmol) in DMF (20 mL) at −5° C. The mixture was stirred for an additional 1 h at −5° C. At 0° C., a methylamine solution (2M, 400 mL, 800 mmol) in tetrahydrafuran was added dropwise to the solution. The reaction mixture was slowly warmed to 25° C. and then poured into ice-water (125 mL). The suspension was extracted with ethyl acetate (2×200 mL). Combined organic phase was washed with brine (1×200 mL), dried (MgSO$_4$) and concentrated to dryness in vacuo. The title compound 21 was obtained as a yellow solid (20 g, 90% yield). MS: 163 (M+H)$^+$. $^1$H NMR (acetone-d$_6$, 500 MHz): δ 7.66 (1H, dd, J=8.5, 8.5 Hz), 6.41 (1H, dd, J=8.6, 2.1 Hz), 6.32 (1H, dd, J=13.6, 2.0 Hz), 3.05 (3H, d, J=4.4 Hz).

Synthesis of 4-Amino-2-fluoro-N-methyl-benzamide 4a

To a solution of 2-fluoro-N-methyl-4-nitro-benzamide 21 (3 g, 15.1 mmol) in co-solvent of ethyl acetate and acetic acid (12 mL+12 mL) was added iron dust (8 g, 143. mmol). The suspension was heated at reflux until the starting material disappeared in LCMS. Cooled down to 25° C. The solid was filtered off and the filtrate was diluted with ethyl acetate (50 mL). The organic phase was washed with brine (3×30 mL), dried (MgSO$_4$) and concentrated to dryness in vacuo. The title compound 4a was obtained as an orange solid (2.5 g, 97% yield). MS: 169 (M+H)$^+$. $^1$H NMR (acetone-d$_6$, 500 MHz): δ 7.69 (1H, dd, J=8.7, 8.8 Hz), 7.15 (1H, s), 6.51 (1H, dd, J=8.6, 2.1 Hz), 6.38 (1H, dd, J=14.7, 2.1 Hz), 5.70 (1H, br s), 2.88 (3H, d, J=4.3 Hz).

Synthesis of 4-(1-Cyano-cyclobutylamino)-2-fluoro-N-methyl-benzamide 6a

TMS-CN (29.7 g, 300 mmol) was added to a mixture of N-methyl-2-fluoro-4-aminobenzamide 4a (16.8 g, 100 mmol) and cyclobutanone (14 g, 200 mmol) in 90% acetic acid (200 mL). The reaction mixture was stirred at 80° C. for 24 h. The mixture was cooled and diluted with water (200 mL). The suspension was extracted with ethyl acetate (3×200 mL). Combined organic layers were washed with brine (4×100 mL), dried (MgSO$_4$) and concentrated in vacuo to dryness. The residue was triturated with a mixed solvent of hexanes and ethylether (20 mL-20 mL) to remove cyclobutanone cyanohydrin. The solid was collected by filtration, affording the title compound 6a (20 g, 84% yield). MS (ES-API Negative): 246 (M−H)$^−$. $^1$H NMR (CDCl$_3$, 500 MHz): δ 7.92 (1H, dd, J=8.4, 8.4 Hz), 6.76 (1H, q, J=4.3 Hz), 6.48 (1H, dd, J=8.3, 1.9 Hz), 6.29 (1H, dd, J=14.3, 1.9 Hz), 4.72 (1H, br s), 2.97 (3H, d, J=4.4 Hz), 2.85-2.75 (2H, m), 2.4-2.35 (2H, m), 2.3-2.15 (1H, m), 1.95-1.85 (1H, m).

Synthesis of 4-[7-(2-Chloro-4-cyano-phenyl)-8-oxo-6-thioxo-5,7-diaza-spiro[3.4]oct-5-yl]-2-fluoro-N-methyl-benzamide (Example 1)

A mixture of 6a (388 mg, 2 mmol) and 3d (494 mg, 2 mmol) in DMF (10 mL) was heated under microwave irradiation at 110° C. for 12 h. To this mixture is added ethanol (10 mL) and HCl (2N, 5 mL). The resulting mixture was refluxed for 1 h. After being cooled to room temperature, the reaction mixture was poured into cold water and extracted with ethyl acetate (3×100 mL). Combined organic layers were dried over MgSO$_4$, concentrated. The residue was purified by silica gel column chromatography using petroleum ether:ethyl acetate (1:1), to give the title compound (Example 1, 200 mg, 23% yield). $^1$H NMR (CDCl$_3$, 500 MHz): δ 8.39 (1H, t, J=9.0 Hz), 7.89 (1H, s), 7.72 (1H, dd, m), 7.54 (1H, d, J=8.0 Hz), 7.26 (1H, m.br), 7.20 (1H, d, J=11 Hz), 6.71 (1H, br s), 3.00 (3H, d, J=5 Hz), 2.70 (2H, m), 2.52 (2H, m), 2.26 (1H, m), 1.69 (1H, m, br). MS (ES-API positive): 443 (M+H)$^+$.

Synthesis of 4-[7-(4-Cyano-3-methoxy-phenyl)-8-oxo-6-thioxo-5,7-diaza-spiro[3.4]oct-5-yl]-2-fluoro-N-methyl-benzamide (Example 2)

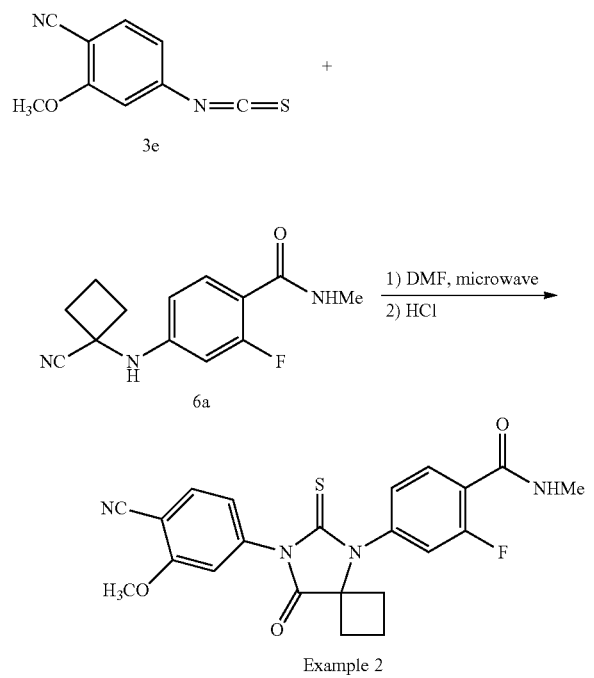

A mixture of 3e (380 mg, 2 mmol, prepared by a method similar to the synthesis of 3d) and 6a (494 mg, 2 mmol) in DMF (10 mL) was heated under microwave irradiation at 110° C. for 12 h. After cooled to room temperature, to the reaction mixture was added ethanol (10 mL) and aqueous HCl solution (2N, 5 mL). The resulting mixture was heated at reflux for 1 h. The solution was poured into ice-cold water and the mixture was extracted with ethyl acetate (3×30 mL). The organic layers were combined, dried over MgSO$_4$, and concentrated in vacuo. The residue was purified with silica gel column chromatography using Petroleum ether:Ethyl acetate (1:1), affording the title compound (Example 2, 180 mg, 20% yield). $^1$H NMR (CDCl$_3$, 500 MHz): δ 8.39 (1H, t, J=9.0 Hz), 7.62 (1H, d, J=8.0 Hz), 7.26 (1H, m.br), 7.18 (1H, d, J=10.0 Hz), 7.10 (2H, m), 6.71 (1H, br s), 3.97 (3H, s), 3.00 (3H, d, J=5 Hz), 2.70 (2H, m), 2.52 (2H, m), 2.26 (1H, m), 1.69 (1H, m, br). MS (ES-API positive): 439 (M+H)$^+$.

Synthesis of 4-[7-(4-Cyano-2,5-difluoro-phenyl)-8-oxo-6-thioxo-5,7-diaza-spiro[3.4]oct-5-yl]-2-fluoro-N-methyl-benzamide (Example 3)

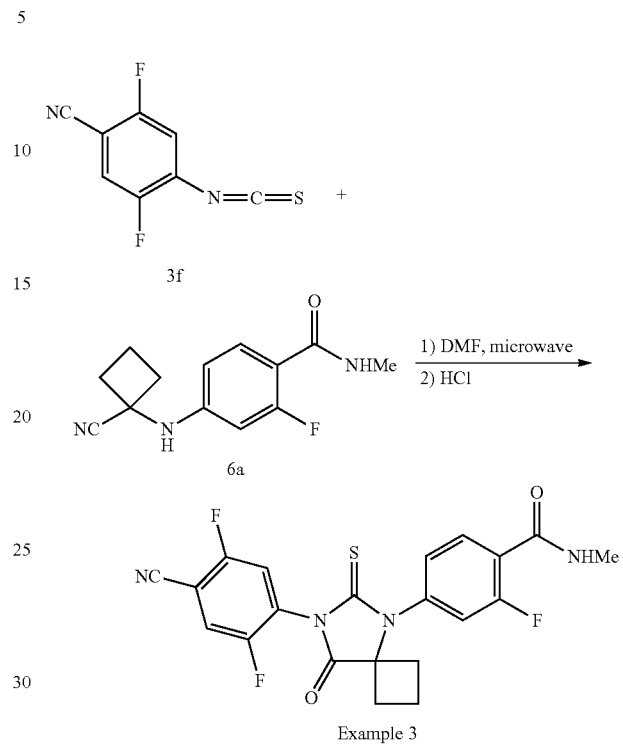

A mixture of 3f (392 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 3, 220 mg, 25% yield). $^1$H NMR (CDCl$_3$, 500 MHz): δ 8.26 (1H, dd, J=8.6, 3.5 Hz), 7.54 (1H, dd, J=8.0, 5.0 Hz), 7.40 (1H, dd, J=8.0, 6.0 Hz), 7.26 (1H, m), 7.10 (1H, dd, J=10.5, 2.0 Hz), 6.60 (1H, br s), 3.00 (3H, d, J=5 Hz), 2.7 (2H, m), 2.50 (2H, m), 2.24 (1H, m), 1.70 (1H, m). MS (ES-API positive): 445 (M+H)$^+$.

Synthesis of 4-[7-(4-Cyano-2-trifluoromethoxy-phenyl)-8-oxo-6-thioxo-5,7-diaza-spiro[3.4]oct-5-yl]-2-fluoro-N-methyl-benzamide (Example 4)

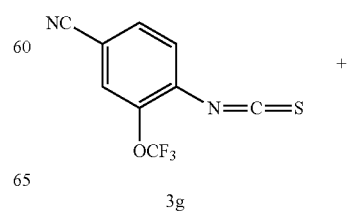

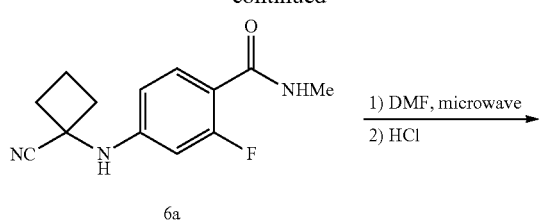

6a

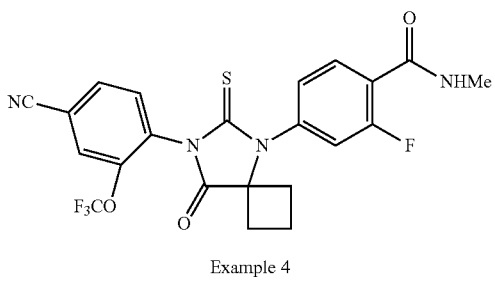

Example 4

A mixture of 3 g (488 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 4, 250 mg, 25% yield). $^1$H NMR (CDCl$_3$, 500 MHz): δ 8.30 (1H, dd, J=8.6, 3.5 Hz), 7.70 (2H, dd, J=8.0, 1.5 Hz), 7.63 (1H, d, J=8.5 Hz), 7.26 (1H, m), 7.15 (1H, dd, J=11.5, 1.5 Hz), 6.60 (1H, br s), 3.00 (3H, d, J=5 Hz), 2.65 (2H, m), 2.52 (2H, m), 2.27 (1H, m), 1.70 (1H, m). MS (ES-API positive): 493 (M+H)$^+$.

Synthesis of 4-[7-(4-Cyano-2-fluoro-phenyl)-8-oxo-6-thioxo-5,7-diaza-spiro[3.4]oct-5-yl]-2-fluoro-N-methyl-benzamide (Example 5)

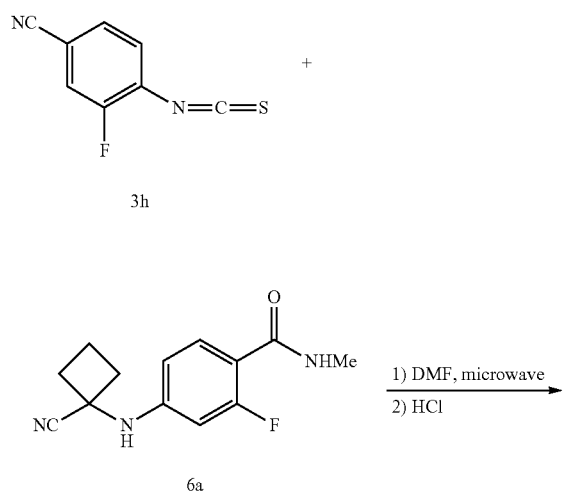

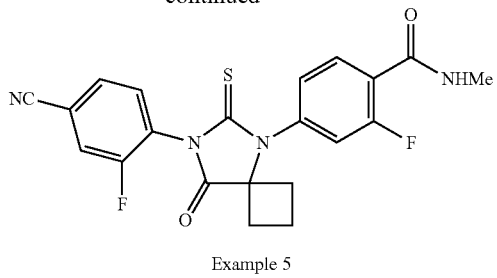

Example 5

A mixture of 3 h (356 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 5, 200 mg, 23% yield). $^1$H NMR (CDCl$_3$, 500 MHz): δ 8.30 (1H, dd, J=8.6, 3.5 Hz), 7.57 (3H, m), 7.26 (1H, m), 7.15 (1H, dd, J=12.0, 2.0 Hz), 6.71 (1H, br s), 3.00 (3H, d, J=5 Hz), 2.65 (2H, m), 2.52 (2H, m), 2.27 (1H, m), 1.70 (1H, m, br). MS (ES-API positive): 427 (M+H)$^+$.

Synthesis of 4-[7-(4-Cyano-2-methyl-phenyl)-8-oxo-6-thioxo-5,7-diaza-spiro[3.4]oct-5-yl]-2-fluoro-N-methyl-benzamide (Example 6)

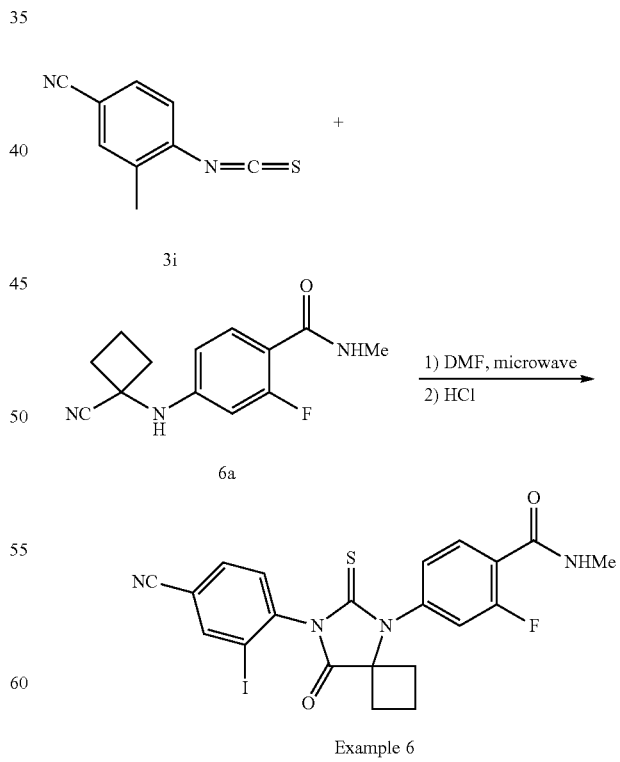

Example 6

A mixture of 3i (348 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 6, 180 mg, 21% yield). $^1$H NMR (CDCl$_3$, 500 MHz): δ 8.30 (1H, dd, J=8.6, 3.5 Hz), 7.67 (2H, m), 7.38 (1H, d, J=8.0 Hz), 7.26 (1H, m), 7.20 (1H, dd, J=11.5, 2.0 Hz), 6.71 (1H, br s), 3.00 (3H, d, J=5 Hz), 2.65 (2H, m), 2.52 (2H, m), 2.15 (3H, s), 2.15 (1H, m), 1.68 (1H, m, br). MS (ES-API positive): 423 (M+H)$^+$.

Synthesis of 4-[7-(4-Cyano-2-trifluoromethyl-phenyl)-8-oxo-6-thioxo-5,7-diaza-spiro[3.4]oct-5-yl]-2-fluoro-N-methyl-benzamide (Example 7)

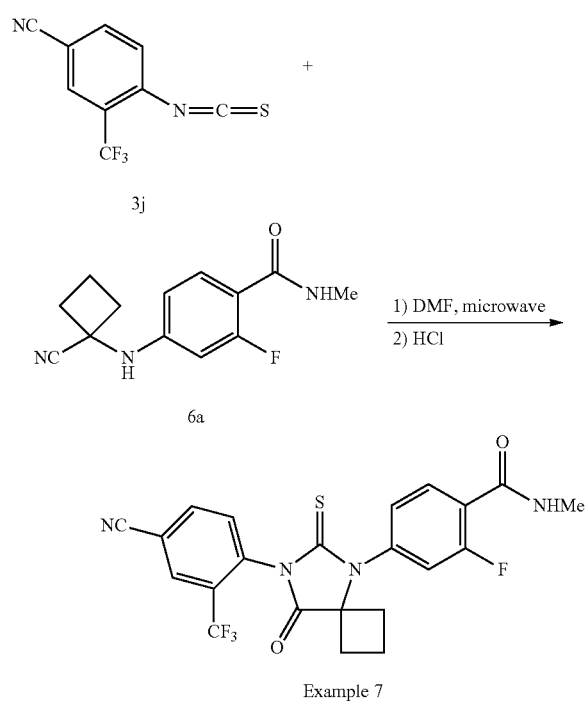

Example 7

A mixture of 3j (456 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 7, 210 mg, 22% yield). $^1$H NMR (CDCl$_3$, 500 MHz): δ 8.30 (1H, dd, J=8.6, 3.5 Hz), 8.12 (1H, d, J=1.5 Hz), 8.01 (1H, dd, J=8.5, 2.0 Hz), 7.58 (1H, d, J=8.0 Hz), 7.26 (1H, m.br), 7.15 (1H, dd, J=11.5, 2.0 Hz), 6.71 (1H, br s), 3.00 (3H, d, J=5 Hz), 2.70 (2H, m), 2.52 (2H, m), 2.15 (1H, m), 1.68 (1H, m, br). MS (ES-API positive): 477 (M+H)$^+$.

Synthesis of 4-[7-(3-Chloro-4-cyano-2-fluoro-phenyl)-8-oxo-6-thioxo-5,7-diaza-spiro[3.4]oct-5-yl]-2-fluoro-N-methyl-benzamide (Example 8)

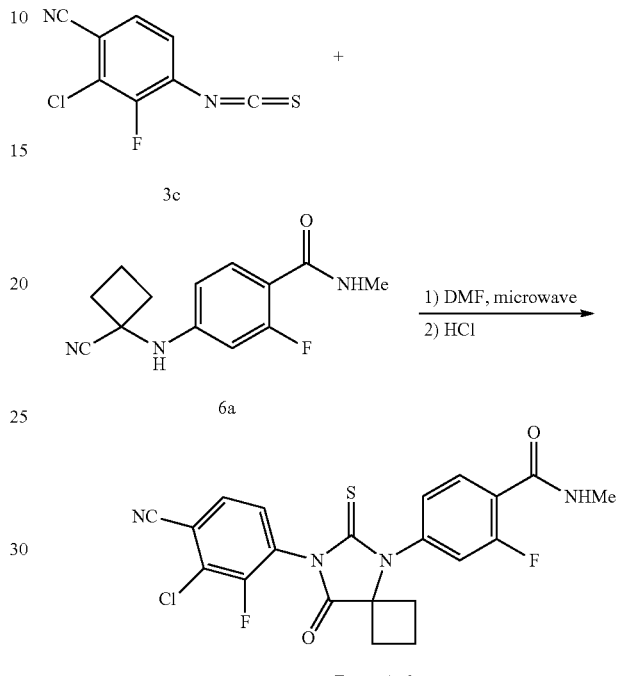

Example 8

A mixture of 3c (424 mg, 2 mmol) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 8, 235 mg, 24% yield). $^1$H NMR (CDCl$_3$, 500 MHz): δ 8.39 (1H, t, J=9.0 Hz), 7.62 (1H, dd, J=8.0, 1.5 Hz), 7.50 (1H, dd, J=8.5, 6.5 Hz), 7.26 (1H, m.br), 7.19 (1H, dd, J=12.0, 2.0 Hz), 6.71 (1H, br s), 3.00 (3H, d, J=5 Hz), 2.70 (2H, m), 2.52 (2H, m), 2.26 (1H, m), 1.69 (1H, m, br). MS (ES-API positive): 461 (M+H)$^+$.

Synthesis of 4-[7-(3,4-Dicyano-phenyl)-8-oxo-6-thioxo-5,7-diaza-spiro[3.4]oct-5-yl]-2-fluoro-N-methyl-benzamide (Example 9)

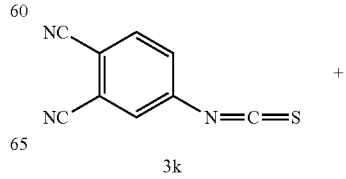

3k

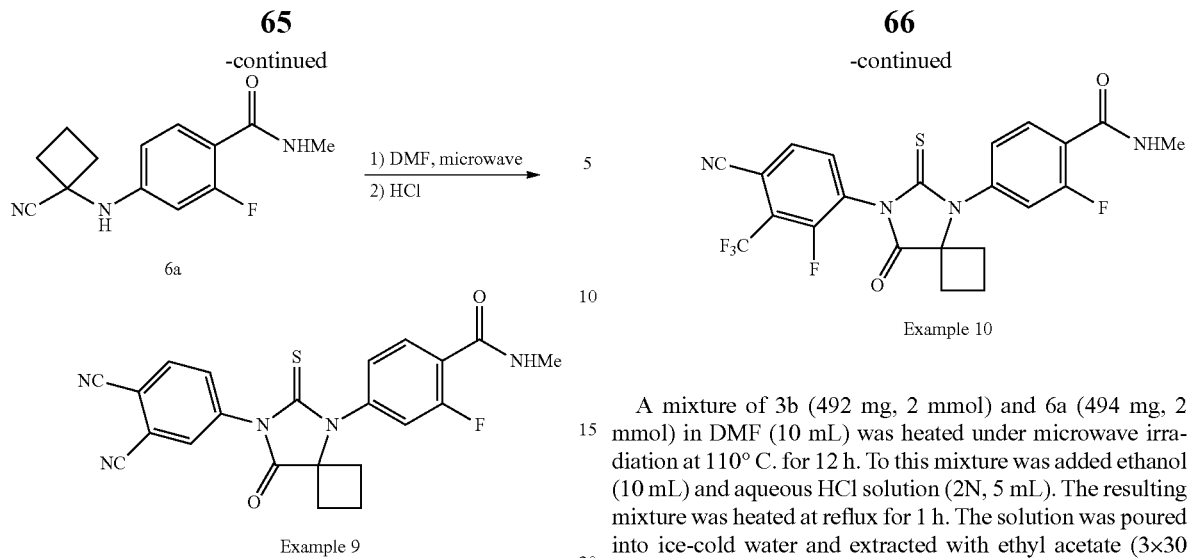

A mixture of 3k (370 mg, 2 mmol, prepared by a method similar to the synthesis of 3d) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 9, 200 mg, 23% yield). $^1$H NMR (CDCl$_3$, 500 MHz): δ 8.39 (1H, t, J=9.0 Hz), 8.00 (1H, d, J=2.0 Hz), 7.90 (2H, m.br), 7.26 (1H, m.br), 7.18 (1H, dd, J=11.5, 2.0 Hz), 6.71 (1H, br s), 3.00 (3H, d, J=5 Hz), 2.70 (2H, m), 2.52 (2H, m), 2.26 (1H, m), 1.62 (1H, m, br). MS (ES-API positive): 434 (M+H)$^+$.

Synthesis of 4-[7-(4-Cyano-2-fluoro-3-trifluoromethyl-phenyl)-8-oxo-6-thioxo-5,7-diaza-spiro[3.4]oct-5-yl]-2-fluoro-N-methyl-benzamide (Example 10)

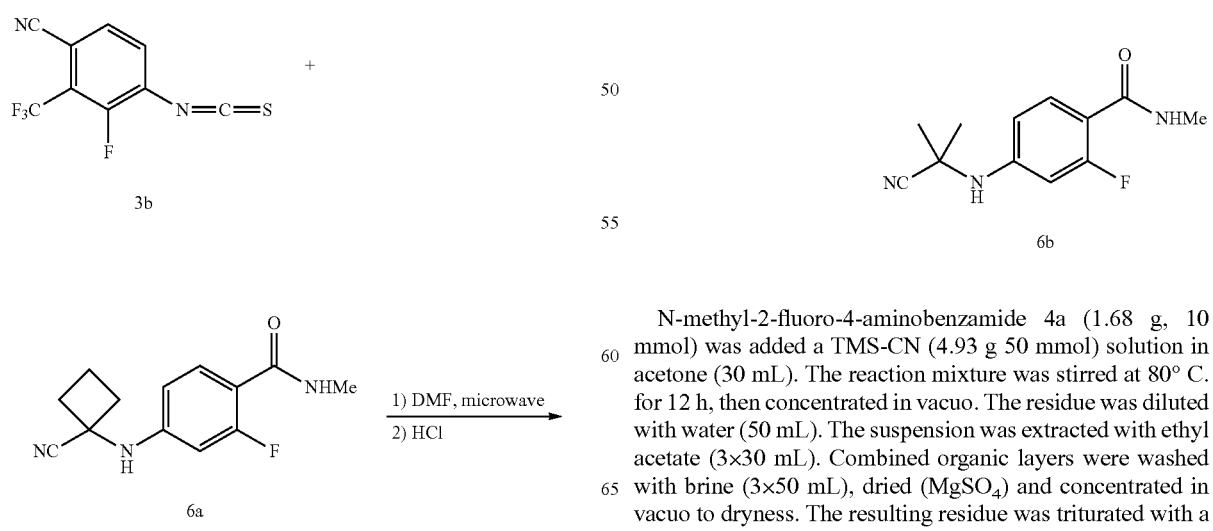

A mixture of 3b (492 mg, 2 mmol) and 6a (494 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether: ethyl acetate/(1:1), affording the title compound (Example 10, 200 mg, 30% yield). $^1$H NMR (CDCl$_3$, 500 MHz): δ 8.34 (1H, t, J=9.0 Hz), 7.80 (1H, dd, J=15.5, 8.5 Hz), 7.26 (1H, m.br), 7.18 (1H, dd, J=11.5, 2.0 Hz), 6.71 (1H, br s), 3.00 (3H, d, J=5 Hz), 2.70 (2H, m), 2.52 (2H, m), 2.26 (1H, m), 1.7 (1H, m, br). MS (ES-API positive): 495 (M+H)$^+$.

Synthesis of 4-[(Cyano-dimethyl-methyl)-amino]-2-fluoro-N-methyl-benzamide (6b)

N-methyl-2-fluoro-4-aminobenzamide 4a (1.68 g, 10 mmol) was added a TMS-CN (4.93 g 50 mmol) solution in acetone (30 mL). The reaction mixture was stirred at 80° C. for 12 h, then concentrated in vacuo. The residue was diluted with water (50 mL). The suspension was extracted with ethyl acetate (3×30 mL). Combined organic layers were washed with brine (3×50 mL), dried (MgSO$_4$) and concentrated in vacuo to dryness. The resulting residue was triturated with a mixed solvent of hexanes and ethylether (20 mL-20 mL). The solid was collected by filtration, affording the title compound 6b (1.8 g, 79% yield). MS (ES-API Negative): 234 (M–H)⁻.

Synthesis of 4-[3-(3-Chloro-4-cyano-2-fluoro-phenyl)-5,5-dimethyl-4-oxo-2-thioxo-imidazolidin-1-yl]-2-fluoro-N-methyl-benzamide (Example 11)

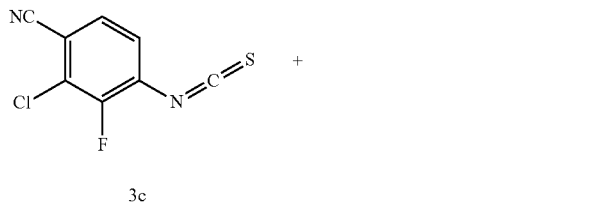

A mixture of 3c (424 mg, 2 mmol) and 6b (470 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO₄, and concentrated in vacuo. The residue was purified with silica gel column chromatography using petroleum ether: ethyl acetate (2:1), affording the title compound (Example 11, 220 mg, 23% yield). ¹H NMR (CDCl₃, 500 MHz): δ 8.22 (1H, dd, J=8.6, 3.5), 7.58 (1H, dd, J=7.5, 1.5), 7.42 (1H, dd, J=8.5, 4.5 Hz), 7.26 (1H, m), 7.10 (1H, dd, J=10.5, 1.5 Hz), 6.60 (1H, br s), 3.00 (3H, d, J=5 Hz), 1.53 (6H, s). MS (ES-API positive): 449 (M+H)⁺.

Synthesis of 4-[3-(4-Cyano-2-fluoro-3-trifluoromethyl-phenyl)-5,5-dimethyl-4-oxo-2-thioxo-imidazolidin-1-yl]-2-fluoro-N-methyl-benzamide (Example 12)

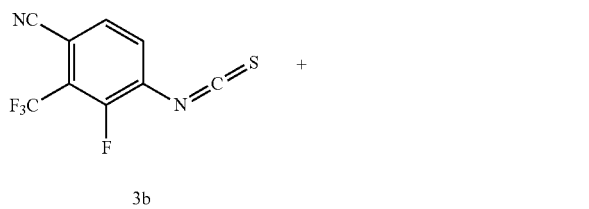

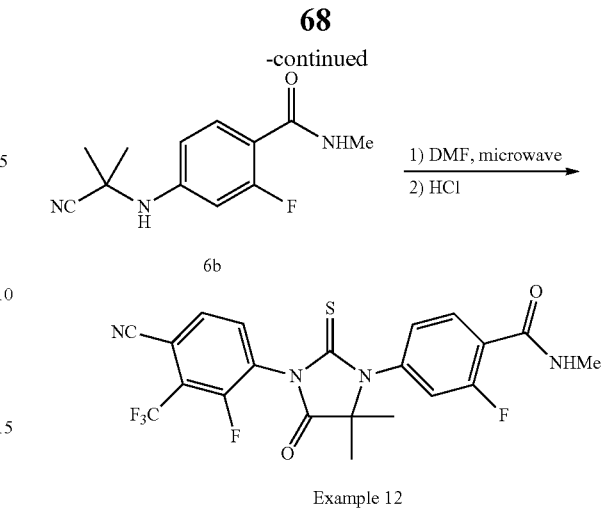

A mixture of 3b (492 mg, 2 mmol) and 6b (470 mg, 2 mmol) in DMF (10 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO4, and concentrated in vacuo. The residue was purified with silica gel column chromatography using petroleum ether: ethyl acetate (2:1), affording the title compound (Example 12, 320 mg, 33% yield). ¹H NMR (CDCl₃, 500 MHz): δ 8.28 (1H, dd, J=8.6, 3.5), 7.80 (2H, dd, J=15.6, 8.0), 7.26 (1H, m), 7.18 (1H, dd, J=12.0, 2.0 Hz), 6.7 (1H, br s), 3.00 (3H, d, J=5 Hz), 1.53 (6H, s). MS (ES-API positive): 483 (M+H)⁺.

Synthesis of 3-Fluoro-4-[3-(4-methanesulfonyl-phenyl)-4,4-dimethyl-5-oxo-2-thioxo-imidazolidin-1-yl]-2-trifluoromethyl-benzonitrile (Example 13)

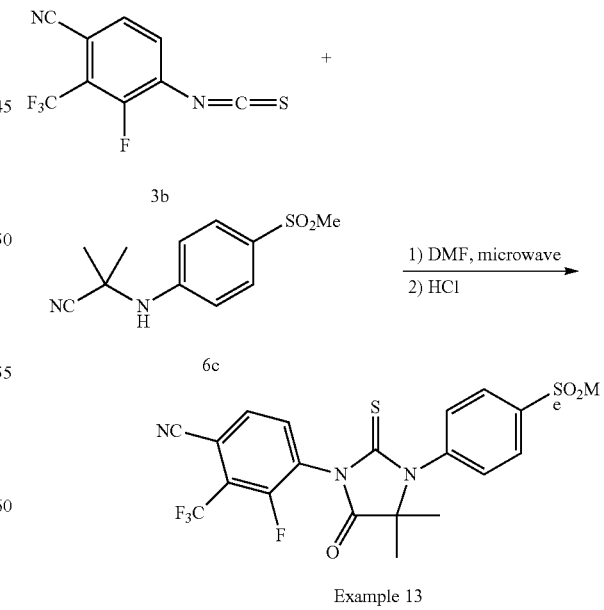

A mixture of 3b (492 mg, 2 mmol) and 6c (476 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using Petroleum ether:Ethyl acetate (2:1), affording the title compound (Example 13, 180 mg, 18% yield). $^1$H NMR (CDCl$_3$, 500 MHz): δ 8.14 (2H, d), 7.82 (2H, d), 7.56 (2H, dd), 3.16 (3H, s), 1.62 (6H, s). MS (ES-API positive): 486 (M+H)$^+$.

Synthesis of 4-(4,4-Dimethyl-5-oxo-2-thioxo-3-p-cyanophenyl-imidazolidin-1-yl)-3-fluoro-2-trifluoromethyl-benzonitrile (Example 14)

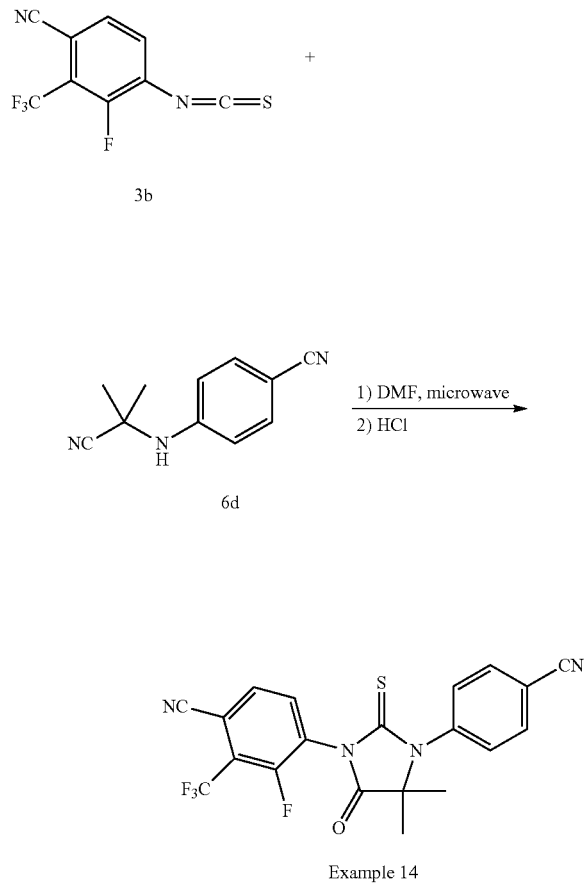

A mixture of 3b (492 mg, 2 mmol) and 6d (370 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 14, 150 mg, 17% yield). $^1$H NMR (CDCl$_3$, 500 MHz): δ 7.86 (2H, d), 7.80 (2H, s), 7.48 (2H, d), 1.61 (6H, s). MS (ES-API positive): 433 (M+H)$^+$.

Synthesis of 4-[4,4-Dimethyl-3-(6-methyl-pyridin-3-yl)-5-oxo-2-thioxo-imidazolidin-1-yl]-3-fluoro-2-trifluoromethyl-benzonitrile (Example 15)

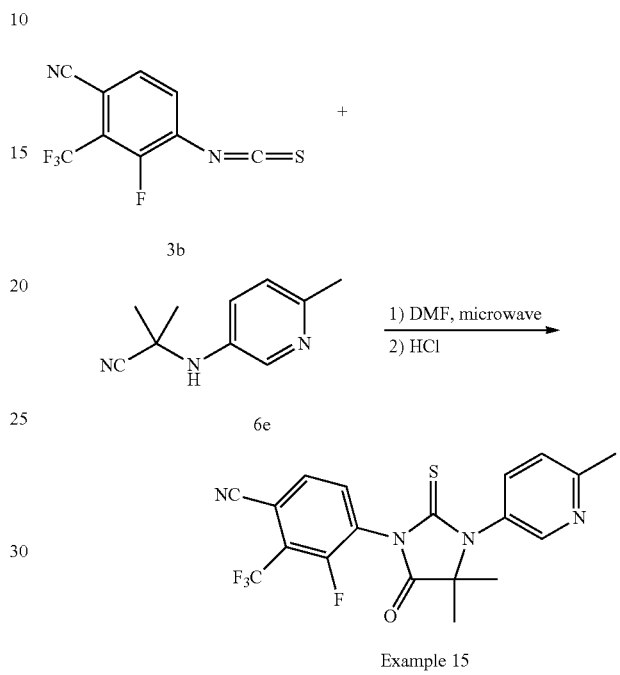

A mixture of 3b (492 mg, 2 mmol) and 6e (350 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 15, 130 mg, 15% yield). $^1$H NMR (CDCl$_3$, 500 MHz): δ 8.46 (1H, s), 7.78-7.85 (2H, m), 7.55-7.57 (1H, m), 7.35 (1H, d), 2.66 (3H, s), 1.60 (6H, s). MS (ES-API positive): 423 (M+H)$^+$.

Synthesis of 2-Chloro-3-fluoro-4-[3-(4-methanesulfonyl-phenyl)-4,4-dimethyl-5-oxo-2-thioxo-imidazolidin-1-yl]-benzonitrile (Example 16)

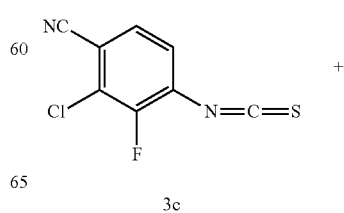

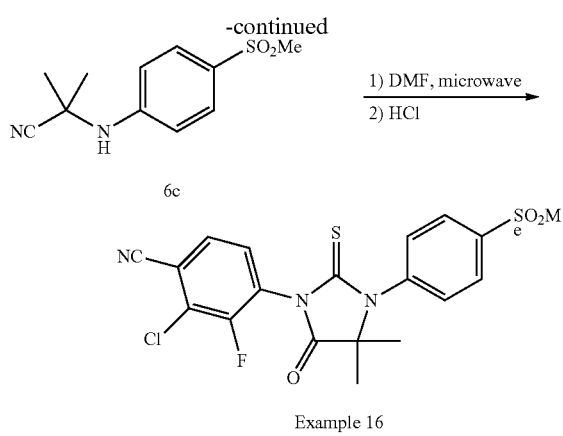

Example 16

A mixture of 3c (424 mg, 2 mmol) and 6c (476 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 16, 160 mg, 18% yield). $^1$H NMR (CDCl$_3$, 500 MHz): δ 8.13 (2H, d), 7.65 (1H, dd), 7.58 (2H, d), 7.50 (1H, dd), 3.16 (3H, s), 1.60 (6H, s). MS (ES-API positive): 452 (M+H)$^+$.

Synthesis of 2-Chloro-4-[4,4-dimethyl-3-(6-methyl-pyridin-3-yl)-5-oxo-2-thioxo-imidazolidin-1-yl]-3-fluoro-benzonitrile (Example 17)

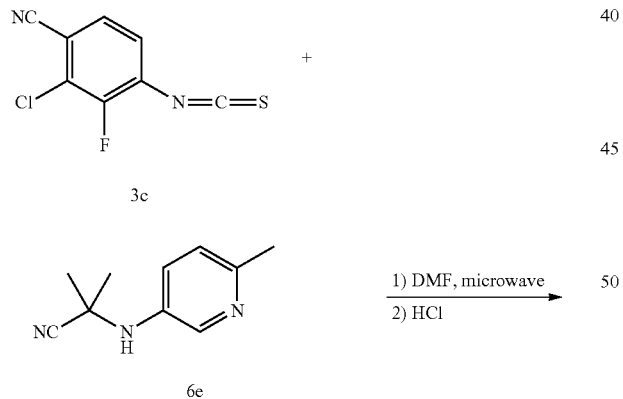

Example 17

A mixture of 3c (424 mg, 2 mmol) and 6e (350 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 17, 210 mg, 27% yield). $^1$H NMR (DMSO-d$_6$, 500 MHz): δ 8.50 (1H, d), 8.12 (1H, dd), 7.91 (1H, dd), 7.80 (1H, dd), 7.48 (1H, dd), 2.57 (3H, s), 1.52 (6H, s). MS (ES-API positive): 389 (M+H)$^+$.

Synthesis of 4-(4,4-Dimethyl-5-oxo-2-thioxo-3-p-cyanophenyl-imidazolidin-1-yl)-3-fluoro-2-chloro-benzonitrile (Example 18)

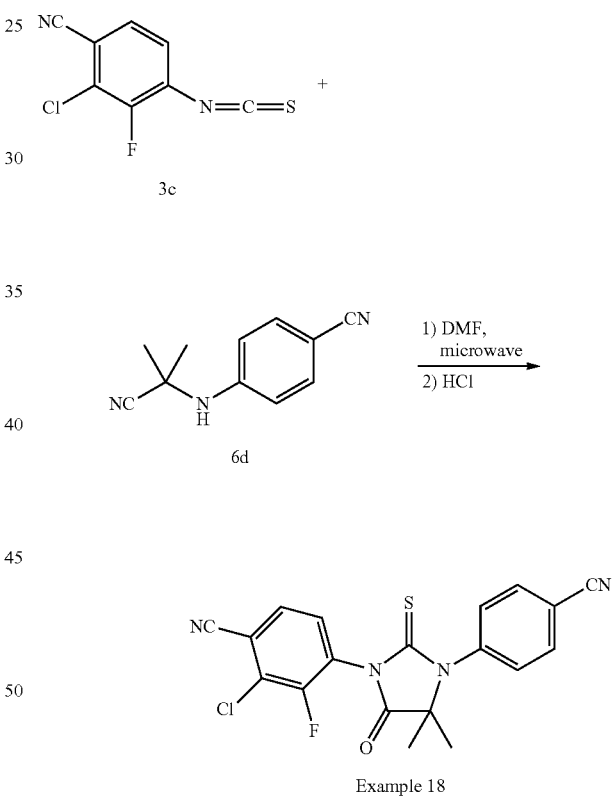

Example 18

A mixture of 3c (424 mg, 2 mmol) and 6d (370 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 18, 140 mg, 17% yield). $^1$H NMR (CDCl$_3$, 500 MHz): δ 7.86 (2H, d), 7.64 (1H, dd), 7.47-7.50 (3H, m), 1.60 (6H, s). MS (ES-API positive): 399 (M+H)$^+$.

Synthesis of 3-Fluoro-4-[3-(4-fluoro-phenyl)-4,4-dimethyl-5-oxo-2-thioxo-imidazolidin-1-yl]-2-methoxy-benzonitrile (Example 19)

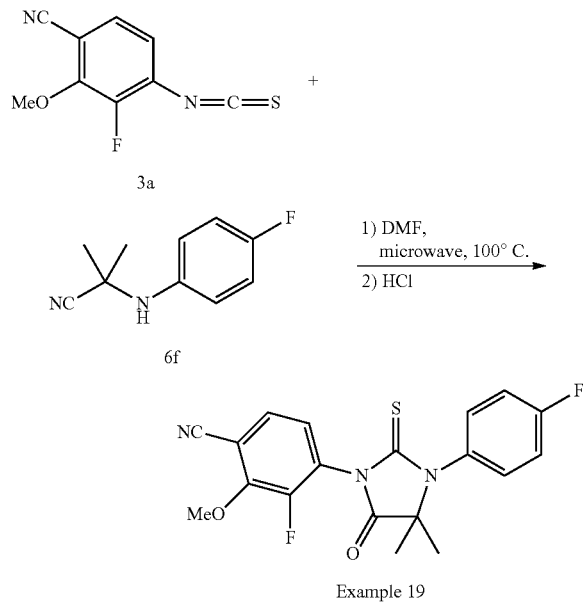

Example 19

A mixture of 3a (416 mg, 2 mmol) and 6f (356 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 19, 150 mg, 19% yield). $^1$H NMR (DMSO-d$_6$, 500 MHz): δ 7.84 (1H, d), 7.49-7.53 (3H, m), 7.40-7.43 (2H, m), 4.12 (3H, d), 1.50 (6H, s). MS (ES-API positive): 388 (M+H)$^+$.

Synthesis of 4-[4,4-Dimethyl-3-(6-methyl-pyridin-3-yl)-5-oxo-2-thioxo-imidazolidin-1-yl]-3-fluoro-2-methoxy-benzonitrile (Example 20)

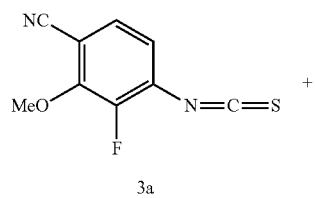

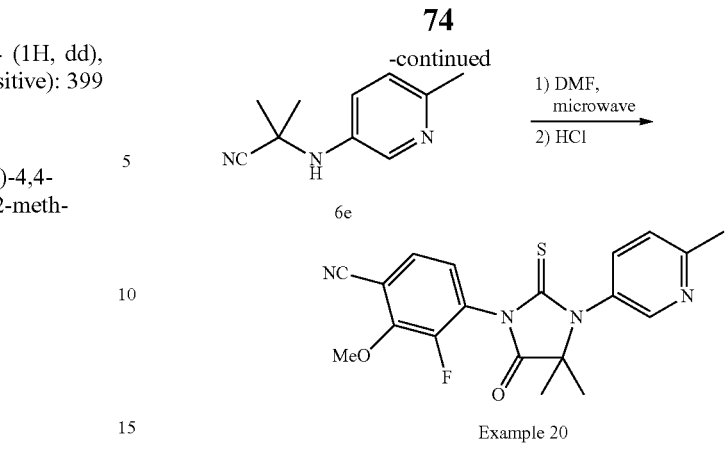

Example 20

A mixture of 3a (416 mg, 2 mmol) and 6e (350 mg, 2 mmol, prepared by a method similar to the synthesis of 6b) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using petroleum ether:ethyl acetate (1:1), affording the title compound (Example 20, 180 mg, 23% yield). $^1$H NMR (CDCl$_3$, 500 MHz): δ 8.77 (1H, d), 7.93 (1H, dd), 7.58 (1H, d), 7.50 (1H, dd), 7.16 (1H, dd), 4.20 (3H, d), 2.80 (3H, s), 1.63 (6H, s). MS (ES-API positive): 385 (M+H)$^+$.

Synthesis of 3-Fluoro-4-[3-(4-methanesulfonyl-phenyl)-4,4-dimethyl-5-oxo-2-thioxo-imidazolidin-1-yl]-2-methoxy-benzonitrile (Example 21)

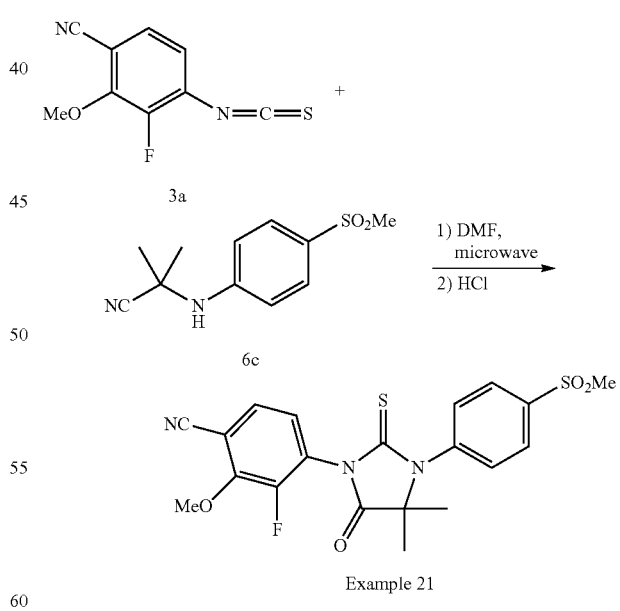

Example 21

A mixture of 3a (416 mg, 2 mmol) and 6c (476 mg, 2 mmol, prepared by a method similar to the synthesis of 6b) in DMF (5 mL) was heated under irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO₄, and concentrated in vacuo. The residue was purified with silica gel column chromatography using Petroleum ether:Ethyl acetate (1:1), affording the title compound (Example 21, 130 mg, 14% yield). ¹H NMR (CDCl₃, 500 MHz): δ 8.13 (2H, d), 7.57 (2H, d), 7.49 (1H, dd), 7.17 (1H, dd), 4.20 (3H, d), 3.16 (3H, s), 1.61 (6H, s). MS (ES-API positive): 448 (M+H)⁺.

Synthesis of 4-[3-(4-Cyano-2-fluoro-3-methoxy-phenyl)-5,5-dimethyl-4-oxo-2-thioxo-imidazolidin-1-yl]-2-fluoro-N-methyl-benzamide (Example 22)

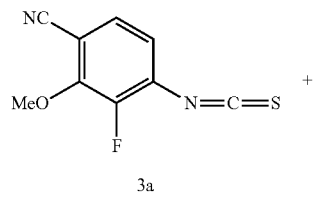

3a

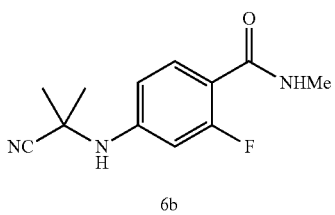

6b

1) DMF, microwave
2) HCl

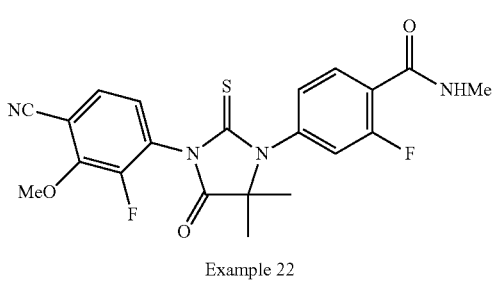

Example 22

A mixture of 3a (416 mg, 2 mmol) and 6b (470 mg, 2 mmol) in DMF (5 mL) was heated under microwave irradiation at 110° C. for 12 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO₄, and concentrated in vacuo. The residue was purified with silica gel column chromatography using Petroleum ether: Ethyl acetate (1:1), affording the title compound (Example 22, 160 mg, 18% yield). ¹H NMR (CDCl₃, 500 MHz): δ 8.27 (1H, t), 7.48 (1H, dd), 7.26 (1H, m), 7.15-7.18 (2H, m), 6.70 (1H, br s), 4.20 (3H, d), 3.00 (3H, d), 1.6 (6H, s). MS (ES-API positive): 445 (M+H)⁺.

Synthesis of 4-(4,4-Dimethyl-5-oxo-2-thioxo-3-p-tolyl-imidazolidin-1-yl)-3-fluoro-2-methoxy-benzonitrile (Example 23)

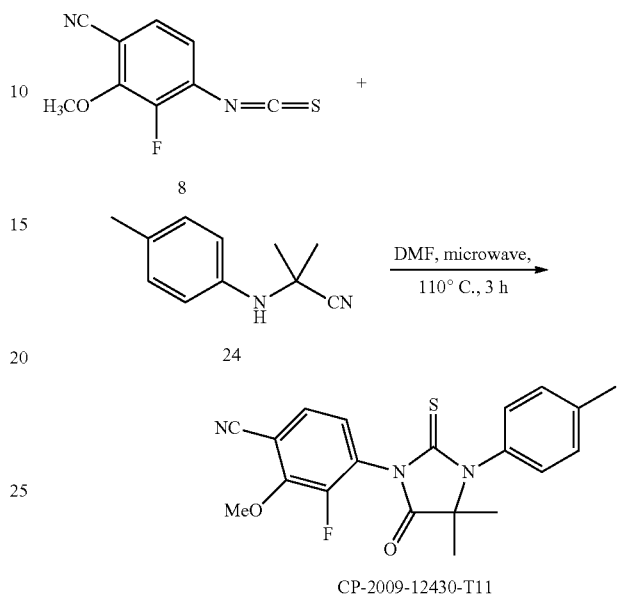

CP-2009-12430-T11

A mixture of 3a (416 mg, 2 mmol) and 6 g (348 mg, 2 mmol, prepared by a method similar to the synthesis of 6b) in DMF (10 mL) was heated under microwave irradiation at 110° C. for 3 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO₄, and concentrated in vacuo. The residue was purified with Pre-HPLC, affording the title compound (Example 23, 70 mg, 5% yield). ¹H NMR (400 MHz, CDCl₃) δ: 7.48 (dd, 1H), 7.33 (dd, 2H), 7.19 (dd, 3H), 4.19 (d, 3H), 2.43 (s, 3H), 1.56 (s, 6H). ESI-MS (M+H)⁺: 384.

Synthesis of 4-(4,4-Dimethyl-5-oxo-2-thioxo-3-p-tolyl-imidazolidin-1-yl)-phthalonitrile (Example 24)

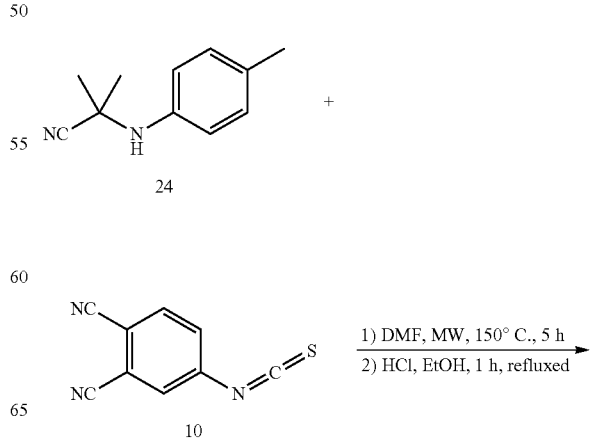

-continued

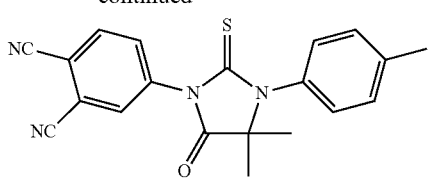

CP-2009-12430-T12

A mixture of 3k (370 mg, 2 mmol, prepared by a method similar to the synthesis of 3d) and 6g (348 mg, 2 mmol, prepared by a method similar to the synthesis of 6b) in DMF (10 mL) was heated under microwave irradiation at 150° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with Pre-HPLC, affording the title compound (Example 24, 60 mg, 8.3% yield) as a yellow solid. $^1$H NMR (400 MHz, CDCl$_3$) δ 8.03 (s, 1H), 7.93 (m, 2H), 7.35 (d, J=8 Hz, 2H), 7.16 (d, J=8 Hz, 2H), 2.44 (s, 3H), 1.58 (s, 6H). ESI-MS (M+H)$^+$: 361.

Synthesis of 4-[3-(3-Fluoro-4-methyl-phenyl)-4,4-dimethyl-5-oxo-2-thioxo-imidazolidin-1-yl]-phthalonitrile (Example 25)

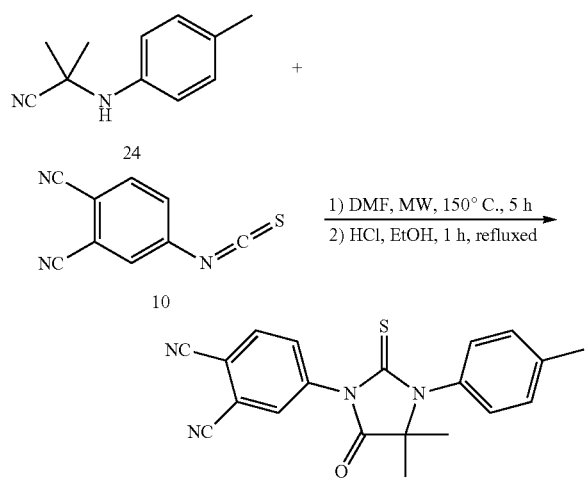

CP-2009-12430-T12

A mixture of 3k (370 mg, 2 mmol, prepared by a method similar to the synthesis of 3d) and 6h (384 mg, 2 mmol, prepared by a method similar to the synthesis of 6b) in DMF (10 mL) was heated under microwave irradiation at 150° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with Pre-HPLC, affording the title compound (Example 25, 150 mg, 19.8% yield) as a yellow solid. $^1$H NMR (400 MHz, CDCl$_3$) δ 8.01 (s, 1H), 7.93-7.91 (m, 2H), 7.26-7.09 (m, 3H), 2.35 (s, 3H), 1.58 (s, 6H). ESI-MS (M+H)$^+$: 379.

Synthesis of 3-Fluoro-4-[3-(3-fluoro-4-methyl-phenyl)-4,4-dimethyl-5-oxo-2-thioxo-imidazolidin-1-yl]-2-methoxy-benzonitrile (Example 26)

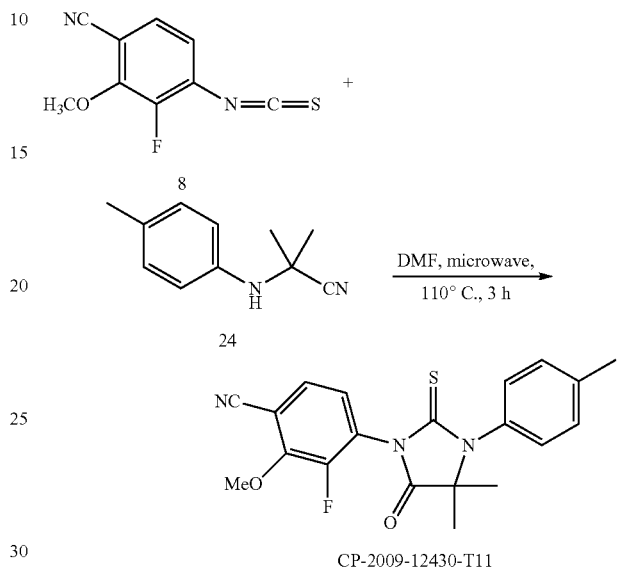

CP-2009-12430-T11

A mixture of 3a (416 mg, 2 mmol) and 6h (384 mg, 2 mmol, prepared by a method similar to the synthesis of 6b) in DMF (10 mL) was heated under microwave irradiation at 150° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with Pre-HPLC, affording the title compound (Example 26, 60 mg, 7.48% yield) as a light yellow solid. $^1$H NMR (400 MHz, CDCl$_3$) δ 7.49-7.47 (m, 1H), 7.19-7.13 (m, 4H), 4.19 (s, 3H), 2.34 (s, 3H), 1.57 (s, 6H); ESI-MS (M+H)$^+$: 402.

Synthesis of 4-[3-(4-Cyano-2-fluoro-3-trifluoromethyl-phenyl)-5,5-dimethyl-4-oxo-2-thioxo-imidazolidin-1-yl]-benzoic acid ethyl ester (Example 27)

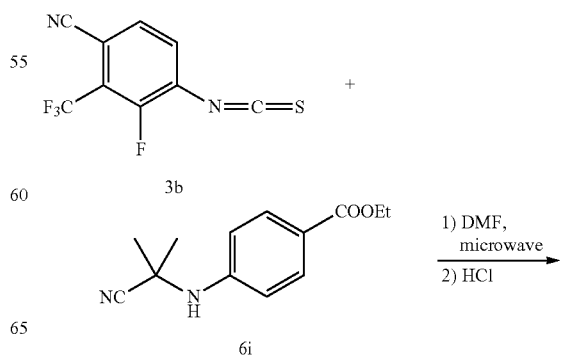

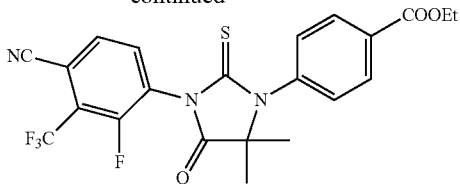

Example 27

A mixture of 3b (123 mg, 0.5 mmol) and 6i (116 mg, 0.5 mmol, prepared by a method similar to the synthesis of 6b) in DMF (2.5 mL) was heated under microwave irradiation at 145° C. for 5 h. To this mixture was added ethanol (5 mL) and aqueous HCl solution (2N, 2.5 mL). The resulting mixture was heated at reflux for 1 h. The solution was poured into ice-cold water and extracted with ethyl acetate (3×20 mL). The organic layers were combined, dried over MgSO$_4$, and concentrated in vacuo. The residue was purified with silica gel column chromatography using Petroleum ether:Ethyl acetate (1:1), affording the title compound (Example 27, 45 mg, 18.8% yield). $^1$H NMR (400 MHz, CDCl$_3$) δ 8.22 (d, 2H), 7.83-7.80 (m, 2H), 7.42 (d, 2H), 4.45-4.41 (m, 2H), 1.61 (s, 6H), 1.43-1.40 (m, 3H); ESI-MS (M+H)$^+$: 480.

Synthesis of 4-(4,4-Dimethyl-5-oxo-2-thioxo-3-p-tolyl-imidazolidin-1-yl)-3-fluoro-2-trifluoromethyl-benzonitrile (Example 28)

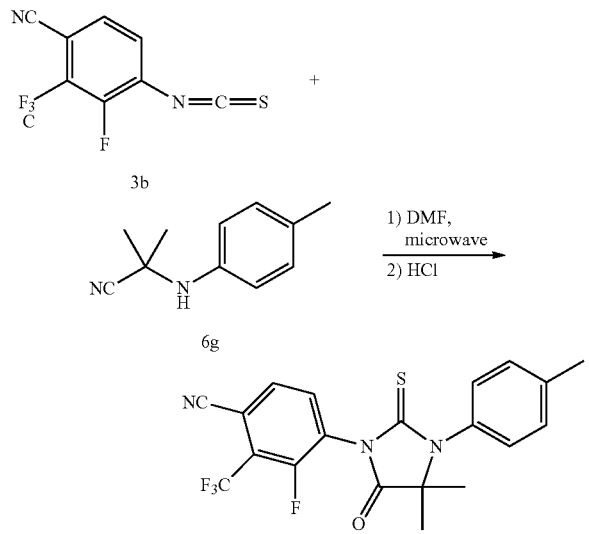

Example 28

A mixture of 3b (492 mg, 2 mmol) and 6g (348 mg, 2 mmol, prepared by a method similar to the synthesis of 6b) in DMF (5 mL) was heated under microwave irradiation at 110° C. for 3 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified with silica gel column chromatography using Petroleum ether:Ethyl acetate (1:1), affording the title compound (Example 28, 80 mg, 9.5% yield). $^1$H NMR (400 MHz, CDCl$_3$) δ 8.03 (s, 1H), 7.03 (dd, 2H), 7.35 (d, J=8 Hz, 2H), 7.16 (d, J=8 Hz, 2H), 2.44 (s, 3H), 1.58 (s, 6H). ESI-MS (M+H)$^+$: 422.

Synthesis of 2-Chloro-4-(4,4-dimethyl-5-oxo-2-thioxo-3-p-tolyl-imidazolidin-1-yl)-3-fluoro-benzonitrile (Example 29)

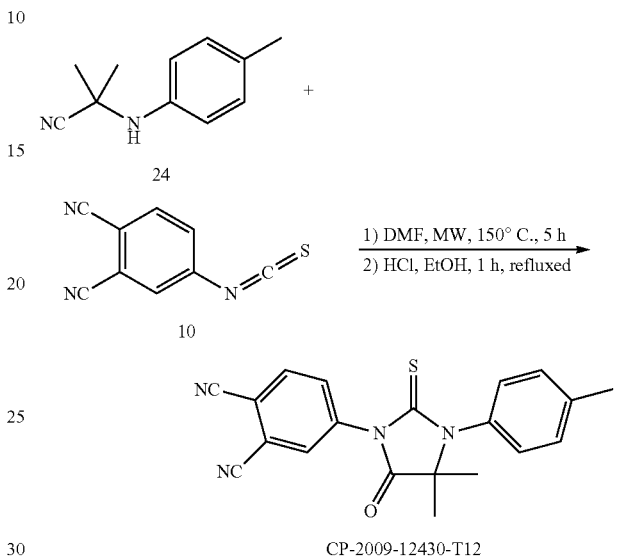

CP-2009-12430-T12

A mixture of 3c (370 mg, 2 mmol, prepared by a method similar to the synthesis of 3d) and 6g (348 mg, 2 mmol, prepared by a method similar to the synthesis of 6b) in DMF (5 mL) was heated under microwave irradiation at 150° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over MgSO$_4$, and concentrated in vacuo. The residue was purified by Pre-HPLC, affording the title compound (Example 29, 60 mg, 7.7% yield). $^1$H NMR (400 MHz, CDCl$_3$) δ 7.64-7.62 (m, 1H), 7.54-7.51 (m, 1H), 7.34 (d, J=8 Hz, 2H), 7.19 (d, J=8 Hz, 2H), 2.43 (s, 3H), 1.58 (s, 6H). ESI-MS (M+H)$^+$: 388.

Synthesis of 3-Fluoro-4-[3-(3-fluoro-4-methyl-phenyl)-4,4-dimethyl-5-oxo-2-thioxo-imidazolidin-1-yl]-2-trifluoromethyl-benzonitrile (Example 30)

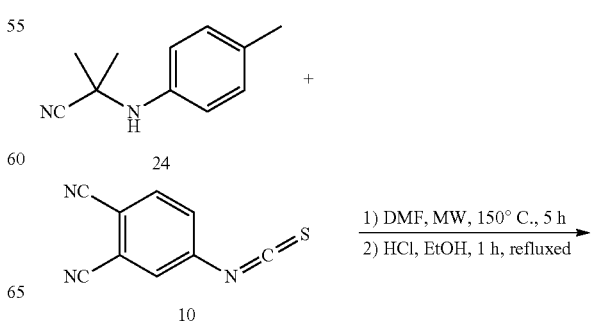

A mixture of 3b (492 mg, 2 mmol) and 6h (384 mg, 2 mmol, prepared by a method similar to the synthesis of 6b) in DMF (5 mL) was heated under microwave irradiation at room temperature for 2 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over $MgSO_4$, and concentrated in vacuo. The residue was purified by Pre-HPLC, affording the title compound (Example 30, 110 mg, 12.5% yield) as a yellow solid. $^1$H NMR (400 MHz, $CDCl_3$) δ 7.75-7.70 (m, 2H), 7.07-7.06 (m, 3H), 2.25 (s, 3H), 1.49 (s, 6H). ESI-MS $(M+H)^+$: 440.

Synthesis of 2-Chloro-3-fluoro-4-[3-(3-fluoro-4-methyl-phenyl)-4,4-dimethyl-5-oxo-2-thioxo-imidazolidin-1-yl]-benzonitrile (Example 31)

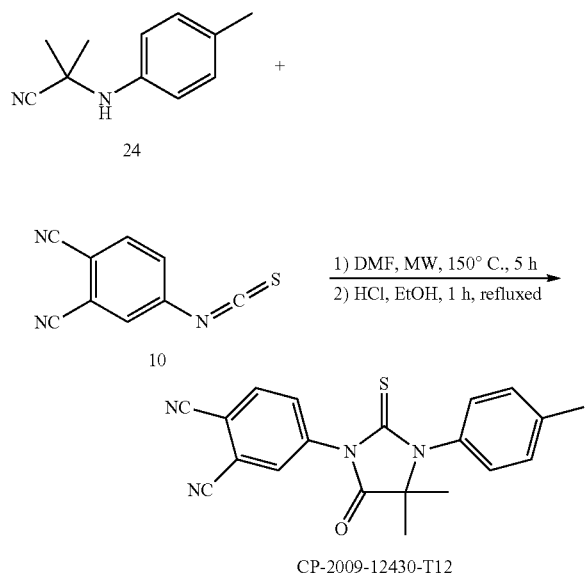

A mixture of 3c (370 mg, 2 mmol, prepared by a method similar to the synthesis of 3d) and 6h (384 mg, 2 mmol, prepared by a method similar to the synthesis of 6b) in DMF (5 mL) was heated under microwave irradiation at 150° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over $MgSO_4$, and concentrated in vacuo. The residue was purified by Pre-HPLC, affording the title compound (Example 31, 60 mg, 7.5% yield) as a yellow solid. $^1$H NMR (400 MHz, $CDCl_3$) δ 7.65-7.63 (m, 1H), 7.52-7.50 (m, 3H), 2.35 (s, 3H), 1.58 (s, 6H). ESI-MS $(M+H)^+$: 406.

Synthesis of 4-(4,4-Dimethyl-5-oxo-2-thioxo-3-p-cyanophenyl-imidazolidin-1-yl)-3-fluoro-2-methoxy-benzonitrile (Example 32)

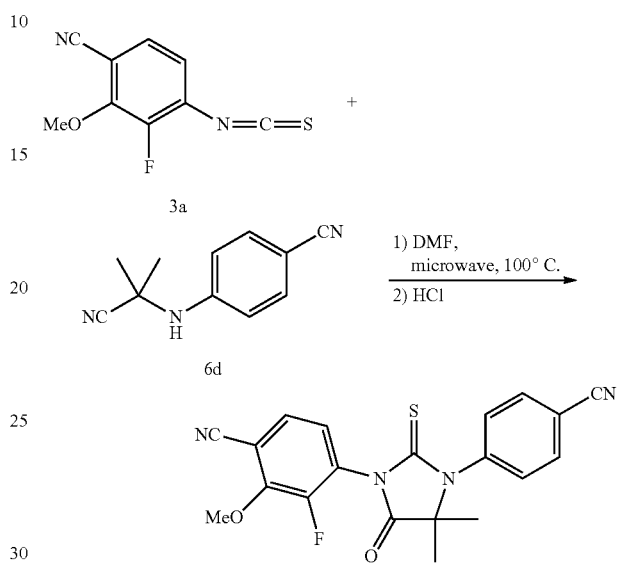

Example 32

A mixture of 3a (416 mg, 2 mmol) and 6d (370 mg, 2 mmol, prepared by a method similar to the synthesis of 6b) in DMF (5 mL) was heated under microwave irradiation at 110° C. for 5 h. To this mixture was added ethanol (10 mL) and aqueous HCl solution (2N, 5 mL). The resulting mixture was heated at reflux for 1 h. The solution was poured into ice-cold water and extracted with ethyl acetate (3×30 mL). The organic layers were combined, dried over $MgSO_4$, and concentrated in vacuo. The residue was purified with silica gel column chromatography using Petroleum ether:Ethyl acetate (1:1), affording the title compound (Example 32, 190 mg, 23% yield). $^1$H NMR ($CDCl_3$, 500 MHz): δ 7.85 (2H, d), 7.47-7.50 (3H, m), 7.18 (1H, dd), 1.59 (6H, s). MS (ES-API positive): 395 $(M+H)^+$.

TEST EXAMPLES

Biological Activity

The compounds of the present invention are antagonist of the androgen receptor. The preferred compounds have potent antagonistic activity ($IC_{50}$<1 μM) without any significant agonism. As discussed in the background section, selective antagonists are useful for treatment of androgen receptor-associated conditions, especially for prostate cancer including hormone sensitive and hormone refractory disease. The compounds of the present invention can be used alone or in combination with one or more other therapeutic agent(s).

The compounds in the present invention were screened by testing on hormone sensitive (LNCaP, LAPC4) and hormone refractory prostate cancer cells (LNCaP-AR, LAPC4-AR, LNCaP C4-2, 22RV1, LNCaP-AI and LNCaP-ab1) for antagonistic and agonistic activities. Prostate specific antigen (PSA) level can also be used as a marker for androgen receptor antagonistic activity. The MTS assay is also used to evaluate the present compounds for potency of inhibiting cell growth. The selective, potent androgen receptor antagonists with acceptable rodent oral bioavailability are further evaluated for in vivo efficacy using prostate cancer xenografts. The cell lines used can be selected from LNCaP, LAPC4, LAPC9, CWR22, LNCaP-AR, LNCaP C4-2, 22RV1, LNCaP-ab1 and LNCaP-AI.

PSA Assay (Inhibition Test of the Compound of the Present Invention on Prostate-Specific Antigen (PSA) Production in Various Prostate Cancer Cells)

Androgen dependent LNCaP and 22RV1 cells were purchased from the American Type Culture Collection (ATCC, Manassas, Va.). These cells were grown in RPMI 1640 medium supplemented with 10% fetal bovine serum (FBS), 100 U/mL penicillin, 100 μg/mL streptomycin, and 0.25 μg/mL amphotericin B. The cells were maintained at 37° C. and 5% $CO_2$. LNCaP cells between passage 20 and 35, and 22RV1 cells between passage 30 and 50 were used for experiments. LNCaP is a hormone sensitive cell line, while 22RV1 is a hormone refractory prostate cancer cell line, which derived from a primary prostate tumor. This cell line was isolated from a xenograft (CWR22R-2152) that was serially propagated in mice after castration-induced regression and relapse of the parental, androgen-dependent CWR xenograft. For the PSA assay, human prostate cancer cells LNCaP or 22RV1 were seeded in a 96-well plate at a concentration of 5000 cells/100 μl/well. On the following day, Methyltrienolone (R1881, AR agonist) (final concentration 1 ng/ml), test compounds or bicalutamide (Casodex®, AstraZeneca) (final concentration 0.005 to 20 μM) were added. Three days after the addition, the concentration of PSA in the supernatant of the culture solution was measured by ELISA. ELISAs for human PSA in culture medium were performed using the ultra-sensitive assay procedure and reagents in the Active™ PSA assay kit (Diagnostic Systems Laboratories Inc., Webster, Tex.). Culture medium and standards (200 μl/well) were incubated in antibody-coated plates for 2 h at room temperature on a Titer plate shaker at 500-600 rpm. Wells were then washed five times. The HRP conjugate was diluted 1:20 with assay buffer, and 100 μl was added to all wells. The plates were incubated for 30 min at room temperature on the shaker and washed as before, and 100 μl TMB (3,3',5,5'-tetramethylbenzidine, 0.4 g/l) was added. The plates were incubated for 10 min on the shaker, and the reaction was terminated with 100 μl stop solution. The plates were read using a plate reader at 450 nm with a 650 nm reference filter. PSA levels were normalized for differences in growth of LNCaP or 22RV1 cells following various treatments as determined by the MTS assay. $IC_{50}$ of PSA was calculated based on a seven point assay (concentrations of tested compound) and expressed as micromolar (uM). Results on 22RV1 cells are shown as percent inhibition at 2 micromolar (uM). The results are shown in Table 1. ND means not determined

TABLE 1

Inhibition of PSA production in prostate cancer cells

| Compound | LNCaP $IC_{50}$ (uM) | 22RV1 % inhibition at 2uM |
|---|---|---|
| Bicalutamide | 3.1 | 18% |
| Compound of Example 1 | 2.4 | 48% |
| Compound of Example 2 | 0.45 | 47% |
| Compound of Example 3 | 2.1 | 21% |
| Compound of Example 4 | 1.4 | ND |
| Compound of Example 5 | 1.4 | ND |

TABLE 1-continued

Inhibition of PSA production in prostate cancer cells

| Compound | LNCaP $IC_{50}$ (uM) | 22RV1 % inhibition at 2uM |
|---|---|---|
| Compound of Example 6 | 1.5 | ND |
| Compound of Example 7 | 1.5 | ND |
| Compound of Example 8 | 0.85 | 77% |
| Compound of Example 9 | 0.98 | 64% |
| Compound of Example 10 | 0.38 | 78% |
| Compound of Example 11 | 0.23 | 81% |
| Compound of Example 12 | 0.28 | 71% |
| Compound of Example 13 | 0.52 | 61% |
| Compound of Example 14 | 0.49 | 71% |
| Compound of Example 15 | 0.35 | 69% |
| Compound of Example 16 | 0.63 | 70% |
| Compound of Example 17 | 0.31 | 76% |
| Compound of Example 18 | 0.092 | 89% |
| Compound of Example 19 | 0.29 | 72% |
| Compound of Example 20 | 0.28 | 69% |
| Compound of Example 21 | 1.8 | ND |
| Compound of Example 22 | 0.52 | 57% |
| Compound of Example 24 | 0.2 | 91% |
| Compound of Example 25 | 0.29 | 82% |
| Compound of Example 29 | 0.28 | 78% |
| Compound of Example 31 | 0.42 | 67% |
| Compound of Example 32 | 0.12 | 88% |

As is clear from Table 1, the compounds of the present invention showed a strong PSA production suppressing activity in both hormone sensitive and hormone refractory cells, as compared with bicalutamide.

Cell Viability Assays

LNCaP and 22RV1 cells were maintained in RPMI 1640 medium supplemented with 10% fetal bovine serum (FBS), 100 U/mL penicillin, 100 μg/mL streptomycin, and 0.25 μg/mL amphotericin B, splitting cells when they reached 80-90% confluence. In order to test compounds, 10,000 cells/well were plated in 96 cell culture plates using 100 ul/well plating medium, cultured overnight at 37° C. in a cell culture incubator. After carefully remove plating medium, 80 ul/well of pre-warmed assay medium was added, followed by adding 10 ul/well test compounds or bicalutamide (final concentration from 20 uM to 0.1 uM), incubated at 37° C. for 30 minutes, then adding 10 ul/well freshly prepared Methyltrienolone (R1881, AR agonist) (final concentration 1 ng/ml) to each well, incubate at 37° C. for 48-hour. At the end of incubation, 20 μl MTT (2.5 mg/ml in PBS) was added to each well, and the cells were further incubated for 2 h at 37 C to allow a complete reaction between the dye and the enzyme mitochondrial dehydrogenase in the viable cells. After removal of the residual dye and medium, 100 μl dimethylsulfoxide was added to each well, and the absorbance at 570 nm was measured with an microplate reader. The fold induction over background by 1 nM R1881 in the absence of test compounds is standardized as 100% and experimental result is expressed as percentage of inhibition by testing compounds at 2.5 micromolar (uM). The results are shown in Table 2.

TABLE 2

Inhibition of cell viability of prostate cancer cells

| Compound | LNCaP % inhibition at 2.5 uM | 22RV1 % inhibition at 2.5 uM |
|---|---|---|
| Bicalutamide | 21% | <10% |
| Compound of Example 1 | 70% | 31% |
| Compound of Example 2 | 59% | 41% |
| Compound of Example 8 | 86% | 59% |

TABLE 2-continued

Inhibition of cell viability of prostate cancer cells

| Compound | LNCaP % inhibition at 2.5 uM | 22RV1 % inhibition at 2.5 uM |
|---|---|---|
| Compound of Example 10 | 91% | 69% |
| Compound of Example 11 | 85% | 56% |
| Compound of Example 12 | 86% | 61% |
| Compound of Example 18 | 91% | 57% |
| Compound of Example 19 | 87% | 63% |
| Compound of Example 20 | 68% | 44% |
| Compound of Example 24 | 47% | 27% |
| Compound of Example 32 | 87% | 64% |

As is clear from Table 2, the compounds of the present invention showed stronger inhibitory activity against both hormone sensitive and hormone refractory cells, as compared with bicalutamide.

C57BL/6 Mouse Hair Growth Model

Six- to 8-wk-old male C57BL/6 mice in the telogen stage of the hair cycle, weighing 15-20 g, were purchased and housed in community cages under standard conditions. The growth phase of the hair cycle (anagen) was induced in the back skin of mice with all follicles in the resting phase of the hair cycle (telogen; as judged from their homogeneously pink skin color) by being shaved on the lower back using an electric shaver under mild anesthesia. Only mice in the telogen phase (pink skin) were used in the studies. Twenty microliters of test article at two concentrations in propylene glycol/ethanol (30:70, v/v) or the vehicle control was topically applied to the shaved lower back of the mice to cover an area of approximately 1 cm$^2$ (20 uL/cm$^2$). Five mice were used in each group. The mice were treated with the compound by topical application twice daily (BID) for 4 weeks. Local irritation was recorded daily before each application, and hair growth scores were recorded twice per week. The scoring system for mouse hair growth was 0 to 4: 0=no hair growth, pink skin color; 1=skin color in shaved area changes from pink to gray without visible hair growth, indicating the onset of anagen; 2=skin color in shaved area is black with tiny hairs; 3=short black hair in shaved area; and 4=hair in shaved area is almost close to surrounding area. A reference androgen receptor antagonist (RU-58841) was included in all studies as comparison.

By way of example, the compound of example 12 demonstrated excellent in vivo activity in mouse models for hair growth. This novel androgen receptor antagonist (at 0.2% and 1% concentration dissolved in 30% propylene glycol and 70% ethanol) stimulated hair growth in dose dependent patterns (FIG. 1). Compared to a known androgen receptor antagonist, RU-58841, the compound of example 12 displayed better in vivo activity for promoting hair growth.

The results of this study showed that compounds of the invention demonstrated remarkable in vivo activity for stimulating hair growth and possessed desirable physiochemical properties for dermal delivery, indicating the compounds of the present invention are expected to be excellent therapeutics for promoting hair growth and/or other clinical indications such as reducing oily skin due to their desirable local biological effect against the androgen receptor and result in low systemic exposure to avoid unwanted potential side effects.

What I claim is:

1. A compound of formula (I):

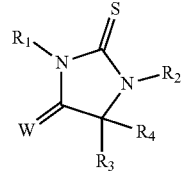

(I)

or a pharmaceutically-acceptable salt, solvate or hydrate thereof, wherein $R_1$ is selected from

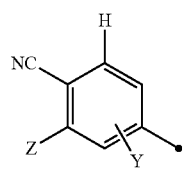

wherein Z is selected from $CF_3$, alkoxy, $CF_3O$, halogen, cyano and $C_1$-$C_4$ alkyl optionally substituted with one or more halogens;

Y is selected from halogen, alkoxy, hydroxyl, $CF_3O$ and cyano;

W is oxygen;

$R_3$ and $R_4$ are independently selected from $C_1$-$C_4$ alkyl optionally substituted with one or more fluoro or hydroxyl groups, or $R_3$ and $R_4$ and the carbon to which they are attached together form a 3-6 membered cycloalkyl ring, wherein one or more carbons may be optional substituted with one or more fluoro or hydroxyl groups, and wherein one of the carbons is optionally an oxygen or nitrogen; and $R_2$ is an aryl or heteroaryl group substituted with one or more $C_1$-$C_6$ alkyl, C(O)NHR", $SO_2R$", $SO_2NHR$", cyano, hydroxyl, alkoxy, C(S)NHR", C(O)OR", $CH_2(CH_2)_mQ$, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R$", $SO_2NHR$", cyano, hydroxyl, alkoxy, C(S)NHR" and C(O)OR"; or $R_2$ is a substituted or unsubstituted alkyl or heterocyclic group.

2. The compound of claim 1 wherein Y is halogen or cyano.

3. The compound of claim 1 wherein $R_3$ and $R_4$ and the carbon to which they are attached together form a cyclopropyl, cyclobutyl, cyclopentyl or cyclohexyl ring which may be optionally substituted with one or more fluoro or hydroxyl groups or $R_3$ and $R_4$ are methyl.

4. The compound of claim 1 wherein $R_2$ is a substituted pyridyl group or 6-methyl-pyridin-3-yl.

5. A compound of claim 1 wherein $R_1$ is

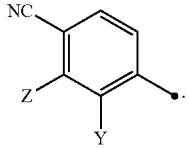

6. The compound of claim 1 wherein Z is selected from $CF_3O$, methyl, $CH_2F$, $CHF_2$, $CF_3$, methoxy, halogen and cyano.

7. The compound of claim 1 wherein $R_2$ is a substituted pyridyl group, 6-methyl-pyridin-3-yl, 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

8. The compound of claim 1 selected from

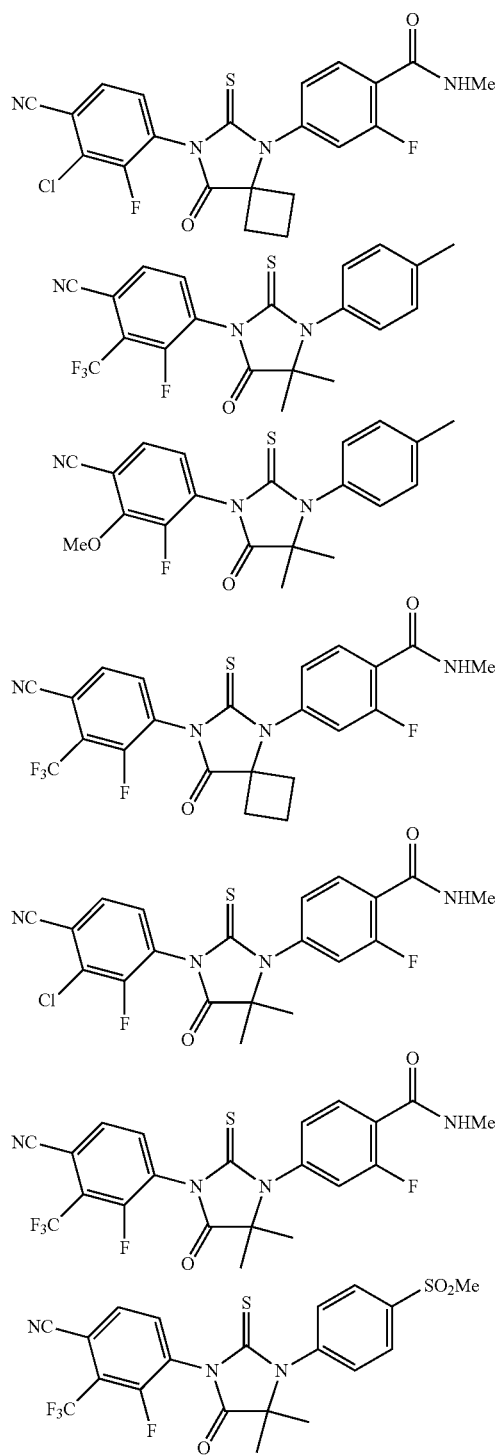

-continued

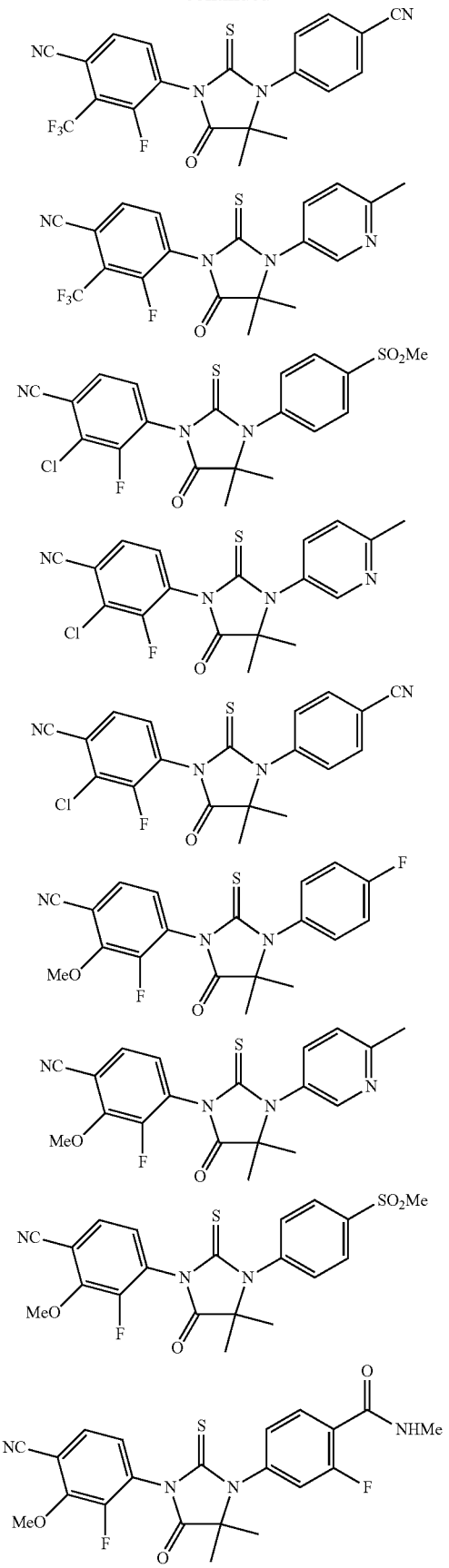

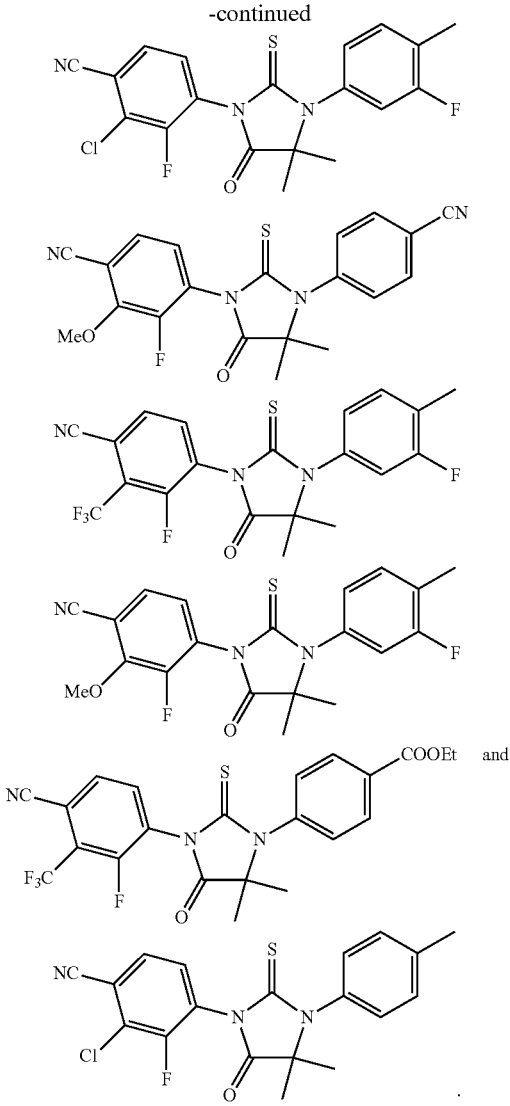

9. A compound of formula (IV)

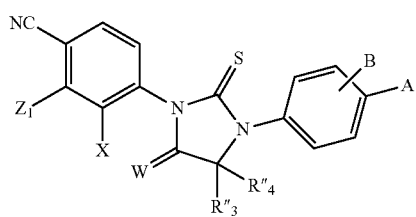

or a pharmaceutically-acceptable salt, solvate or hydrate thereof,
wherein $Z_1$ is selected from $CF_3O$, methyl, $CH_2F$, $CHF_2$, $CF_3$, methoxy, halogen and cyano;
X is selected from halogen, alkoxy, $CF_3O$, hydroxyl and cyano;
W is oxygen;
$R''_3$ and $R''_4$ are methyl, or $R''_3$ and $R''_4$ and the carbon to which they are attached together form a 3-6 membered cycloalkyl ring optionally substituted with one or more fluoro or hydroxyl groups;

B is independently selected from one or more hydrogen, cyano, methyl, $CF_3$ or halogen; and A is selected from $C_1$-$C_6$ alkyl, C(O)NHR", $SO_2R"$, $SO_2NHR"$, cyano, hydroxyl, alkoxy, C(S)NHR", C(O)OR", $CH_2(CH_2)_mQ$, halogen and a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $SO_2R"$, $SO_2NHR"$, cyano, hydroxyl, alkoxy, C(S)NHR" and C(O)OR".

10. The compound of claim 9 wherein A is methyl, ethyl, halogen, $C(O)NHCH_3$, $C(O)NH_2$, cyano, methoxy, ethoxy, $SO_2Me$, $SO_2NH_2CH_3$ and $SO_2NH_2$.

11. The compound of claim 9 selected from

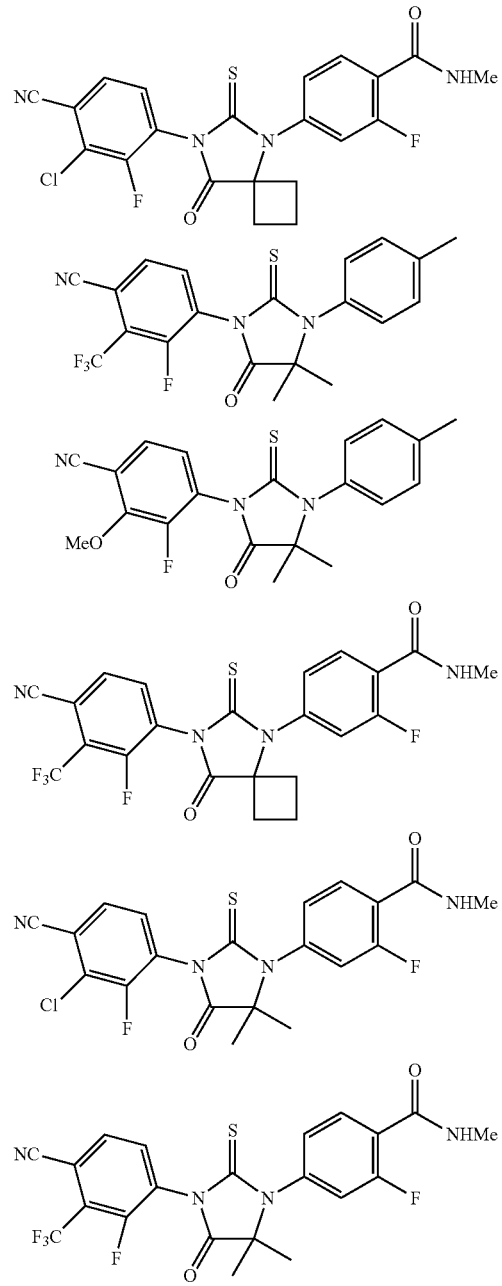

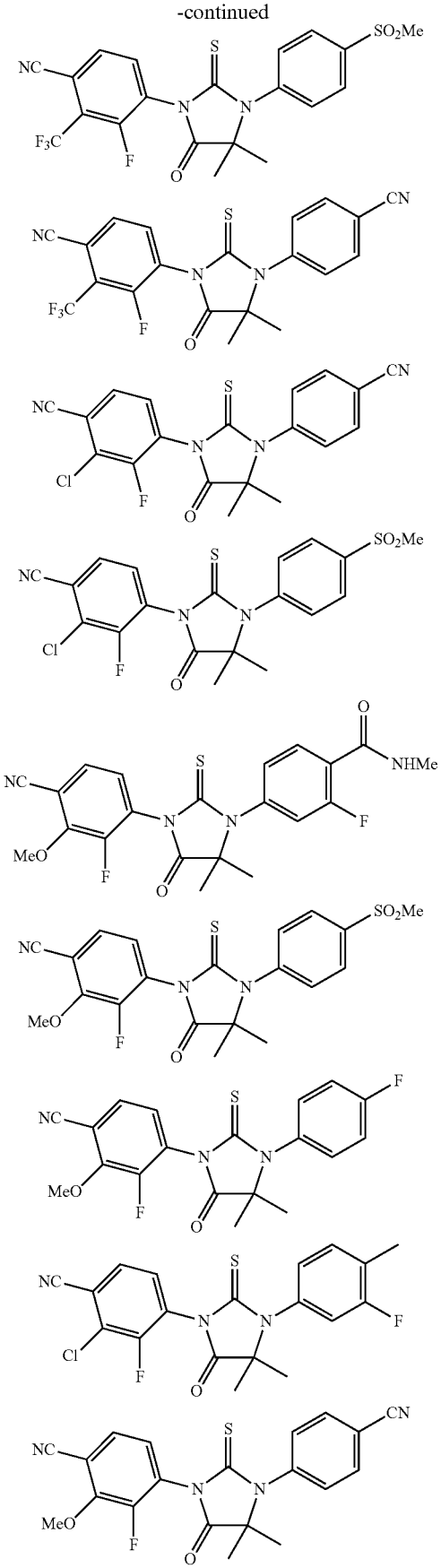

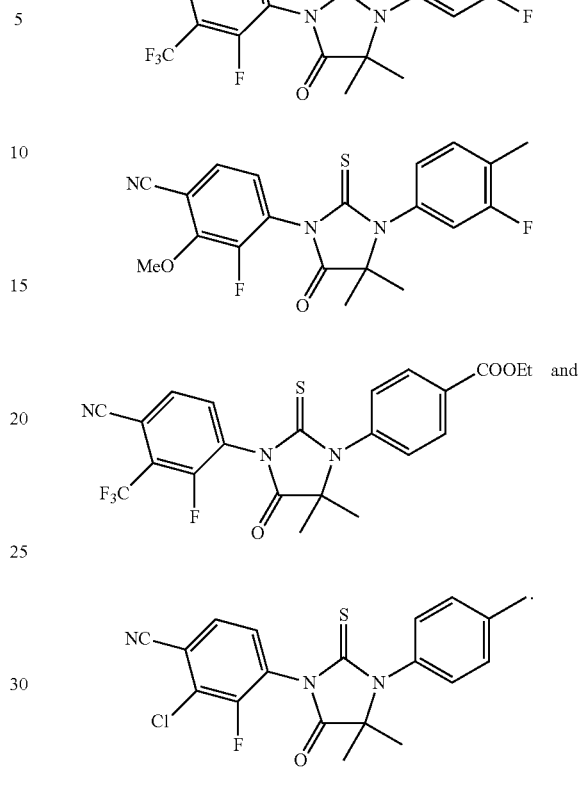

12. The pharmaceutical composition comprising a compound of claim 1 and a pharmaceutically-acceptable carrier, diluent or excipient.

13. The pharmaceutical composition comprising a compound of claim 9 and a pharmaceutically-acceptable carrier, diluent or excipient.

14. The pharmaceutical composition of claim 9, which is a topical pharmaceutical formulation for dermal applications.

15. A method for reducing the progression of, treating or regressing a disease or disorder related to androgen receptor activity selected from hormone sensitive prostate cancer or hormone refractory prostate cancer, benign prostatic hyperplasia, acne, excess sebum and alopecia;

by administering to a subject afflicted therewith, a compound or a pharmaceutical composition thereof wherein the compound has formula (I):

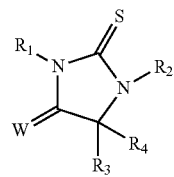

(I)

or a pharmaceutically-acceptable salt, solvate or hydrate thereof, wherein $R_1$ is selected from

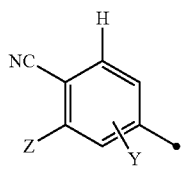

wherein Z is selected from $CF_3$, alkoxy, $CF_3O$, halogen and cyano;
Y is a halogen;
W is oxygen;
$R_3$ and $R_4$ are methyl, or $R_3$ and $R_4$ and the carbon to which they are attached together form a 3-6 membered cycloalkyl ring; and
$R_2$ is an aryl pyridyl group substituted with one or two $C_1$-$C_6$ alkyl, C(O)NHR", $SO_2R$", $SO_2NHR$", cyano, hydroxyl, alkoxy, C(S)NHR", C(O)OR", $CH_2(CH_2)_mQ$, halogen or a 5-6 membered heteroaryl group, where R" is selected from hydrogen, $C_1$-$C_6$ alkyl, $C_1$-$C_6$ cycloalkyl and $C_1$-$C_6$ alkenyl; m is an interger selected from 0 to 6; and Q is selected from C(O)NHR", $SO_2R$", $SO_2NHR$", cyano, hydroxyl, alkoxy, C(S)NHR" and C(O)OR".

16. A method for reducing the progression of, treating or regressing a disease or disorder related to androgen receptor activity selected from
hormone sensitive prostate cancer or hormone refractory prostate cancer, benign prostatic hyperplasia, acne, hirsutism, excess sebum and alopecia;
comprising administering to a subject afflicted therewith a compound or a pharmaceutical composition thereof wherein the compound has formula (IV)

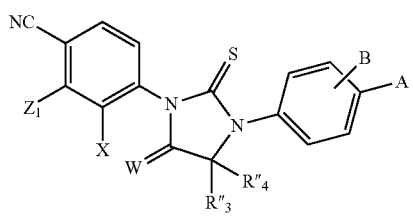

(IV)

or a pharmaceutically-acceptable salt, solvate or hydrate thereof,
wherein $Z_1$ is selected from $CF_3O$, methyl, $CH_2F$, $CHF_2$, $CF_3$, methoxy, halogen and cyano;
X is selected from halogen, alkoxy, $CF_3O$, hydroxyl and cyano;
W is oxygen;
R"$_3$ and R"$_4$ are methyl, or R"$_3$ and R"$_4$ and the carbon to which they are attached together form a 3-6 membered cycloalkyl ring;
B is selected from hydrogen, cyano, methyl, $CF_3$ or halogen; and
A is selected from $C_1$-$C_6$ alkyl, C(O)NHR", $SO_2R$", $SO_2NHR$", cyano, hydroxyl, alkoxy, C(S)NHR", C(O)OR", $CH_2(CH_2)_mQ$, halogen and a 5-6 membered heteroaryl group, where R" is selected from hydrogen, $C_1$-$C_6$ alkyl, $C_1$-$C_6$ cycloalkyl and $C_1$-$C_6$ alkenyl; m is an integer selected from 0 to 6; and Q is selected from C(O)NHR", $CO_2R$", $SO_2NHR$", cyano, hydroxyl, alkoxy, C(S)NHR" and C(O)OR".

17. The method of claim 15 wherein $R_2$ is 6-methyl-pyridin-3-yl, 4-fluorophenyl, 2-fluoro-4-methylamido-phenyl, 4-tolyl, 3-fluoro-4-methyl-phenyl, 4-cyanophenyl, 4-methylsulfonyl-phenyl, or 4-ethoxylcarbonylphenyl.

18. The method of claim 15 wherein the compound is selected from

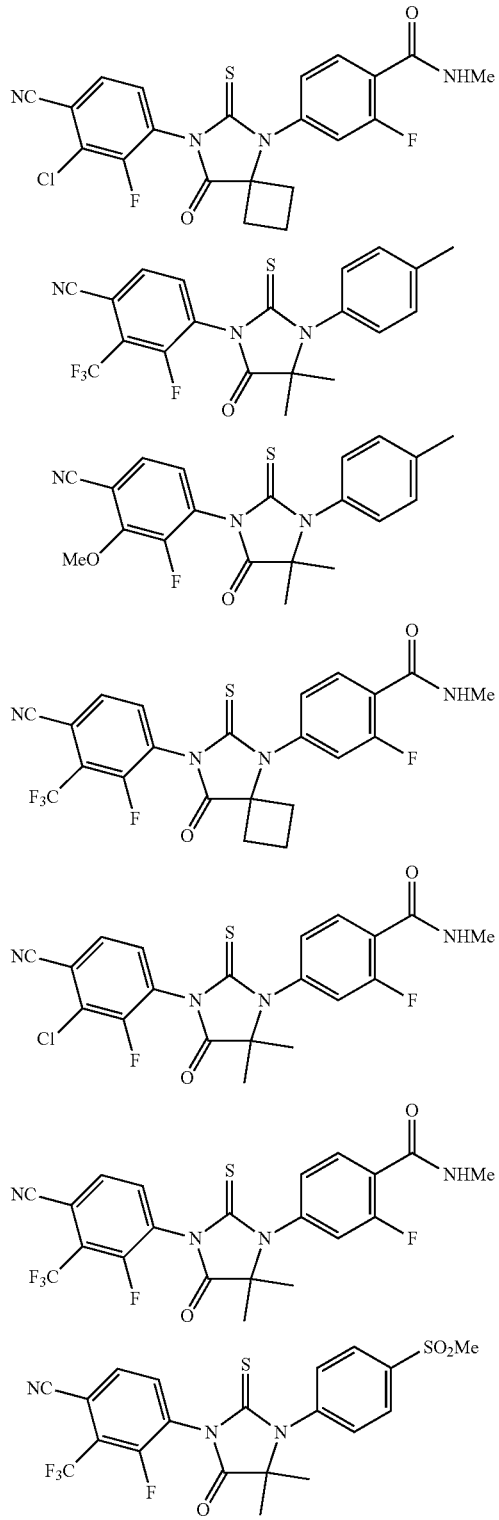

95
-continued
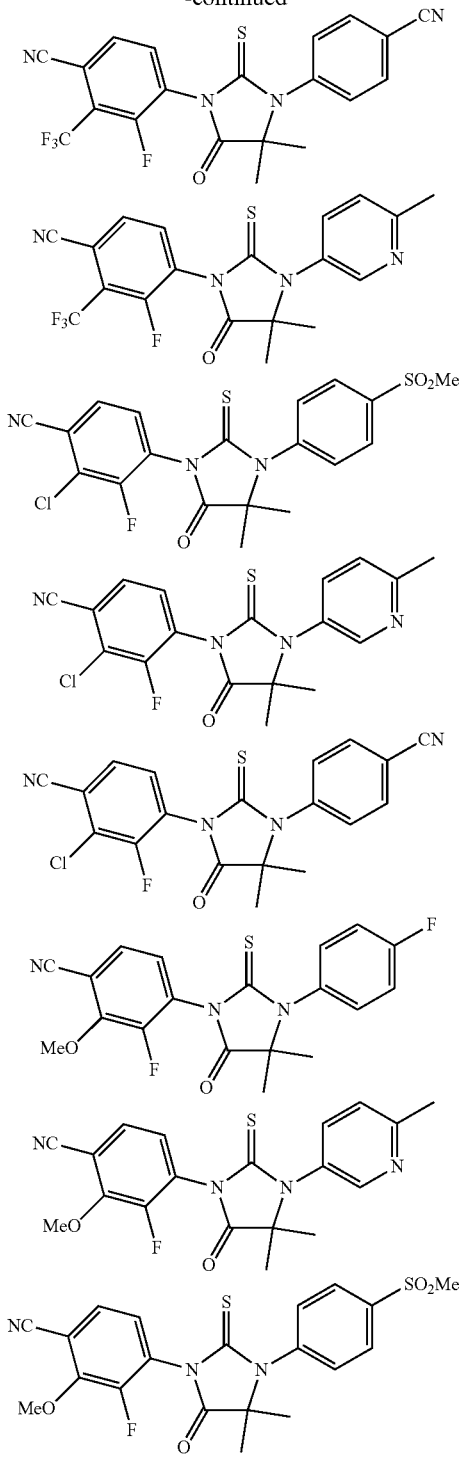
96
-continued
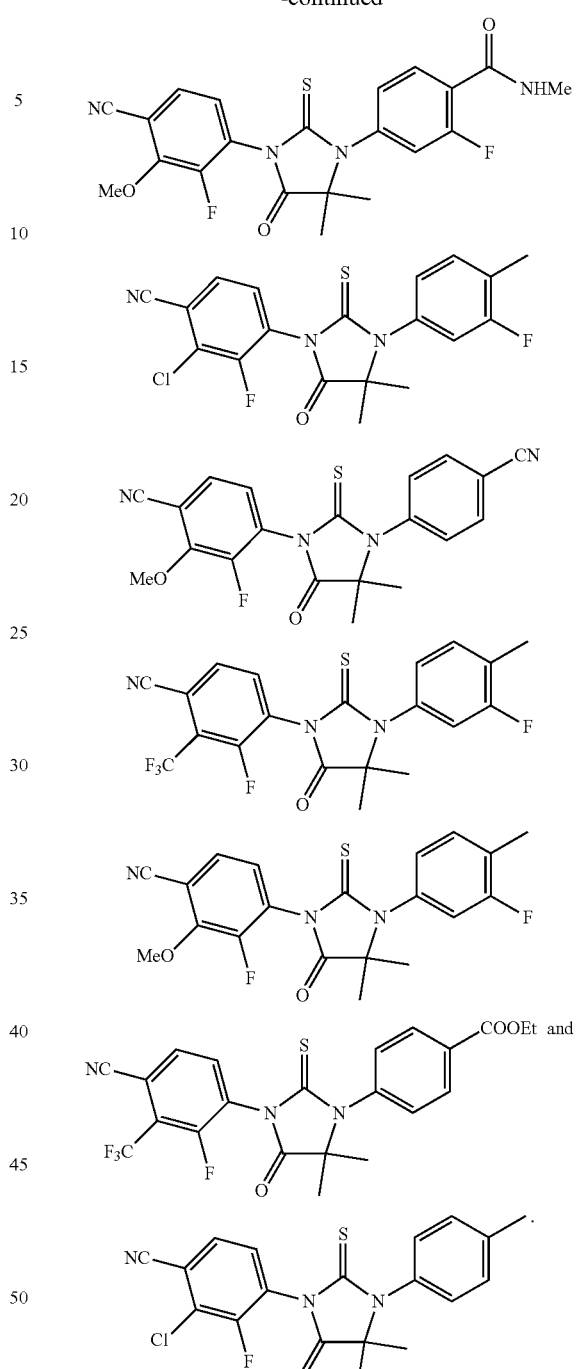
* * * * *

UNITED STATES PATENT AND TRADEMARK OFFICE
CERTIFICATE OF CORRECTION

PATENT NO. : 8,809,550 B2
APPLICATION NO. : 13/395066
DATED : August 19, 2014
INVENTOR(S) : Youzhi Tong Page 1 of 4

It is certified that error appears in the above-identified patent and that said Letters Patent is hereby corrected as shown below:

In the Specification

In column 77, lines 32-54, delete:

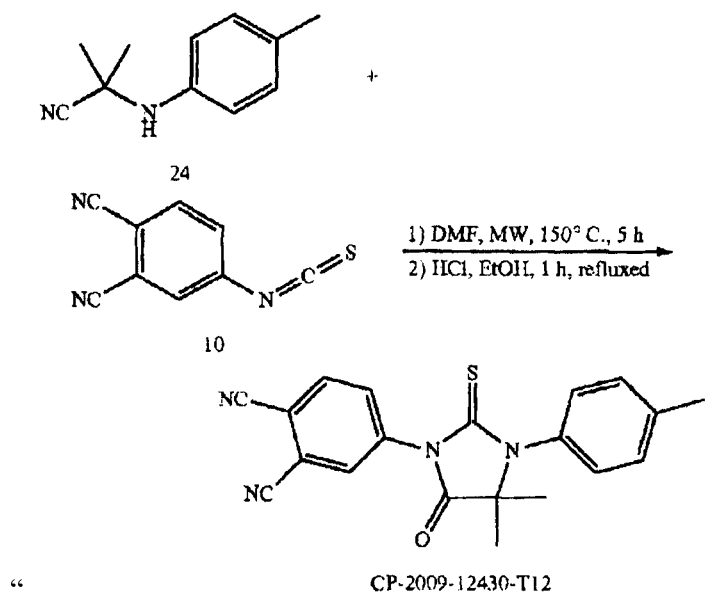

"

And insert

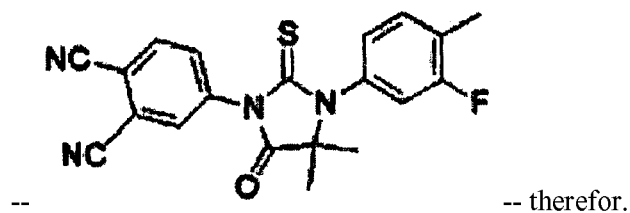

-- -- therefor.

Signed and Sealed this
Seventh Day of April, 2015

Michelle K. Lee
*Director of the United States Patent and Trademark Office*

CERTIFICATE OF CORRECTION (continued)
U.S. Pat. No. 8,809,550 B2

In column 78, lines 10-30, delete:

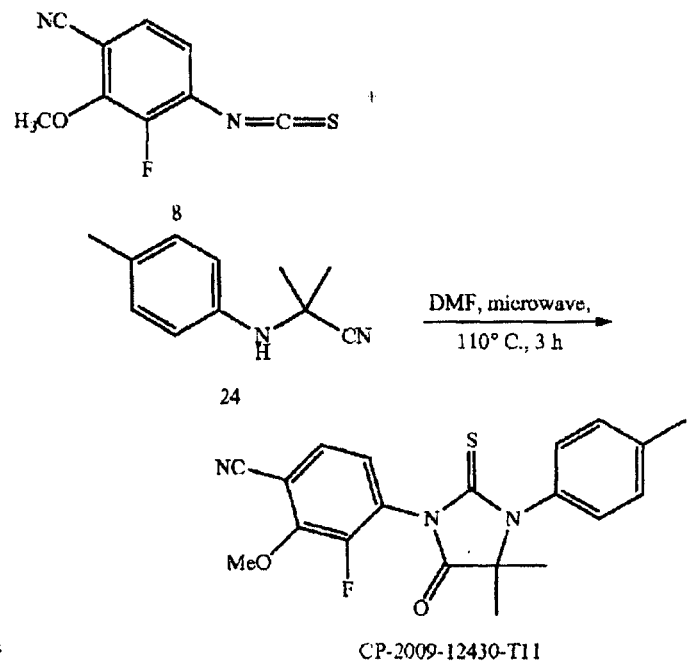

" CP-2009-12430-T11 "

And insert

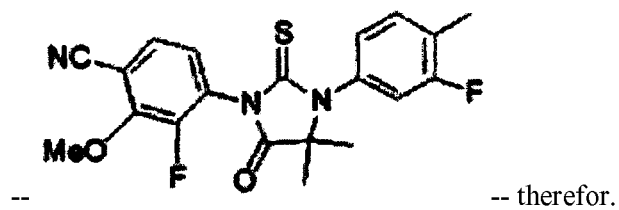

-- — therefor.

In column 80, lines 10-32, delete:

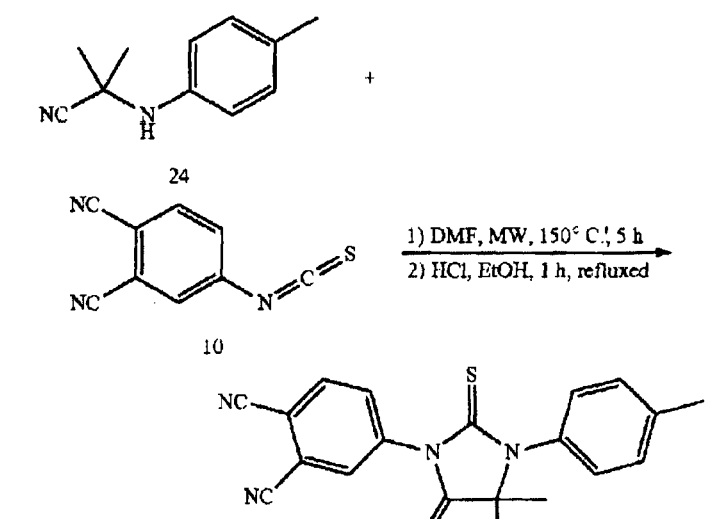

" CP-2009-12430-T12 "

And insert
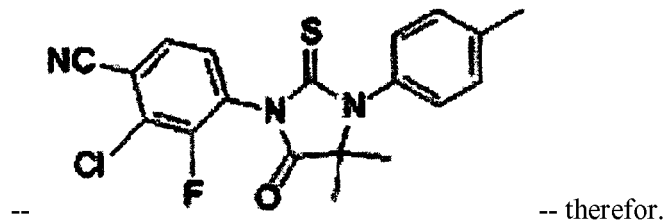
-- -- therefor.
In column 80, lines 55-69 and column 81, lines 1-10, delete:
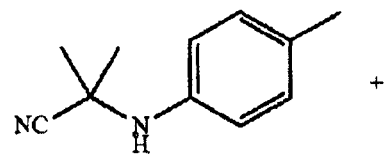 +
24
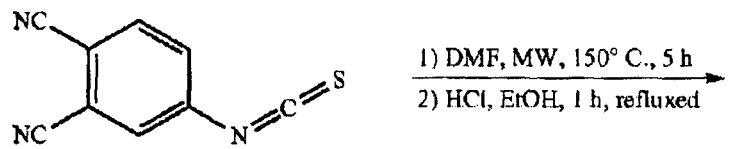
10
-continued
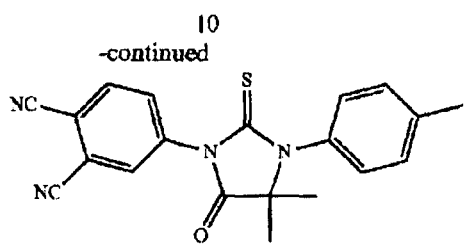
" CP-2009-12430-T12 "
And insert
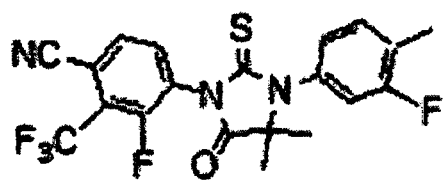
-- -- therefor.

CERTIFICATE OF CORRECTION (continued)
U.S. Pat. No. 8,809,550 B2

In column 81, lines 30-55, delete:

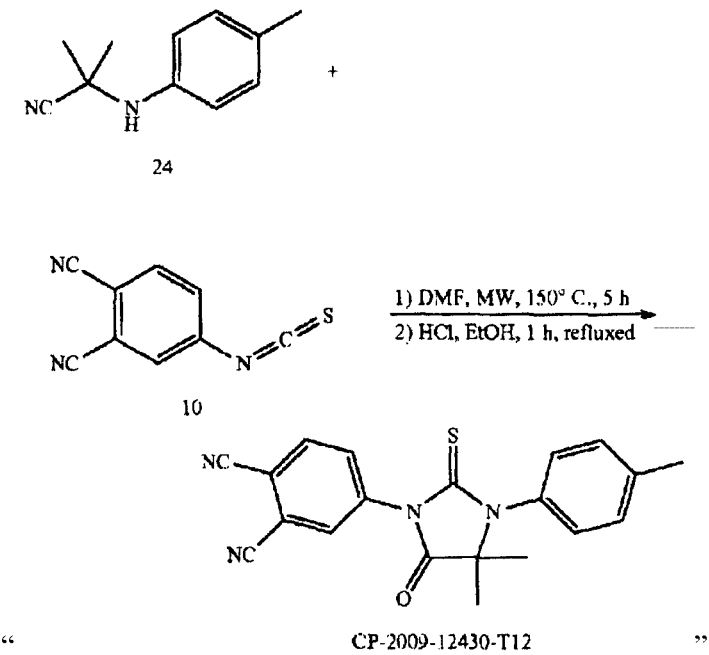

"       CP-2009-12430-T12       "

And insert

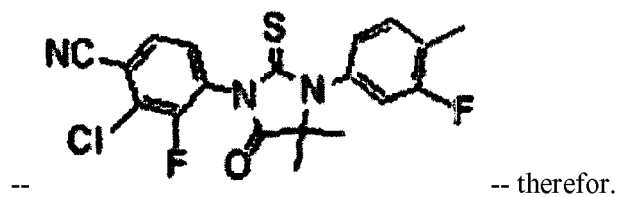

-- therefor.